(12) United States Patent
Tanaka et al.

(10) Patent No.: US 8,956,879 B2
(45) Date of Patent: Feb. 17, 2015

(54) ANALYSIS DEVICE AND METHOD USING THE SAME

(71) Applicant: Panasonic Healthcare Co., Ltd., Toon-shi, Ehime (JP)

(72) Inventors: Masanori Tanaka, Ehime (JP); Hirotaka Tanaka, Ehime (JP); Hiroshi Saiki, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 0 days.

(21) Appl. No.: 13/770,499

(22) Filed: Feb. 19, 2013

(65) Prior Publication Data

US 2013/0164763 A1  Jun. 27, 2013

Related U.S. Application Data

(62) Division of application No. 12/681,493, filed as application No. PCT/JP2008/002779 on Oct. 3, 2008, now Pat. No. 8,415,140.

(30) Foreign Application Priority Data

| Oct. 4, 2007 | (JP) | 2007-260450 |
| Oct. 4, 2007 | (JP) | 2007-260451 |
| Oct. 18, 2007 | (JP) | 2007-270764 |
| Oct. 26, 2007 | (JP) | 2007-278249 |
| Nov. 14, 2007 | (JP) | 2007-294983 |
| Feb. 1, 2008 | (JP) | 2008-022195 |

(51) Int. Cl.
| G01N 33/72 | (2006.01) |
| G01N 33/49 | (2006.01) |
| G01N 33/545 | (2006.01) |

(52) U.S. Cl.
CPC ............ *G01N 33/721* (2013.01); *G01N 33/491* (2013.01); *G01N 33/545* (2013.01)
USPC ............................. 436/518; 435/7.25; 422/73

(58) Field of Classification Search
CPC ............ G01N 33/5304; G01N 33/721; G01N 33/723; G01N 2021/825; G01N 21/82; C12Q 2565/113
See application file for complete search history.

(56) References Cited

U.S. PATENT DOCUMENTS

| 3,901,658 A | 8/1975 | Burtis et al. |
| 4,035,156 A | 7/1977 | Shumate |

(Continued)

FOREIGN PATENT DOCUMENTS

| CN | 1449494 | 10/2003 |
| CN | 1517709 | 8/2004 |

(Continued)

*Primary Examiner* — Melanie Y Brown
*Assistant Examiner* — Rebecca Martinez
(74) *Attorney, Agent, or Firm* — Hamre, Schumann, Mueller & Larson, P.C.

(57) ABSTRACT

An analysis device includes: a separation cavity 18 for separating a test liquid into a solution component and a solid component by using a centrifugal force; a higher specific gravity component quantitative cavity 23 for holding a portion of the separated solid component which has been transferred; a sample solution overflow cavity 22 arranged between the higher specific gravity component quantitative cavity 23 and the separation cavity 18 and connected to a connecting channel 21 for transporting the sample liquid from the separation cavity 18; and a capillary cavity 19 formed in the separation cavity 18 for temporarily holding a separated solution component (blood plasma) in the separation cavity 18. A blood plasma component 57a remaining in the separation cavity 18 is trapped by the capillary cavity 19.

7 Claims, 50 Drawing Sheets

(56) References Cited

U.S. PATENT DOCUMENTS

| | | | |
|---|---|---|---|
| 4,605,686 A * | 8/1986 | Obana | 524/547 |
| 5,372,948 A | 12/1994 | Yip | |
| 6,063,589 A | 5/2000 | Kellogg et al. | |
| 7,754,472 B2 | 7/2010 | Schwind et al. | |
| 8,431,415 B2 | 4/2013 | Shigenobu | |
| 2002/0064800 A1 | 5/2002 | Sando et al. | |
| 2002/0106786 A1 | 8/2002 | Carvalho et al. | |
| 2004/0232074 A1 | 11/2004 | Peters et al. | |
| 2004/0265171 A1 * | 12/2004 | Pugia et al. | 422/58 |
| 2005/0123447 A1 | 6/2005 | Koike et al. | |
| 2008/0044926 A1 | 2/2008 | Honjo et al. | |
| 2008/0073297 A1 | 3/2008 | Shiraishi et al. | |
| 2008/0293074 A1 | 11/2008 | Tanaka et al. | |

FOREIGN PATENT DOCUMENTS

| | | |
|---|---|---|
| CN | 1551982 | 12/2004 |
| CN | 1618020 | 5/2005 |
| EP | 0407827 | 1/1991 |
| EP | 1503209 | 2/2005 |
| JP | 3-46566 | 2/1991 |
| JP | 05-504828 | 7/1993 |
| JP | 5-508709 | 12/1993 |
| JP | 07-005178 | 1/1995 |
| JP | 2002-221485 | 8/2002 |
| JP | 2004-150804 | 3/2004 |
| JP | 2004-283828 | 10/2004 |
| JP | 2004-301733 | 10/2004 |
| JP | 2005-114468 | 4/2005 |
| JP | 2005-181350 | 7/2005 |
| JP | 2006-292410 | 10/2006 |
| JP | 2007-10435 | 1/2007 |
| JP | 2007-017342 | 1/2007 |
| JP | 2007-021450 | 2/2007 |
| JP | 2007-040833 | 2/2007 |
| JP | 2007-78676 | 3/2007 |
| JP | 2007-114162 | 5/2007 |
| JP | 2007-519938 | 7/2007 |
| JP | 2007-232673 | 9/2007 |
| WO | WO 89/11102 | 11/1989 |
| WO | WO 91/18656 | 12/1991 |
| WO | WO 2005/116662 | 12/2005 |
| WO | WO 2006/068206 | 6/2006 |
| WO | WO 2006/112339 | 10/2006 |

* cited by examiner

AA-AA

B-B

C-C

D-D

E-E

F-F

G—G

G—G

ANALYSIS DEVICE AND METHOD USING THE SAME

This application is a division of U.S. Ser. No. 12/681,493, filed Apr. 2, 2010, which is a U.S. National Stage Application of PCT/JP2008/002779, filed Oct. 3, 2008, which applications are incorporated herein by reference.

TECHNICAL FIELD

The present invention relates to an analysis device to be used to analyze a liquid collected from a living organism or the like, and to an analysis apparatus and analysis method using the same. More specifically, the present invention relates to a method of collecting a solid component of a liquid separated in an analysis device, and in particular, to a technique for collecting a blood cell component from blood.

BACKGROUND ART

Conventionally, as a method of collecting and analyzing a liquid collected from a living organism or the like, an analysis method is known which uses an analysis device that forms a liquid channel. The analysis device is capable of controlling a fluid using a rotating apparatus. Since the analysis device is capable of performing solution measurement, separating solid components, transferring and distributing a separated fluid, mixing a solution with a reagent, and the like by utilizing centrifugal force, various biochemical analyses can be carried out.

With an analysis device 501 described in Patent Document 1 (Japanese Patent Laid-Open No. 2007-78676) which transfers a solution using centrifugal force, as illustrated in FIG. 51A, after blood held in a separation cavity 70 is centrifugally separated by the rotation of the analysis device 501, the analysis device 501 is connected to a measurement channel 73 from a lower side of the separation cavity 70 via a connecting channel 71 and an overflow channel 72, whereby a blood cell component is capillary transferred. A blood cell component of a predetermined amount can be collected by trapping a blood plasma component remaining inside the connecting channel 71 in the overflow channel 72 by centrifugal separation and subsequently transferring only the blood cell component to the measurement channel 73. The blood plasma component trapped in the overflow channel 72 is drawn into an overflow cavity 74.

In addition, as illustrated in FIG. 55, Patent Document 1 is configured such that: a sample liquid is injected from an inlet 68 into a containment cavity 69 using an insertion instrument such as a pipette; the sample liquid is transferred to the separation cavity 70 and centrifugally separated by a rotation of the analysis device 501; a solution component is subsequently collected in the measurement channel 73 via the connecting channel 71; the solution component inside the measurement channel 73 is transferred to a measurement spot 76 by a next rotation of the analysis device 501; and, at the same time, unnecessary sample liquid inside the separation cavity 70 is discharged to an overflow cavity 78 utilizing a siphon effect of a connecting channel 77.

Conventionally, large-sized automatic analysis apparatuses capable of singlehandedly causing a reaction between a biological sample such as blood and an analytical reagent, and quantifying various components in the biological sample have been put into practical use and have become indispensible in the field of medicine. However, such apparatuses have not necessarily been introduced at all hospitals. In particular, there are quite a few small-scale medical institutions such as clinics that outsource sample analysis due to various reasons including operational costs. When adopting a system in which analysis is outsourced, a certain amount of time is required until analysis results are obtained. As a result, patients must inconveniently revisit the hospital in order to receive appropriate treatment based on the analysis results, or hospitals are disadvantageously inhibited from promptly responding to matters of urgency such as emergency patients.

In such a background, there have been demands from the market for an analysis apparatus with higher accuracy and a high degree of operational flexibility which is capable of reducing cost, reducing the amount of sample liquid required, reducing the size of the apparatus, and performing short-time measurement and simultaneous multiple measurement.

When contemplating the realization of an analysis apparatus with a high degree of operational flexibility, for example, the analysis apparatus ideally satisfies a condition in that the concentrations of a plurality of types of components can be measured in a short period of time at a high accuracy from a small amount of specimen collected by finger-prick blood sampling or the like. However, the amount of specimen that can be obtained by finger-prick blood sampling or the like without causing stress is, at the most, ten-odd microliters. As such, when a specimen in such a small amount is analyzed without modification, it is technically difficult to satisfy the aforementioned condition and, in particular, perform the analysis of a plurality of types of components at high accuracy.

As a solution to this problem, there is a method involving increasing the sensitivity of an analysis system and, by diluting a small amount of specimen with a diluent to increase the volume of the specimen, analyzing a specific component. In addition, diluents are frequently utilized not only as a measure against minute specimens but also when there is a high concentration of any substance or due to limitations in an analysis apparatus.

In recent years, the concentration of glycated hemoglobin in blood has become a prerequisite test item in terms of testing the progression of various diseases. Since, among other reasons, glycated hemoglobin that is a hemoglobin derivative enables judgment of normal-time blood sugar levels from which is excluded the dietary influence of blood sugar level variations, glycated hemoglobin is often measured for purposes of early detection of adult diseases. Also referred to as hemoglobin A1c, glycated hemoglobin is formed when glucose binds with hemoglobin in red blood cells and is quantified as a ratio (%) of glycated hemoglobin to hemoglobin. General methods for measuring glycated hemoglobin include HPLC (high-performance liquid chromatography), immunization, and borate affinity. In particular, in order to measure a ratio of existing hemoglobin A1c, an immunization requires that hemoglobin and hemoglobin A1c be individually measured.

Hemoglobin is generally measured by utilizing the specific optical absorption property of hemoglobin at wavelengths of around 415 nm or around 540 nm. Methods of measurement at wavelengths of around 540 nm include a cyanmethemoglobin method and an SLS hemoglobin method.

In addition, the measurement of glycated hemoglobin (hemoglobin A1c) by an immunization requires a process in which: hemoglobin be first extracted from red blood cells by hemolyzing a blood sample; and a three-dimensional structure of hemoglobin be altered to expose glycated portions of hemoglobin protein from the inside to the outside of the three-dimensional structure in order to judge whether hemoglobin is non-glycated hemoglobin or glycated hemoglobin (hemoglobin A1c). This process is known as hemoglobin denaturation. By further causing a reaction with an antibody that specifically identifies glycated portions, an amount of glycated hemoglobin (hemoglobin A1c) can be immunologically measured.

Known methods of optically analyzing a biological fluid using a glycated hemoglobin analysis device includes a reactive cassette for sequential reactive testing which involves non-centrifugal and non-capillary operations.

FIG. 52A illustrates a hemoglobin turbidimetry reactive cassette used for analyzing a biological fluid described in Patent Document 2 (Japanese Patent Laid-Open No. 03-046566). The described reactive cassette includes a container main body 400 having permeable surfaces as upper and lower surfaces, a capillary holder 401 containing a sample, and a diluent container 402 containing a diluent. An oxidant 403, an antibody particle 404, and a coagulant 405 are set in the container main body 400.

An analysis process by the reactive cassette involves inserting the capillary holder 401 having sampled a sample into the container main body 400 as illustrated in FIG. 52B, and supplying the diluent 406 from the diluent container 402 to the container main body 400. By tilting the container main body 400 as seen from FIG. 52B to FIG. 52C, the sample, the oxidant 403, and the diluent 406 are mixed inside a reaction channel 407. The mixed liquid is further transferred to the antibody particle 404 and to the coagulant 405. After a reaction process, the container main body 400 is set to the posture illustrated in FIG. 52C and a liquid mixture 409 is optically accessed from a window 408 to enable various biological analyses such as the turbidity of the liquid mixture 409.

Furthermore, known methods of optically analyzing a biological fluid which may be found in information provided in other prior art documents include a method described in Patent Document 3 (National Publication of International Patent Application No. 05-508709) in which analysis is performed using an analysis device in which a liquid channel is formed.

FIG. 53 illustrates an analysis device to be used for analyzing a biological fluid described in Patent Document 3. An analysis device 246 in which is formed a liquid channel is capable of controlling a fluid by centrifugal force through the use of a rotation apparatus. Since the analysis device 246 can measure sample solutions, separate fluid components through centrifuge, transfer and distribute separated fluid components, and the like, various biochemical analyses can be performed.

More specifically, a rotation apparatus 200 includes a sample receiving container 248 having a sample inlet port 250 and a diluent cavity 252 containing a diluent. Utilizing the centrifugal force caused by a rotation 218 of the analysis device 246, both a sample liquid and the diluent are transferred to a mixing cavity 205 where the sample liquid and the diluent are mixed through the rotation and deceleration of the analysis device 246. After a constant period of time, a condensed cellular component in the sample liquid is received in a separation cavity that is a cell-holding range 206 formed at an outer circumference in a radial direction of a receiving/mixing cavity 254. Subsequently, a liquid containing the cellular component is transferred to a fractionation cavity 260 via a flow limiting path 262, where the cellular component of the liquid containing the cellular component is further condensed by the rotation and deceleration of the analysis device 246 to be held in a cell-holding range 211 formed at the outer side of the fractionation cavity 260 in a radial direction. Meanwhile, a liquid containing no cells is transferred into a distribution path 266 and into an optical cuvette inside an analysis cavity 268 where a specific analysis is performed.

Furthermore, when the sample liquid is blood and the cellular component is a blood cell component, the receiving/mixing cavity 254 and the fractionation cavity 260 can effectively extract and distribute a blood plasma component from which the blood cell component has been separated and removed.

As described, known analysis methods for measuring the amount of an analysis object existing in a liquid test sample include a method involving an analytical reaction with an analytical reagent and performing an analysis using spectrometry. Dedicated instruments such as analytical reaction containers or apparatuses to which the method is applied are particularly useful when implementing immunoassay that requires a large number of troublesome operational stages including the use of pipettes, mixing of a liquid test sample and an analytical reagent, and heating and incubation. In addition, the method eliminates the need of conveying such dedicated instruments to an inspection station and enables prompt in-situ measurement.

As illustrated in FIG. 54, Patent Document 4 (Japanese Patent Laid-Open No. 2004-150804) is configured such that: a sample liquid S injected into a liquid receiving unit 600 of an analysis device is transferred by centrifugal force and capillary action to a measurement spot 601B of the analysis device via a channel 601 of the analysis device; at the measurement spot 601B, a reaction is caused between a reagent portion 602 set to the measurement spot 601B and the sample liquid S; and a mixed liquid at the measurement spot 601B is optically accessed to read a color reaction of the mixed liquid.

An optical access by the analysis apparatus refers to irradiating the inside of the measurement spot 601B where the reagent has been dissolved by the sample liquid S and a color reaction is taking place with a light source mounted in the analysis apparatus, and detecting reflected light or transmitted light at a light receiving section. The concentration of a specific component in the sample liquid is converted from an absorbance (ABS), which is a logarithm of a ratio between irradiated light intensity and detected light intensity and is expressible as $$ABS = \log 10(I/O),$$

where I denotes irradiated light intensity (incident light intensity) and O denotes detected light intensity (outgoing light intensity), and from a so-called calibration curve, which is relational data between absorbance and concentration, stored in advance in the apparatus.

The analysis device is made up of a base substrate whose upper surface is formed with various depressions which form the channel 601, the measurement spot 601B, and the like, and a cover substrate that is bonded to the upper surface of the base substrate by an adhesive layer. The reagent 602 is carried and supported at the measurement spot 601B by dropping a requisite amount of the liquid reagent onto the measurement spot 601B before bonding the cover substrate to the upper surface of the base substrate. The analysis device is completed by bonding the base substrate and the cover substrate with an adhesive layer after the liquid reagent is cold cured or freeze-dried.

DISCLOSURE OF THE INVENTION

Problems to be Solved by the Invention

As illustrated in an enlarged view in FIG. 51B, in the conventional configuration described above, when w3 denotes the opening space of the overflow channel 72 and w4 denotes the opening space of the measurement channel 73, the conventional configuration attempts to collect a predetermined amount of a blood cell component by preferentially transferring a blood plasma component to an overflow channel 72 whose opening space is larger to trap the blood plasma component and transfer the blood cell component to a measurement channel 73 by setting w3>w4. However, in reality, a small amount of blood plasma also flows into the measurement channel 73 due to the influence of surface tension of wall surfaces, thereby preventing a full suppression of blood plasma contamination and causing variations in dilution ratio.

The present invention has been made to solve the conventional problems described above, and an object thereof is to provide an analysis device capable of accurately extracting a predetermined amount of a solid component (blood cells) in a sample and transferring the extracted solid component to an analysis process, and an analysis apparatus and an analysis method using the analysis device.

In addition, in Patent Document 1, air ducts 81 and 82 which communicate with the air are formed at inner-circumferential positions of the measurement spot 76 and the overflow cavity 78. During an analysis, the sample liquid is pressed in an outer-circumferential direction of the measurement spot 76 and the overflow cavity 78 by centrifugal force caused by the rotation of the analysis device 501 and therefore has a low risk of leakage to the outside. However, during a process of discarding the analysis device 501 once the analysis is completed, there is a high risk of a contamination accident occurring when the sample liquid leaks out from the air ducts 81 and 82 and an operator comes into contact with the sample liquid.

It is an object of the present invention to provide an analysis device capable of reducing the risk of leakage during handling of a sample liquid retained in the analysis device, and an analysis apparatus and an analysis method using the analysis device.

Furthermore, Patent Document 2 disadvantageously requires a large quantity of reaction liquid and makes it difficult to downsize a device. In addition, since the device is non-centrifugally operated, the device does not include a quantification mechanism. Therefore, the device is susceptible to a phenomenon in which a diluent naturally evaporates during the retention period of the diluent to the outside of a retaining container, resulting in a reduction in the diluent. The reduction in the diluent disadvantageously alters the amount of reaction liquid and causes measurement accuracy to deteriorate.

Moreover, while Patent Document 3 involves quantification and measurement techniques which utilize centrifugal force, with reactions utilizing an agglutination reaction using a latex reagent, the centrifugal force disadvantageously causes sedimentation of agglutinated substances generated during measurement and prevents accurate measurement.

It is an object of the present invention to provide an analysis method for an analysis device capable of automatically measuring hemoglobin and hemoglobin A1c components in a simple and prompt manner.

In addition, FIGS. 52B and 52C illustrate that even though attempts are made to move a mixed liquid including a sample and a diluent using gravity by rotation or a swinging motion so as to mix the mixed liquid with a reagent, in reality, since the amount of liquid in the analysis device is minute (in the order of several tens of μL), a state exists in which surface tension generated between the surface of an inner wall of the analysis device and the mixed liquid causes the mixed liquid to be pulled up against the inner wall of the analysis device to inhibit movement of the liquid, thereby preventing sufficient agitation.

The present invention has been made to solve the conventional problems described above, and an object thereof is to provide an analysis device and an agitation apparatus capable of sufficiently agitating and mixing a small amount of liquid with a reagent.

In FIG. 54, while the concentration of a specific component contained in the sample liquid S is converted using the method described earlier, the calculation is performed according to the Lambert-Beer Law.

$$ABS = \epsilon \cdot c \cdot L,$$

where ABS denotes absorbance, $\epsilon$ denotes a molar absorbance coefficient, c denotes the concentration of a measurement object, and L denotes an optical path length of the measurement object. As is apparent from the above equation, even when measuring measurement objects having the same concentration, variations in the optical path length of the measurement spot 601B of the analysis device result in errors included in absorbance in proportion to such variations. As a result, a concentration converted from a calibration curve also includes errors.

However, since variations in optical path lengths are caused by variations in parts or by variations in adhesive which occur during a bonding process, manufacturing innovations alone are insufficient for eliminating variations in optical path lengths.

In consideration thereof, in order to improve analysis accuracy, it is required that an optical path length be actually measured during manufacturing, an actual measurement value be converted into a barcode or the like as analysis device information to be written onto the analysis device, and a correction be performed upon analysis.

However, when attempting to measure an optical path length using a noncontact location measurement instrument after attaching the analysis device together, laser light is blocked by the reagent 602 carried and supported by the measurement spot 6015, thereby preventing measurement of the optical path length of the measurement spot.

Furthermore, when measuring an optical path length before the reagent is carried and supported, an accurate measurement of the optical path length is disadvantageously prevented from being obtained due to attaching variations not taken into consideration.

The present invention has been made to solve the conventional problems described above, and an object thereof is to provide an analysis device capable of accurately measuring an optical path length even when a reagent is carried and supported at a measurement spot during the manufacturing stage.

Means for Solving the Problems

An analysis device according to the present invention is an analysis device having a microchannel structure that transfers a sample liquid towards a measurement spot by centrifugal force and which is used to read a reactant at the measurement spot, the analysis device including: a separation cavity that separates the sample liquid into a solution component and a solid component using the centrifugal force; a first holding section to which a part of the solid component separated by the separation cavity is transferred and which holds the part of the solid component; and an overflow channel connected to a connecting channel that is provided between the first holding section and the separation cavity and which transfers the sample liquid in the separation cavity, the cross-sectional size of the overflow channel in the thickness direction thereof being smaller than the cross-sectional size of the connecting channel in the thickness direction thereof.

In addition, the width of the overflow channel at a bifurcation section of the overflow channel and the connecting channel in a direction that intersects with a flow direction of the overflow channel is wider than the width of the connecting channel in a direction that intersects with a flow direction of the connecting channel.

Furthermore, the cross-sectional size of the overflow channel in a thickness direction thereof is equal to or smaller than half of the cross-sectional size of the connecting channel in a thickness direction thereof.

An analysis apparatus according to the present invention is an analysis apparatus in which is set an analysis device having a separation cavity that separates the sample liquid into a solution component and a solid component using the centrifugal force, a first holding section to which a part of the solid component separated by the separation cavity is transferred and which holds the part of the solid component, and an overflow channel provided between the first holding section and the separation cavity and which is connected to a connecting channel that transfers the sample liquid in the separation cavity, the cross-sectional size of the overflow channel in the thickness direction thereof being smaller than the cross-sectional size of the connecting channel in the thickness direction thereof, the analysis apparatus including: a rotation driving unit that rotates the analysis device around an axial center; and an analysis unit that accesses and analyzes a reactant inside the analysis device transferred by the rotation driving unit, wherein the analysis apparatus is arranged such that the sample liquid can be separated into the solution component and the solid component by rotating and stopping the rotation driving unit and a portion of the solid component can be collected.

An analysis method according to the present invention includes: setting an analysis device having a separation cavity that separates the sample liquid into a solution component and a solid component using the centrifugal force, a first holding section to which a part of the solid component separated by the separation cavity is transferred and which holds the part of the solid component, and an overflow channel provided between the first holding section and the separation cavity and which is connected to a connecting channel that transfers the sample liquid in the separation cavity, the cross-sectional size of the overflow channel in the thickness direction thereof being smaller than the cross-sectional size of the connecting channel in the thickness direction thereof, onto a rotor having an axial center, and rotating the rotor to transfer the sample liquid applied to the analysis device by instillation to the separation cavity and performing centrifugal separation on the sample liquid; stopping the rotor to remove the solution component in the connecting channel from the separation cavity of the analysis device using the overflow channel and transferring the solid component to the first holding section; rotating the rotor and mixing the solid component in the first holding section with a diluted solution; and rotating the rotor and accessing a reactant at the measurement spot at a timing where the measurement spot exists at a reading position.

An analysis device according to the present invention is an analysis device having a microchannel structure that transfers a sample liquid towards a measurement spot by centrifugal force and which is used to read a reactant at the measurement spot, the analysis device including: a separation cavity that separates the sample liquid into a solution component and a solid component using the centrifugal force; a first holding section to which a part of the solid component separated by the separation cavity is transferred and which holds the part of the solid component; an overflow channel provided between the first holding section and the separation cavity and which is connected to a connecting channel that transfers the sample liquid in the separation cavity; and a capillary cavity formed inside the separation cavity so as to temporarily hold the separated solution component inside the separation cavity.

The analysis device further includes: a connecting channel communicating with an outermost circumferential position of the connecting channel and which has a siphon structure that is bent at a circumferentially inward position with respect to a liquid surface of the sample liquid held in the separation cavity; and a sample solution overflow cavity positioned circumferentially outwards from an outermost circumferential position of the connecting channel and which communicates with the separation cavity via the connecting channel.

In addition, the capillary cavity is formed on any one of the side surfaces in the separation cavity.

Furthermore, an end of the capillary cavity is formed from the liquid surface of the sample liquid up to an outer circumferential position so that the end of the capillary cavity is immersed in the sample liquid held in the separation cavity.

An analysis apparatus according to the present invention is an analysis apparatus in which is set an analysis device having a separation cavity that separates the sample liquid into a solution component and a solid component using the centrifugal force, a first holding section to which a part of the solid component separated by the separation cavity is transferred and which holds the part of the solid component, an overflow channel provided between the first holding section and the separation cavity and which is connected to a connecting channel that transfers the sample liquid in the separation cavity, and a capillary cavity formed inside the separation cavity so as to temporarily hold the separated solution component inside the separation cavity, the analysis apparatus including: a rotation driving unit that rotates the analysis device around an axial center; and an analysis unit that accesses and analyzes a reactant inside the analysis device based on a solution transferred by the rotation driving unit, wherein the analysis apparatus is arranged such that the sample liquid can be separated into the solution component and the solid component by rotating and stopping the rotation driving unit and a portion of the solid component can be collected.

An analysis method according to the present invention includes: setting an analysis device having a separation cavity that separates the sample liquid into a solution component and a solid component using the centrifugal force, a first holding section to which a part of the solid component separated by the separation cavity is transferred and which holds the part of the solid component, an overflow channel provided between the first holding section and the separation cavity and which is connected to a connecting channel that transfers the sample liquid in the separation cavity, and a capillary cavity formed inside the separation cavity so as to temporarily hold the separated solution component inside the separation cavity, onto a rotor having an axial center, rotating the rotor to transfer the sample liquid applied to the analysis device by instillation to the separation cavity and performing centrifugal separation on the sample liquid, stopping the rotor and holding the solution component of the sample liquid after centrifugal separation in the capillary cavity formed inside the separation cavity, removing the solution component among the solution component and the solid component of the sample liquid having flowed from the separation cavity to the connecting channel by the overflow channel that communicates with the connecting channel, and transferring the solid component to the first holding section; rotating the rotor and mixing the solid component in the first holding section with a diluted solution; and rotating the rotor and accessing a reactant at the measurement spot at a timing where the measurement spot exists at a reading position.

An analysis method according to the present invention is an analysis method using an analysis device having a microchannel structure that transfers a sample liquid towards a measurement spot by centrifugal force and which is used for reading in which a reactant at the measurement spot is accessed, wherein an immunoreaction is caused between the sample liquid and a latex reagent sensitized by an antibody that specifically reacts with a particular component in the sample liquid, a reaction liquid is created by performing an agglutination process using an agglutination reagent, and accessing the reaction liquid during the rotation of the analysis device to perform measurement.

In addition, the average particle size of the latex reagent is equal to or smaller than 0.3 μm.

Furthermore, the mixing ratio of the antibody sensitized by the latex reagent and an antigen inside the agglutination reagent is antigen-excessive.

Moreover, the mean value of the particle size of the agglutinated substance within three minutes of the reaction between the latex reagent and the agglutination reagent is equal to or less than 700 nm.

In addition, the antibody is a monoclonal antibody produced from accession number FERM BP-10795, International Patent Organism Depositary, National Institute of Advanced Industrial Science and Technology.

Furthermore, the mean value of the particle size of the agglutinated substance within three minutes of the reaction between the latex reagent and the agglutination reagent is equal to or less than 700 nm, and the centrifugal force acting on the agglutinated substance during measurement is equal to or smaller than 200 G.

Moreover, the immunoreaction involves having a latex reagent react to a mixed solution that combines the sample liquid with a diluent measured inside the analysis device.

In addition, the immunoreaction involves having a latex reagent react to a mixed solution that combines the sample liquid with a diluent measured inside the analysis device, the sample liquid is blood, and after condensing a blood cell component in the blood by centrifugal force, a constant amount of blood containing the condensed blood cell component is collected to be mixed with the diluent.

Furthermore, the immunoreaction involves having a latex reagent react to a mixed solution that combines the sample liquid with a diluent measured inside the analysis device, and the reaction with the latex reagent is caused after further measuring the mixed solution.

Moreover, the sample liquid is denaturized by a denaturing reagent so as to ensure that an immunoreaction occurs between a specific component in the sample liquid and the latex reagent.

An analysis device according to the present invention is an analysis device having an operation chamber into which a sample liquid flows and which agitates the sample liquid in the operation chamber using acceleration during a swinging operation, wherein the shape of an inner circumferential·wall inside the operation chamber is formed by an inclined wall surface that narrows from the inner circumferential side towards an outermost circumferential position during a swinging operation.

In addition, the outermost circumferential position of the inner circumferential wall of the operation chamber has an arc-like shape.

Furthermore, the inner circumferential surface in the operation chamber has been subjected to water-repelling treatment.

Moreover, a reagent containing a surfactant has been provided in the operation chamber.

An analysis apparatus according to the present invention is an analysis apparatus in which is set an analysis device whose shape of an inner circumferential wall inside the operation chamber into which a sample liquid flows is formed by an inclined wall surface that narrows from the inner circumferential side towards an outermost circumferential position during a swinging operation, the analysis apparatus including: a rotor having a rotation axial center and which holds the analysis device; a rotation driving unit that rotates the rotor so that centrifugal force acts on the analysis device; and an analysis unit that accesses and measures a liquid inside the operation chamber of the analysis device.

In addition, the rotation driving unit generates a centrifugal force that is greater than surface tension acting on the sample liquid held in the analysis device.

An analysis device according to the present invention is an analysis device to be used in reading that involves optically accessing a mixed liquid of a sample liquid transferred to a measurement spot and a reagent set at the measurement spot, wherein a reagent holding region that holds the reagent and an analysis region adjacent to the reagent holding region and into which the mixed liquid flows are provided inside a single measurement spot.

In addition, a depression and a protrusion are formed on at least one of a bottom surface and a top surface of the single measurement spot, wherein one of the depression and the protrusion is assumed to be the reagent holding region and the other of the depression and the protrusion is assumed to be the analysis region.

Furthermore, the reagent holding region and the analysis region having the same level are formed on at least one of the bottom surface and the top surface of the single measurement spot, wherein a protrusion or a depression is formed on the boundary between the reagent holding region and the analysis region.

Moreover, hydrophobic treatment has been performed on the analysis region.

In addition, a plurality of reagent holding regions for holding reagents of different types is provided within the single measurement spot.

An analysis apparatus according to the present invention includes: a rotor retaining an analysis device having, in a single measurement spot, a reagent holding region that holds a reagent and an analysis region adjacent to the reagent holding region and into which a mixed liquid flows are provided, and which has a rotation axial center; a rotation driving unit that rotates the rotor so that centrifugal force acts on the analysis device; and an analysis unit that optically accesses and measures a liquid inside an operation chamber of the analysis device.

An analysis device according to the present invention is an analysis device having a microchannel structure that transfers a sample liquid towards a measurement spot by centrifugal force and which is used for reading involving accessing a sample at the measurement spot, wherein a channel threshold is provided at the measurement spot where the sample liquid is held or at an overflow cavity that holds a surplus portion at a position circumferentially inwards with respect to a rotation upon generation of the centrifugal force from a liquid surface of the held sample liquid so as to limit the cross-sectional size of the measurement spot or the overflow cavity in the thickness direction to the magnitude of the action of a capillary force.

An analysis device according to the present invention is an analysis device having a microchannel structure that transfers a sample liquid towards a measurement spot by centrifugal force and which is used for reading involving accessing a sample at the measurement spot, wherein the measurement spot where the sample liquid is held or an overflow cavity that holds a surplus portion is formed such that the cross-sectional size in the thickness direction of an outer circumferential portion of a rotation upon generation of the centrifugal force is smaller than the cross-sectional size in the thickness direction of an inner circumferential portion of the rotation upon generation of the centrifugal force and is equal to the magnitude of the action of a capillary force.

In addition, an air duct communicating with the air side is provided in an area on which capillary force does not act and which is on an inner circumferential side of the threshold.

Furthermore, an air duct communicating with the air side is provided in an area on which capillary force does not act and which is on an inner circumferential side of a capillary area.

An analysis apparatus according to the present invention is an analysis apparatus in which is set an analysis device having a microchannel structure that transfers a sample liquid towards a measurement spot by centrifugal force, the analysis device provided with a channel threshold at the measurement spot or at an overflow cavity that holds a surplus portion at a position circumferentially inwards with respect to a rotation upon generation of the centrifugal force from a liquid surface of the held sample liquid so as to limit the cross-sectional size of the measurement spot or the overflow cavity in the thickness direction to the magnitude of the action of a capillary force, the analysis apparatus including: a rotation driving unit that rotates the analysis device around an axial center; and an analysis unit that accesses and analyzes a sample inside the analysis device based on a solution transferred by the rotation driving unit, wherein the analysis apparatus is arranged such that the sample liquid can be transferred to the measurement spot and the overflow cavity by a rotation of the rotation driving unit.

An analysis method according to the present invention includes: rotating an analysis device having a microchannel structure that transfers a sample liquid towards a measurement spot by centrifugal force, the analysis device provided with a channel threshold at the measurement spot or at an overflow cavity that holds a surplus portion at a position circumferentially inwards with respect to a rotation upon generation of the centrifugal force from a liquid surface of the held sample liquid so as to limit the cross-sectional size of the measurement spot or the overflow cavity in the thickness direction to the magnitude of the action of a capillary force to transfer at least a portion of the sample liquid applied to the analysis device by instillation to the measurement spot and to transfer the remainder of the sample liquid to the overflow cavity; mixing the transferred sample liquid with a reagent; and rotating the rotor and accessing the sample at the measurement spot at a timing where the measurement spot exists at a reading position.

Advantages of the Invention

According to the configuration described above, a predetermined amount of a solid component can be accurately transferred from a separation cavity to a measurement channel and the measurement accuracy of an analysis device can be improved.

In addition, according to the configuration described above, a small amount of sample liquid and a reagent can be mixed and agitated, thereby enabling further downsizing of an analysis device.

Furthermore, according to the configuration described above, analysis of hemoglobin and hemoglobin A1c components can be automatically performed in a simple and prompt manner.

Moreover, according to the configuration described above, by providing, in a single measurement spot, a reagent holding region and an analysis region into which a mixed liquid flows separate from the reagent holding region, the analysis region can be measured so as to measure an optical path length before sending a sample liquid into the measurement spot. A mixed liquid obtained when a sample liquid is sent into the measurement spot and reacts with a reagent in the reagent holding region can then be accepted into the analysis region to be analyzed.

In addition, according to the configuration described above, a sample liquid held at a measurement spot or in an overflow cavity can be trapped using capillary force so as to suppress outflow from an air duct. As a result, the risk of an operator being involved in a contamination accident can be reduced.

BEST MODE FOR CARRYING OUT THE INVENTION

First Embodiment

An embodiment of an analysis device, and an analysis apparatus and an analysis method using the same according to the present invention will now be described with reference to FIGS. 1 to 23A and 23B.

Figure 1:
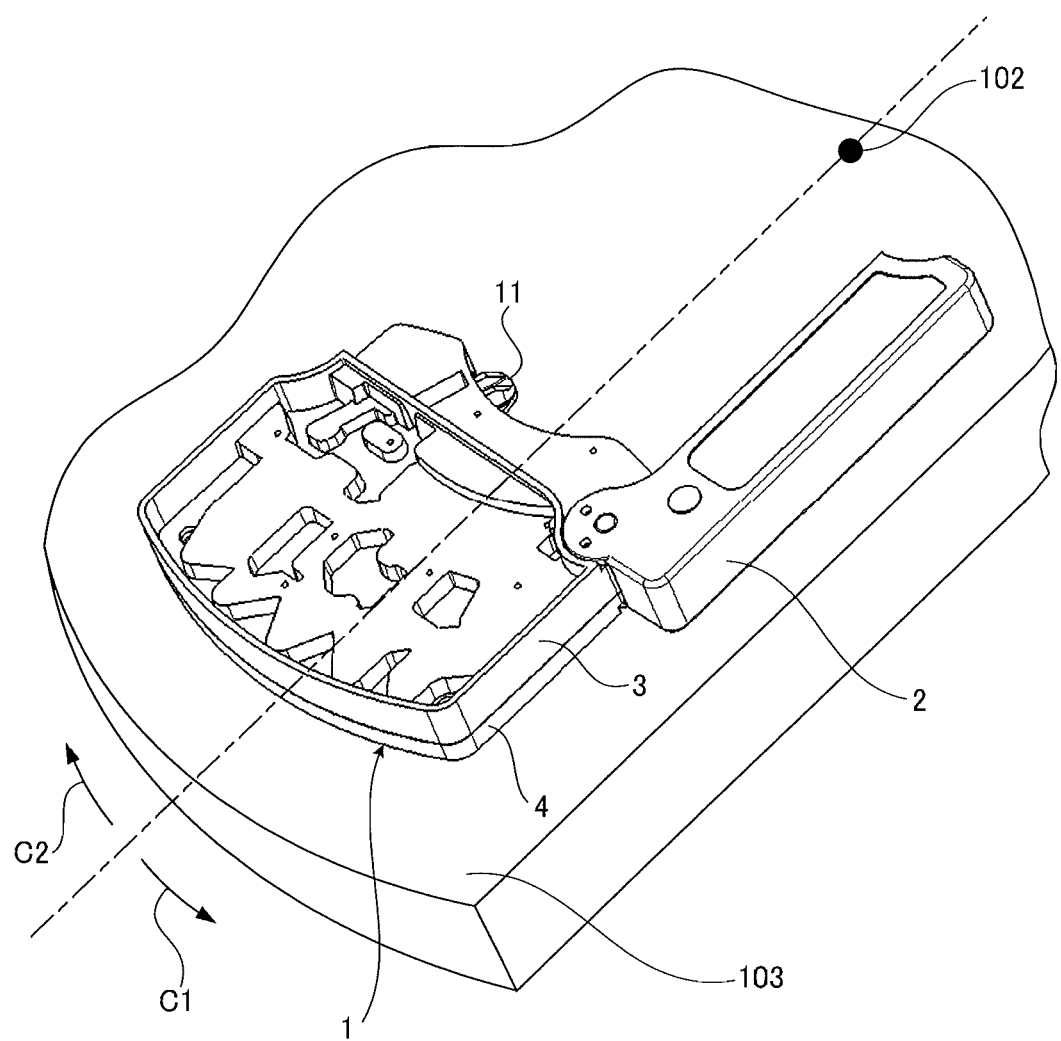
FIG. 1 is a perspective view of a substantial part of a state where an analysis device is set in an analysis apparatus according to an embodiment of the present invention.
Figure 2:
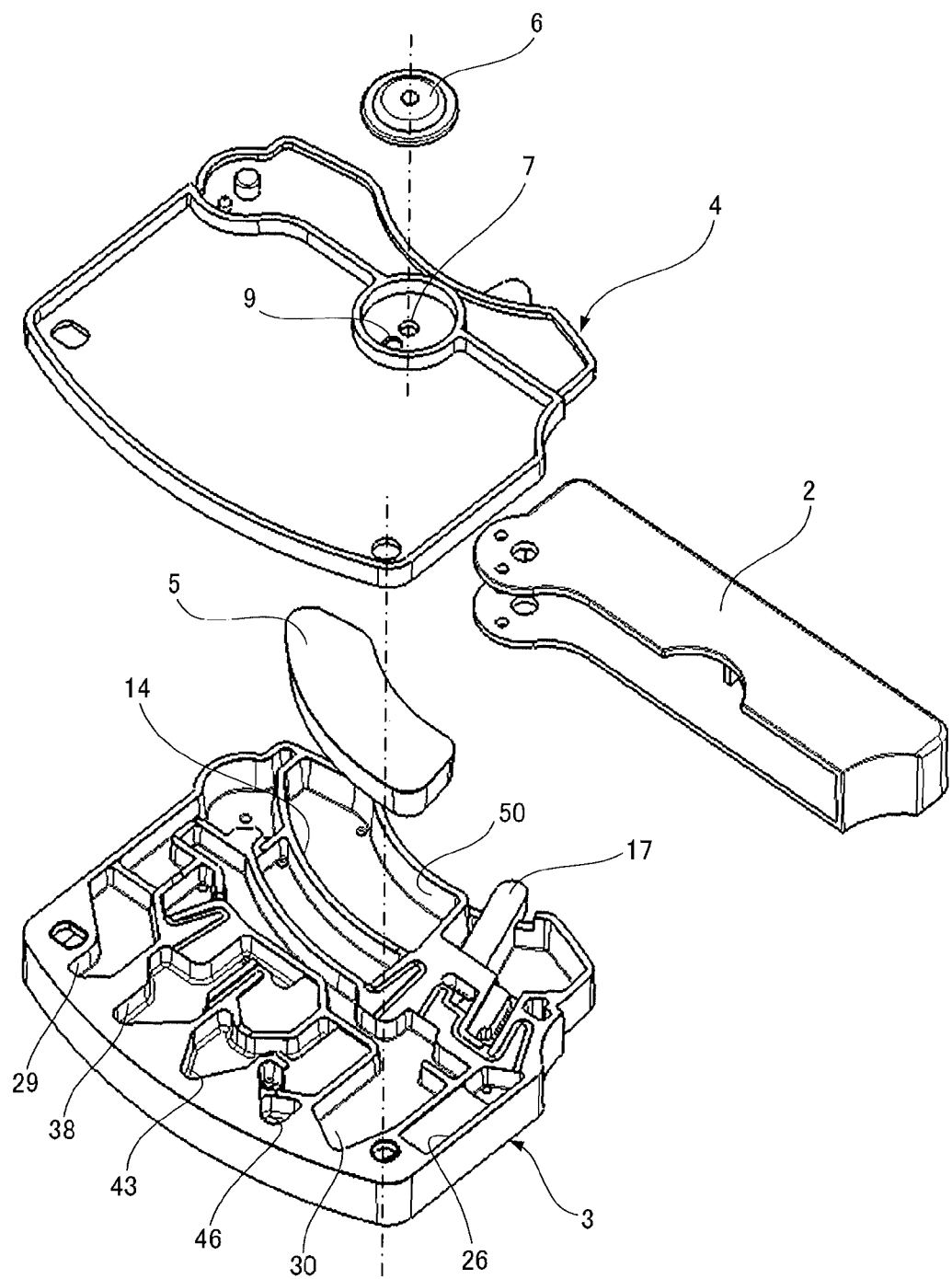
FIG. 2 is an exploded perspective view of an analysis device according to an embodiment of the present invention.

FIG. 1 illustrates a state where an analysis device 1 according to an embodiment of the present invention is set on a rotor 103 of an analysis apparatus, and FIG. 2 illustrates an exploded state where a face of the analysis device 1 in contact with the rotor 103 is turned upward.

The analysis device 1 is made up of five parts, namely: a protective cap 2 for preventing a sample liquid from scattering; a base substrate 3 on which is formed a microchannel structure having minute irregular shapes on a surface thereof; a cover substrate 4 that covers the surface of the base substrate 3; a diluent receiving cavity 5 holding a diluent; and a opening button 6 that discharges the diluent inside the diluent receiving cavity 5 set in one depression 50 among several depressions formed on an upper face of the base substrate 3.

The base substrate 3 and the cover substrate 4 are bonded in a state where the diluent receiving cavity 5 and the like are internally set, whereby the protective cap 2 is attached to the base substrate 3 and the cover substrate 4 in the bonded state. In addition, the opening button 6 is bonded centered around a position of an opening hole 7 formed on the cover substrate 4.

By covering the openings of the several depressions formed on the upper face of the base substrate 3 with the cover substrate 4, a plurality of receiving areas to be described later (equivalent to the measurement spots to be described later) and channels interconnecting the receiving areas are formed (refer to FIG. 2). Among the receiving areas, those required hold, in advance, reagents necessary for performing various analyses.

The analysis device 1 is capable of collecting a sample liquid such as blood and other solutions from an inlet 11, and by closing the protective cap 2 and setting the analysis device 1 on the rotor 103 of the analysis apparatus, a component analysis of the sample liquid can be performed. Reference numeral 102 denotes an axial center during rotation of the rotor 103.

The analysis device 1 is arranged so as to internally transfer a sample liquid taken inside from the inlet 11 using a centrifugal force that is generated by rotating the analysis device 1 around the axial center 102 positioned circumferentially inward from the inlet 11 and a capillary force of a capillary channel provided inside the analysis device 1. The protective cap 2 is attached in order to prevent the sample liquid adherent to the vicinity of the inlet 11 from scattering to the outside due to centrifugal force during analysis.

Resin material with low material cost and superior mass productivity is desirably used for the parts that make up the analysis device 1 according to the present invention. Since the aforementioned analysis apparatus analyzes sample liquids using an optical measurement method which measures light transmitted through the analysis device 1, a resin with a high transparency such as PC, PMMA, AS, MS, and the like is desirably used as the materials for the base substrate 3 and the cover substrate 4.

In addition, since it is required that a diluent be sealed inside the diluent receiving cavity 5 over a long period of time, a crystalline resin with a low moisture permeability such as PP and PE is desirably used as the material of the diluent receiving cavity 5. Since the opening button 6 is deformingly used when opening the diluent receiving cavity 5, a crystalline resin such as PP having a high elastic modulus is desirable for the opening button 6. As for the material of the protective cap 2, any material with good moldability shall suffice. Inexpensive resins such as PP and PE are desirable.

The bonding between the base substrate 3 and the cover substrate 4 is desirably performed using a method that is unlikely to affect the reaction activity of reagents held in the receiving areas. Desirable methods include ultrasonic welding and laser welding which are less likely to produce reactive gases or solvents during bonding.

In addition, a portion of a minute gap between the base substrate 3 and the cover substrate 4 formed by the bonding of both substrates 3 and 4 for transferring a solution by capillary force is subjected to a hydrophilic treatment to enhance capillary force. Specifically, a hydrophilic treatment using a hydrophilic polymer or a surfactant is performed. In this case, hydrophilicity refers to a contact angle of less than 90 degrees with respect to water, and more favorably, a contact angle of less than 40 degrees.

FIGS. 3 to 6A, 6B, and 6C illustrate an analysis apparatus on which the analysis device 1 is to be set.

Figure 3:
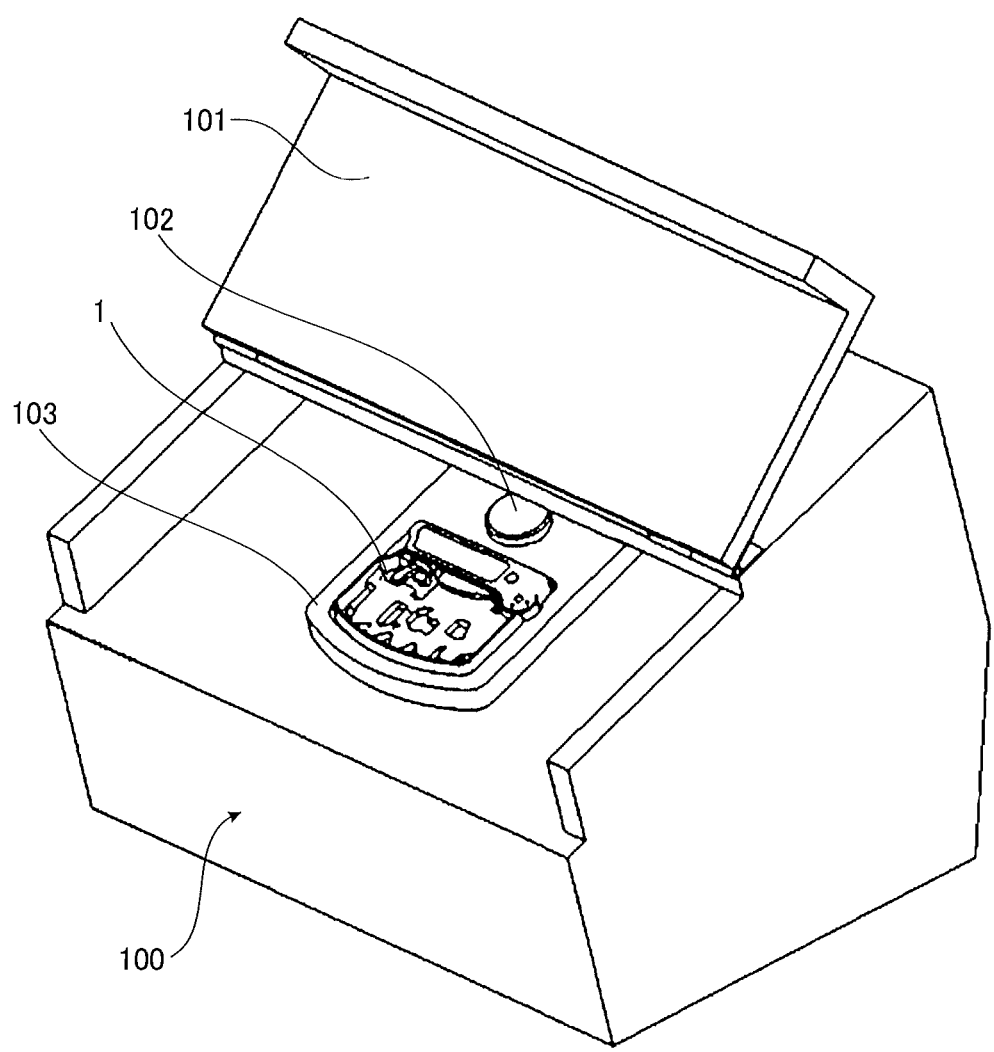
FIG. 3 is an external view of an analysis apparatus according to an embodiment of the present invention.

In FIG. 3, the analysis device 1 is mounted on the rotor 103 that rotates around the axial center 102 of the analysis apparatus main body 100 with the side of the cover substrate 4 among the base substrate 3 and the cover substrate 4 facing down. Analysis is performed with a cover 101 closed.

Figure 4:
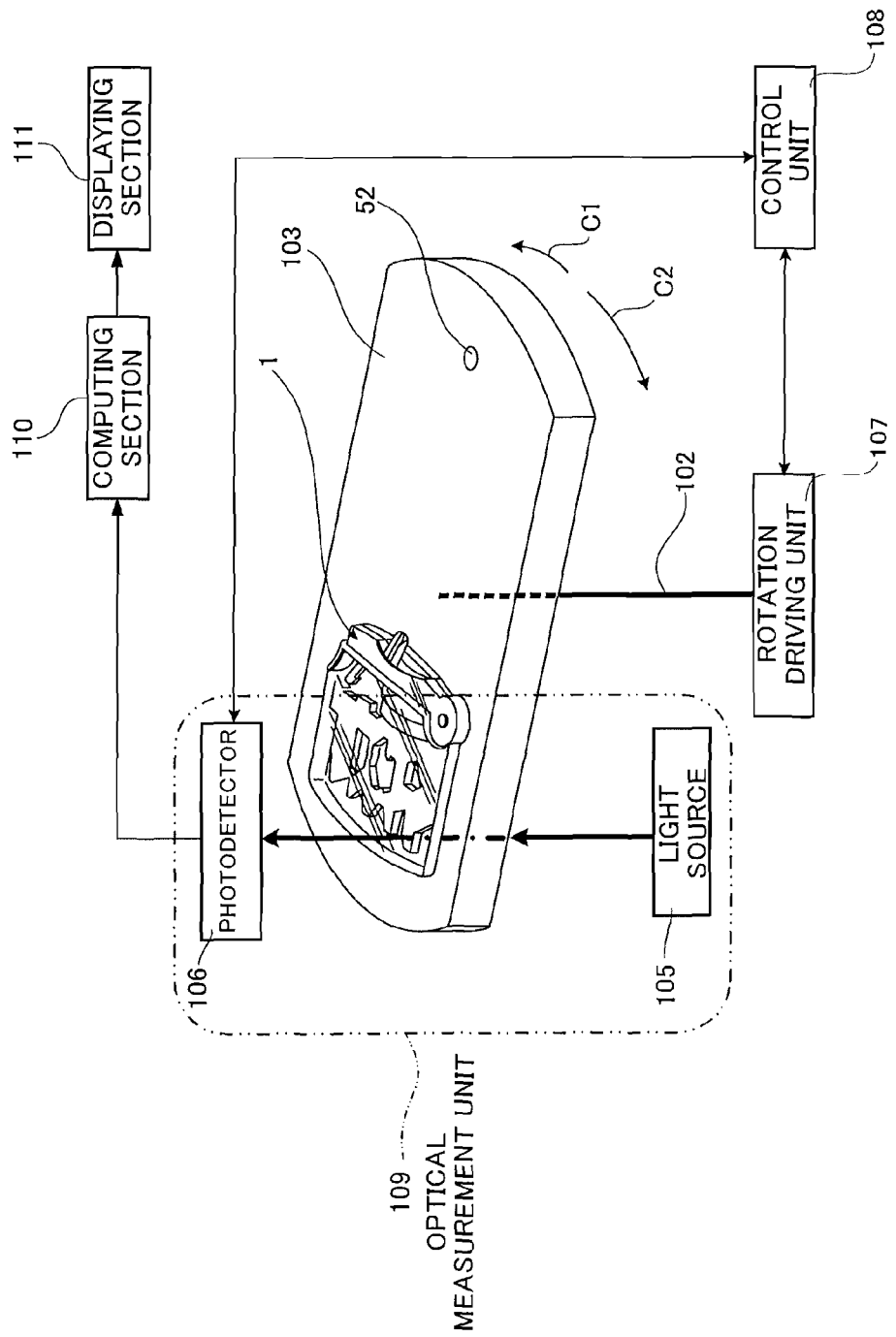
FIG. 4 is a configuration diagram of an analysis apparatus according to an embodiment of the present invention.
Figure 5:
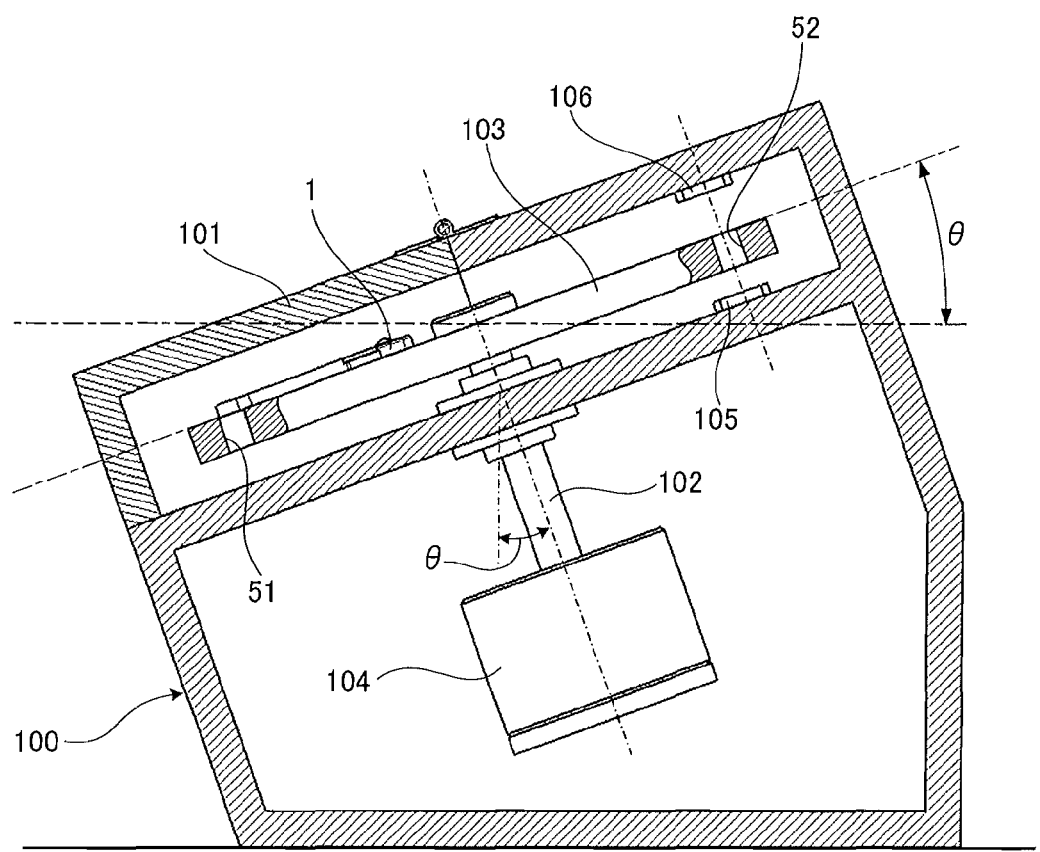
FIG. 5 is a cross-sectional view of an analysis apparatus according to an embodiment of the present invention.

As illustrated in FIGS. 4 and 5, the analysis apparatus main body 100 is made up of: a rotation driving unit 107 for rotating the rotor 103; an optical measurement unit 109 that optically measures a solution in the analysis device 1; a control unit 108 that controls the rotational speed and rotational direction of the rotor 103, the measurement timing of the optical measurement unit, and the like; a computing section 110 that processes a signal obtained by the optical measurement unit 109 and computes a measurement result; and a displaying section 111 that displays the result obtained by the computing section 110.

In addition to rotating the analysis device 1 around the axial center 102 via the rotor 103 in any direction at a predetermined rotational speed, the rotation driving unit 107 is arranged so as to be capable of causing the analysis device 1 to perform a left-right reciprocating movement centered around the axial center 102 at a predetermined stop position and at a predetermined amplitude range and frequency so as to swing the analysis device 1. In this case, a motor 104 is used as the rotation driving unit 107 to rotate the rotor 103 around the axial center 102. The axial center 102 is rotatably mounted inclined by an inclination angle of exactly 0 with respect to a central predetermined position on the axial center 102.

While an arrangement is provided in which rotational operations and swinging operations of the analysis device 1 is performed by a single rotation driving unit 107, a driving unit for swinging operations may alternatively be separately provided in order to reduce the load on the rotation driving unit 107. Specifically, by bringing a vibration-applying unit such as a vibration motor prepared separate from the motor 104 into direct or indirect contact with the analysis device 1 set on the rotor 103, a swinging operation of the analysis device 1 is caused so as to apply inertial force to the solution in the analysis device 1.

The optical measurement unit 109 includes: a light source 105 that irradiates light to a measurement section of the analysis device 1; and a photodetector 106 that detects a light intensity of transmitted light having passed through the analysis device 1 among the light irradiated from the light source 105. In a case where the rotor 103 is made of a material with poor translucency or a nontranslucent material, holes 51 and 52 are drilled at a mounting position of the analysis device 1 on the rotor 103.

In this case, a light source capable of switching wavelengths of outgoing light is used as the light source 105, and a photodetector capable of detecting light of any wavelength of the outgoing light from the light source 105 is used as the photodetector 106.

Alternatively, a plurality of pairs of the light source 105 and the photodetector 106 may be provided depending on the types of wavelengths necessary for measurement.

Furthermore, the analysis apparatus main body 100 may alternatively include an opening unit that automatically opens the diluent receiving cavity 5 inside the analysis device 1 or, more specifically, a mechanism in which an arm that moves the rotor 103 up and down so as to enable the opening button 6 of the analysis device 1 set on the rotor 103 to be operated, whereby the opening button 6 is to be pressed upward by the arm.

As illustrated in FIG. 5, the rotor 103 is attached on the inclined axial center 102 and is therefore inclined by an inclination angle of exactly 0 with respect to a horizontal line. The rotor 103 is capable of controlling the direction of gravity acting on the solution inside the analysis device 1 in accordance with the rotation stop position of the analysis device 1.

Figure 6A:
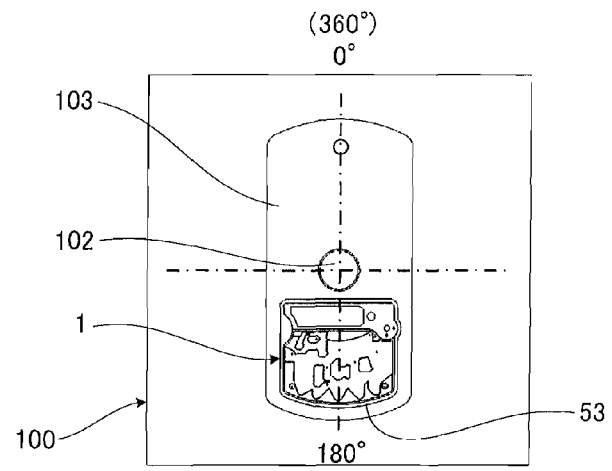
FIG. 6A is a diagram illustrating a rotation stop position of an analysis device according to an embodiment of the present invention.

Specifically, when the analysis device 1 is stopped at a position illustrated in FIG. 6A (a position near 180 degrees when directly above is expressed as 0 degrees (360 degrees)), since the lower side of the analysis device 1 faces downward as seen from the front, the solution inside the analysis device 1 receives gravity in an outer circumferential direction (downward).

Figure 6B:
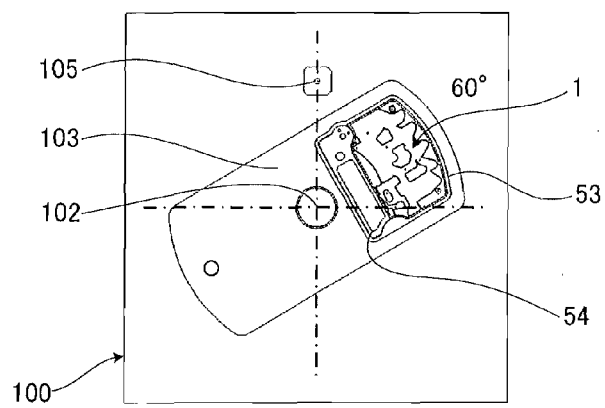
FIG. 6B is a diagram illustrating a rotation stop position of an analysis device according to an embodiment of the present invention.
Figure 6C:
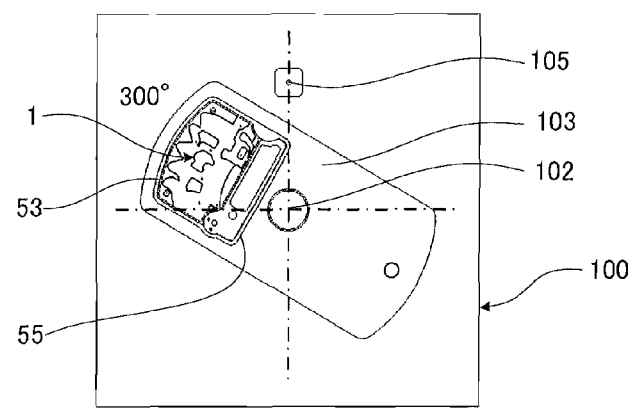
FIG. 6C is a diagram illustrating a rotation stop position of an analysis device according to an embodiment of the present invention.

In addition, when the analysis device 1 is stopped at a position near 60 degrees as illustrated in FIG. 6B, since a top left side 54 of the analysis device 1 faces downward as seen from the front, the solution inside the analysis device 1 receives gravity in a left upward direction. Similarly, at a position near 300 degrees as illustrated in FIG. 6C, since a top right side 55 of the analysis device 1 faces downward as seen from the front, the solution inside the analysis device 1 receives gravity in a right upward direction.

As shown, inclining the axial center 102 and stopping the analysis device 1 at any position can be utilized as a driving force for transferring the solution inside the analysis device 1 in a predetermined direction.

The magnitude of gravity acting on the solution inside the analysis device 1 can be set by adjusting the inclination angle θ of the axial center 102, and is desirably set depending on a relationship between the amount of liquid to be transferred and the force in which the liquid adheres to a wall surface in the analysis device 1.

The inclination angle θ desirably falls within a range from 10 degrees to 45 degrees. When the inclination angle θ is smaller than 10 degrees, there is a risk that gravity acting on the solution may be too small and a driving force necessary for transfer may not be obtained. When the inclination angle θ is greater than 45 degrees, there is a risk that the load on the axial center 102 may increase or the solution transferred by centrifugal force may move voluntarily due to its own weight and become uncontrollable.

With the analysis apparatus main body 100 according to the present embodiment, the inclination angle θ is fixed at any angle within a range from 10 degrees to 45 degrees and the motor 104 that is the rotation driving unit 107, the light source 105, and the photodetector 106 are also attached parallel to the inclined axial center 102. Alternatively, by arranging the inclination angle θ to be adjustable to any angle and the angles of the motor 104, the light source 105, and the photodetector 106 to be altered so as to follow the inclination angle θ, an optimum inclination angle can be set according to specifications of the analysis device 1 and a transfer processes in the analysis device 1. In the case of a configuration in which the inclination angle θ is adjustable to any angle, the inclination angle θ desirably falls within a range from 0 degrees to 45 degrees. When it is desirable to remove the influence of gravity, the rotor 103 can be rotated while setting the inclination angle to 0 degrees or, in other words, setting the rotor 103 so as to be horizontal.

FIGS. 7A and 7B to FIG. 13 illustrate details of the analysis device 1.

Figure 7A:
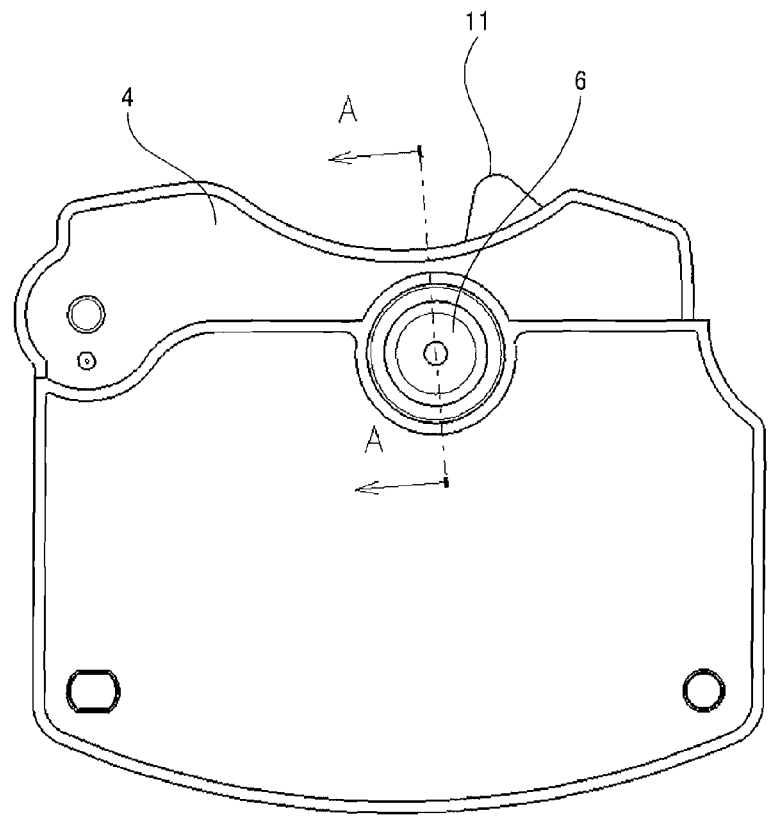
FIG. 7A is a plan view of an diluting unit opening section of an analysis device according to an embodiment of the present invention.
Figure 7B:
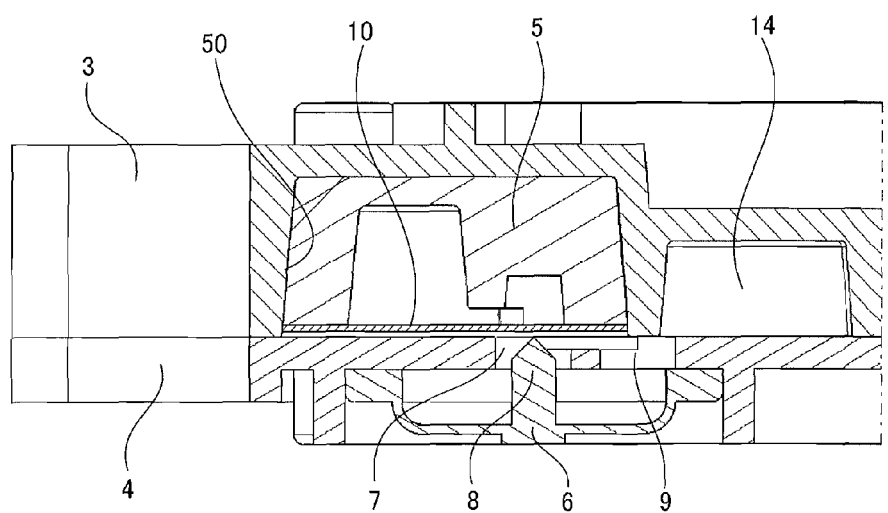
FIG. 7B is a cross-sectional view of an diluting unit opening section of an analysis device according to an embodiment of the present invention.

FIGS. 7A and 7B illustrate a diluting unit opening section of the analysis device 1.

FIG. 7A is a plan view illustrating a mounting position of the opening button 6. FIG. 7B is a cross-sectional view taken along A-A in FIG. 7A.

With respect to opening and discharge of the diluent receiving cavity 5, by pushing up a center portion of the opening button 6 bonded to the cover substrate 4 as illustrated in FIG. 7B from below, an aluminum seal 10 affixed to the surface of the diluent receiving cavity 5 is penetrated by a pin 8, thereby opening the diluent receiving cavity 5. In addition, when the analysis device 1 is rotated in a state where the diluent receiving cavity 5 is opened, a diluent inside the diluent receiving cavity 5 is discharged to a diluent quantitative cavity 14 as a second holding section via a space formed between a opening hole 7 and a discharge hole 9 (a discharge groove formed between the base substrate 3 and the cover substrate 4, and a space formed between the cover substrate 4 and the opening button 6).

Figure 8A:
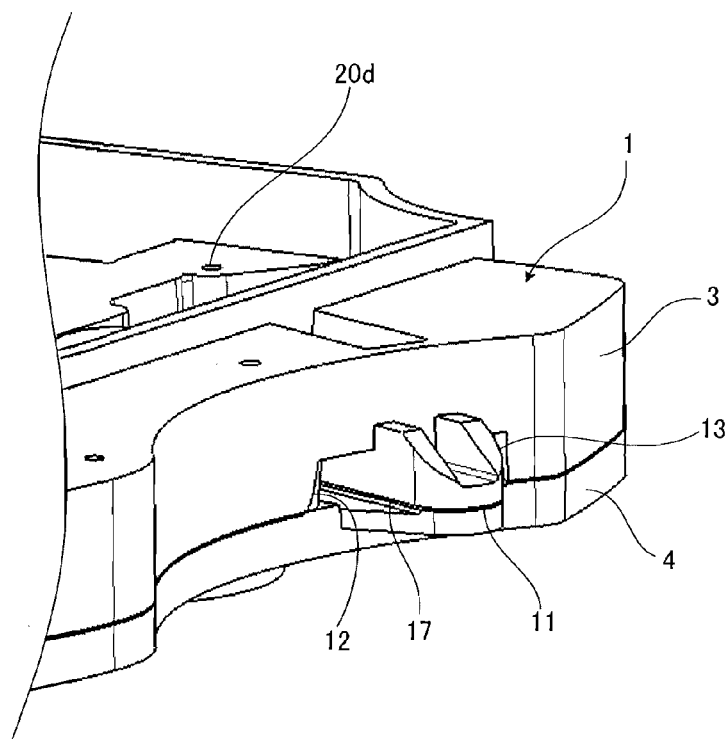
FIG. 8A is an enlarged perspective view of a periphery of an inlet of an analysis device according to an embodiment of the present invention.
Figure 8B:
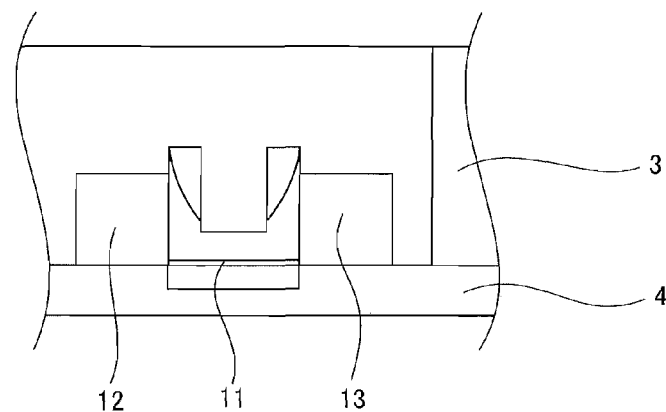
FIG. 8B is a front view of a periphery of an inlet of an analysis device according to an embodiment of the present invention.
Figure 9:
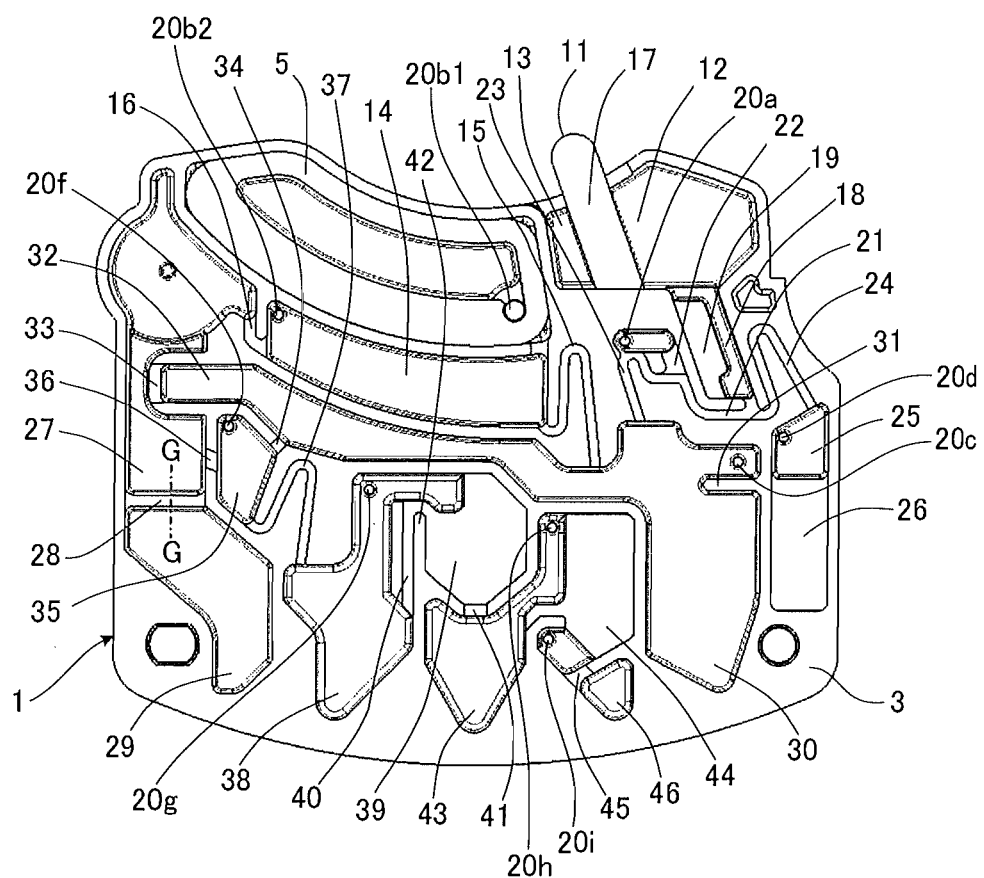
FIG. 9 is a plan view illustrating a microchannel structure of an analysis device according to an embodiment of the present invention.

FIG. 8A is an enlarged perspective view of a periphery of an inlet of the analysis device 1, and FIG. 8B is a front view of the same. FIG. 9 is a plan view of a junction plane between the base substrate 3 and the cover substrate 4 illustrated in FIG. 2. Reference characters 20a, 20b1, 20b2, 20c, 20d, 20e, 20f, 20g, 20h, and 20i denote air ducts.

Since the analysis device 1 is capable of suctioning a sample liquid by the capillary force of a sample receiving cavity 17 formed inside by having the sample liquid deposited on the inlet 11, blood can be directly collected from a fingertip or the like. The inlet 11 is shaped so as to protrude in the direction of the axial center 102 from a side face of the main body of the analysis device 1. Therefore, when a finger or the like comes into contact with a location other than the inlet 11 and blood adheres to that location, the inlet 11 has an effect of preventing adhered blood from scattering to the outside during analysis.

In addition, cavities 12 and 13 whose cross-sectional dimensions in the thickness direction are greater than that of the sample receiving cavity 17 and which communicate with the air are provided on a side face of the sample receiving cavity 17. By providing the cavities 12 and 13, a sample liquid flowing through the sample receiving cavity 17 is filled as a capillary flow whose central portion precedingly flows instead of a capillary flow whose lateral portion precedingly flows. Therefore, even when filling is performed in a plurality of batches, flowing takes place such that the respective central portions of the sample liquid held in the sample receiving cavity 17 and a subsequently collected sample liquid precedingly come into contact with each other and are filled while the air inside the sample receiving cavity 17 is discharged through the side-face cavities 12 and 13. Consequently, even when the amount of sample liquid to be deposited to the inlet 11 becomes deficient during collection or when a fingertip detaches from the inlet 11 during collection, collection can be performed as many times as required until collection into the sample receiving cavity 17 is completed. While the cross-sectional dimension of the sample receiving cavity 17 in the thickness direction is set within 50 to 300 μm and the cross-sectional dimensions of the cavities 12 and 13 in the thickness direction are set within 1000 to 3000 in this case, no particular restrictions on dimensions need be applied as long as sample liquid can be collected by the sample receiving cavity 17 by capillary force and the sample liquid is not transferred through the cavities 12 and 13 by capillary force.

Figure 10:
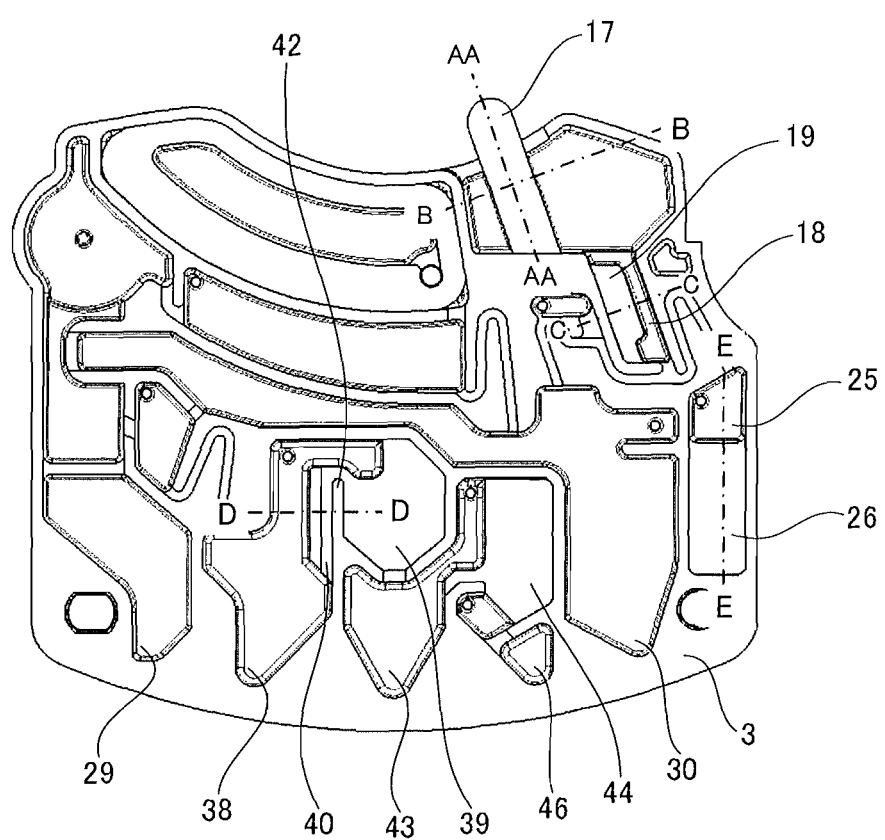
FIG. 10 is a plan view illustrating a cross-sectional position of an analysis device according to an embodiment of the present invention.

FIGS. 11A to 11E are enlarged views of cross sections of the respective locations of AA-AA, B-B, C-C, D-D, and E-E illustrated in FIG. 10. A hydrophilically treated position 56 subjected to hydrophilic treatment is indicated by hatching in FIG. 12.

Next, the microchannel configuration of the analysis device and a solution transfer process according to the first embodiment of the present invention will be described in detail.

Figure 13:
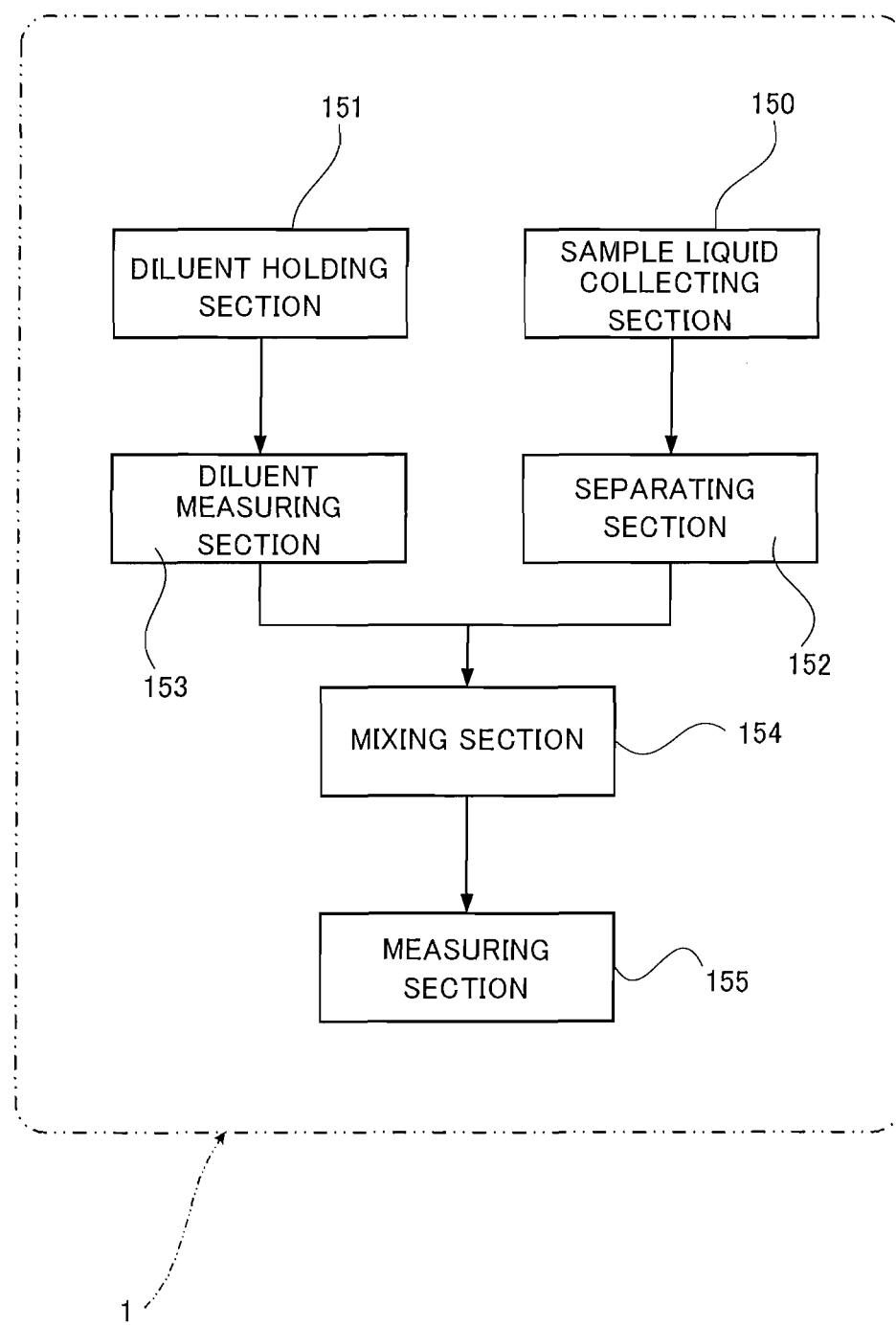
FIG. 13 is a configuration diagram of an analysis device according to an embodiment of the present invention.

FIG. 13 is a block diagram displaying a structure of the analysis device 1. Formed inside the analysis device 1 are: a sample liquid collecting section 150 that collects a sample liquid; a diluent holding section 151 that holds a diluent for diluting the sample liquid; a separating section 152 that holds a sample liquid transferred from the sample liquid collecting section 150 and, after centrifugally separating the sample liquid into a solution component and a solid component, collects a sample liquid containing a predetermined amount of the solid component; a diluent measuring section 153 that measures a diluent transferred from the diluent holding section 151; a mixing section 154 that holds a sample liquid transferred from the separating section 152 and a diluent transferred from the diluent measuring section 153 and, after internally mixing the sample liquid and the diluent, measures a diluted solution to an amount necessary for analysis; and a measuring section 155 that causes the diluted solution transferred from the mixing section 154 to react with an analytical reagent and measures the same.

The sample liquid collecting section 150 is made up of: the inlet 11 that collects a sample liquid as illustrated in FIG. 9; the sample receiving cavity 17 that collects the sample liquid through the inlet 11 by capillary force and holds just a predetermined amount of the sample liquid; and the cavities 12 and 13 which discharge air inside the sample receiving cavity 17 during the collection of the sample liquid.

The diluent holding section 151 holds a diluent inside the diluent receiving cavity 5 as illustrated in FIG. 9. The diluent is developed by an opening operation described earlier with reference to FIG. 7B.

The separating section 152 is made up of: a separation cavity 18 formed on the underside of the sample liquid collecting section 150 so as to communicate with the sample receiving cavity 17 via the cavity 12 as illustrated in FIG. 9 and which holds a sample liquid transferred from the sample receiving cavity 17 by centrifugal force and separates the sample liquid by centrifugal force into a solution component and a solid component; a higher specific gravity component quantitative cavity 23 formed between the separation cavity 18 and the diluent measuring section 153 as a first holding section that holds a transferred portion of the solid component separated by the separation cavity 18; a connecting channel 21 that connects the higher specific gravity component quantitative cavity 23 and the separation cavity 18 and transfers the sample liquid in the separation cavity 18; a sample solution overflow cavity 22 formed between the separation cavity 18 and the diluent measuring section 153 as an overflow channel that preferentially holds the solution component of the sample liquid separated in the connecting channel 21 and causes only the solid component to be transferred to the higher specific gravity component quantitative cavity 23; a capillary cavity 19 formed in the separation cavity 18 so as to suppress the separated solution component in the separation cavity 18 from being transferred to the higher specific gravity component quantitative cavity 23; a connecting channel 24 formed on the opposite side of the higher specific gravity component quantitative cavity 23 with respect to the separation cavity 18 and which discharges sample liquids in the separation cavity 18, the connecting channel 21, and the sample solution overflow cavity 22 not required by analysis; and sample solution overflow cavities 25 and 26 which hold unnecessary sample liquid transferred via the connecting channel 24.

Figure 11A:
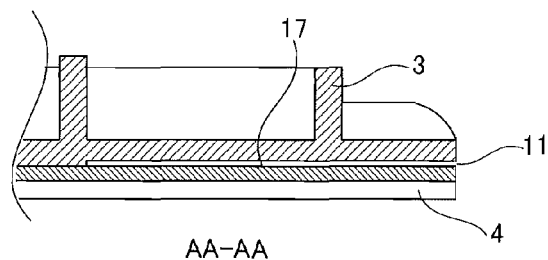
FIG. 11A is a cross-sectional view of respective parts of an analysis device according to an embodiment of the present invention.
Figure 11B:
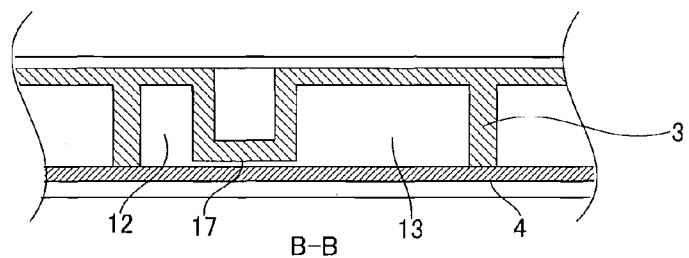
FIG. 11B is a cross-sectional view of respective parts of an analysis device according to an embodiment of the present invention.
Figure 11C:
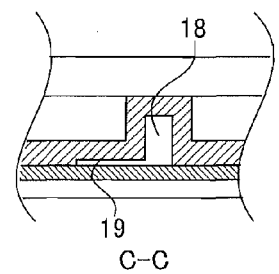
FIG. 11C is a cross-sectional view of respective parts of an analysis device according to an embodiment of the present invention.
Figure 11D:
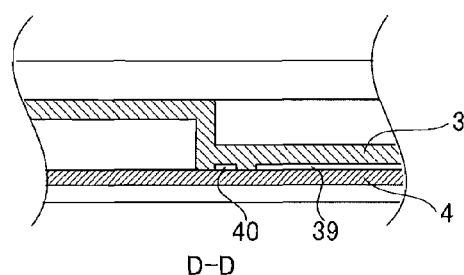
FIG. 11D is a cross-sectional view of respective parts of an analysis device according to an embodiment of the present invention.
Figure 11E:
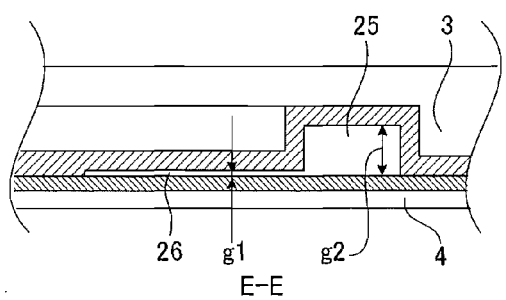
FIG. 11E is a cross-sectional view of respective parts of an analysis device according to an embodiment of the present invention.
Figure 12:
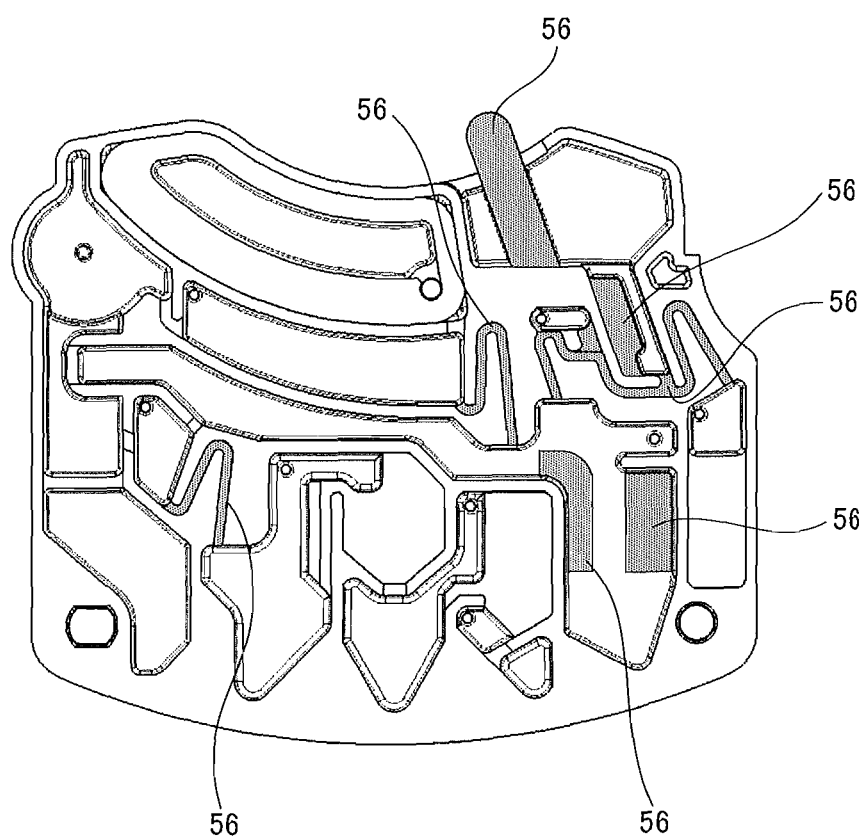
FIG. 12 is a plan view illustrating a hydrophilic treatment position of an analysis device according to an embodiment of the present invention.

As illustrated in FIG. 11E that is an enlarged view of a cross section at position E-E illustrated in FIG. 10, the overflow cavities 25 and 26 are in communication with each other. In addition, the overflow cavity 26 as a capillary area in an outer circumferential portion of rotation during the generation of centrifugal force is formed such that the cross-sectional dimension thereof (g1) in the thickness direction is smaller than the cross-sectional dimension (g2) of the overflow cavity 25 in an inner circumferential portion in the thickness direction thereof so as to enable capillary force to act.

In this case, while the cross-sectional dimensions (g1) of the connecting channel 21, the sample solution overflow cavity 22, the higher specific gravity component quantitative cavity 23, the connecting channel 24, the capillary cavity 19, and the sample solution overflow cavity 26 in the thickness directions thereof are arranged so as to range from 50 to 300 no particular restrictions are to be applied as long as the dimensions enable a sample liquid to be transferred by capillary force. In addition, while the cross-sectional dimensions (g2) of the separation cavity 18 and the sample solution overflow cavity 25 in the thickness directions thereof are arranged so as to range from 1000 to 3000 µm, the dimensions can be adjusted depending on a necessary amount of sample liquid.

As illustrated in FIG. 9, the diluent measuring section 153 is made up of: a diluent quantitative cavity 14 formed on the underside of the diluent holding section 151 and which holds a predetermined amount of a sample liquid transferred from the diluent receiving cavity 5 by centrifugal force; a siphon channel 15 formed between the diluent quantitative cavity 14 and the separating section 152 as a connecting channel that transfers a diluent measured by the diluent quantitative cavity 14 to the mixing section 154; an overflow channel 16 formed on the opposite side of the siphon channel 15 with respect to the diluent quantitative cavity 14 for overflowing a diluent transferred to the diluent quantitative cavity 14 to the outside of the diluent quantitative cavity 14 when the transferred diluent exceeds a predetermined amount; an overflow cavity 27 that regulates a surface height of a liquid to be held by the holding cavity 14 and into which a diluent overflows via the overflow channel 16; a diluent overflow cavity 29 that holds the overflowed diluent and which is used for reference measurements performed by the optical measurement unit 109; and a threshold 28 for preventing reflux of the diluent held in the diluent overflow cavity 29 and from flowing out to other areas. The threshold 28 is formed at a position that is circumferentially inward with respect to a liquid surface of the sample held in a measurement spot 29.

Figure 48A:
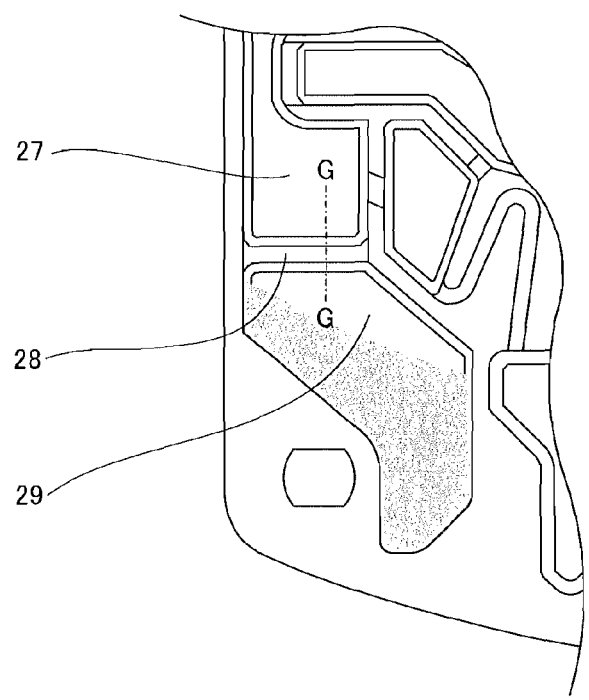
FIG. 48A is an enlarged view of a substantial part of FIG. 9.
Figure 48B:
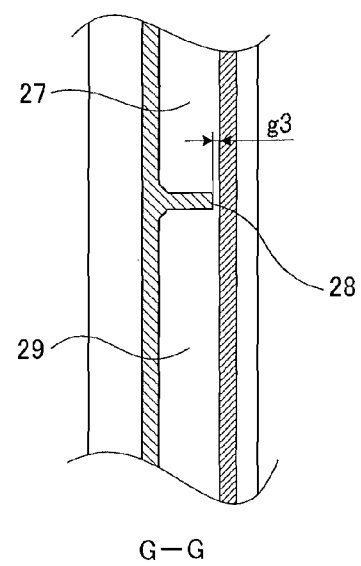
FIG. 48B is a G-G cross-sectional view of FIG. 48A.

FIG. 48A is an enlarged view of a substantial parts illustrated in FIG. 9. FIG. 48B is a partial cross-sectional view taken along G-G of the threshold 28. The cross-sectional dimension (g3) in the thickness direction is restricted to a size that enables capillary force to act.

In this case, while the cross-sectional dimensions (g3) of the connecting channel 15, the overflow channel 16, and the threshold 28 in the thickness directions thereof are arranged so as to range from 50 to 300 µm, any dimension shall suffice as long as the passage of liquid can be restricted by capillary force.

In addition, while the cross-sectional dimensions of the diluent quantitative cavity 14, the overflow cavity 27, and the diluent overflow cavity 29 in the thickness directions thereof are arranged so as to range from 1000 to 3000 µm, the dimensions can be adjusted depending on a necessary amount of sample liquid and on conditions (optical path length, measured wavelength, and the like) in which absorbance is to be measured.

As illustrated in FIG. 9, the mixing section 154 is made up of: a mixing cavity 30 formed on the underside of the separating section 152 and the diluent measuring section 153 so as to communicate with the higher specific gravity component quantitative cavity 23 and the siphon channel 15 as a third holding section that holds a sample liquid transferred from the higher specific gravity component quantitative cavity 23 and a diluent transferred from the diluent quantitative cavity 14 and internally mixes the sample liquid and the diluent; a rib 31 formed so as to prevent a diluted solution from flowing out during mixing through an air duct 20c provided inside the mixing cavity 30; a holding cavity 32 formed inward with respect to a liquid surface height of a diluent solution held in the mixing cavity 30 in the direction of the axial center 102 as a fourth holding section that holds the mixed diluted solution transferred from the mixing cavity 30; a mixed solution quantitative cavity 35 formed on the underside of the holding cavity 32 and which holds just a predetermined amount of a diluted solution transferred from the holding cavity 32 by centrifugal force; a capillary section 33 formed between the holding cavity 32 and the overflow cavity 27 and which prevents the diluted solution transferred to the holding cavity 32 from overflowing into the overflow cavity 27; a connecting channel 34 formed between the holding cavity 32 and the mixed solution quantitative cavity 35 and which prevents the diluted solution transferred to the holding cavity 32 from overflowing into the mixed solution quantitative cavity 35; a siphon channel 37 formed between the mixed solution quantitative cavity 35 and the measuring section 155 positioned on the underside of the mixed solution quantitative cavity 35 and which transfers a diluted solution measured by the mixed solution quantitative cavity 35 to the measuring section 155; and an overflow channel 36 formed between the mixed solution quantitative cavity 35 and the overflow cavity 27 for overflowing a diluted solution transferred to the mixed solution quantitative cavity 35 to the outside of the mixed solution quantitative cavity 35 when the transferred diluted solution exceeds a predetermined amount.

In this case, while the cross-sectional dimensions of the capillary section 33, the connecting channel 34, the overflow channel 36, and the siphon channel 37 in the thickness directions thereof are arranged so as to range from 50 to 300 μm, no particular restrictions are to be applied as long as the dimensions enable capillary force to act. In addition, while the cross-sectional dimensions of the holding cavity 32 and the mixed solution quantitative cavity 35 in the thickness directions thereof are arranged so as to range from 1000 to 3000 μm, the dimensions can be adjusted depending on a necessary amount of diluted solution.

As illustrated in FIG. 9, the measuring section 155 is made up of: a denaturing reaction cavity 38 formed on the underside of the mixing section 154 so as to communicate with the mixed solution quantitative cavity 35 via the siphon channel 37 and which is an operating cavity and a measurement spot for causing a reaction between a reagent held inside the denaturing reaction cavity 38 and a diluted solution transferred from the mixed solution quantitative cavity 35 via the siphon channel 37 and holding the reagent and the diluted solution to perform a first measurement; a denatured solution quantitative cavity 39 formed inward in the direction of the axial center 102 than a liquid surface height of a first reaction liquid held by the denaturing reaction cavity 38 that is an operating cavity as viewed from an immunoassay cavity 43 that is an operating cavity and a measurement spot, and which is formed as a receiving cavity that collects the first reaction liquid inside the denaturing reaction cavity 38 after a measurement of the first reaction liquid; a capillary cavity 40 formed between the denaturing reaction cavity 38 and the denatured solution quantitative cavity 39 for stabilizing the amount of the first reaction liquid that is returned to the denaturing reaction cavity 38; a connecting channel 41 formed on the underside of the denatured solution quantitative cavity 39 and which suppresses the first reaction liquid collected by the denatured solution quantitative cavity 39 from flowing out to the immunoassay cavity 43; a rib 42 positioned at a coupling section of the denatured solution quantitative cavity 39 and the capillary cavity 40 and which breaks the first reaction liquid in the denatured solution quantitative cavity 39 by centrifugal force and returns a predetermined amount of a diluted solution to the denaturing reaction cavity 38; the immunoassay cavity 43 formed on the underside of the denatured solution quantitative cavity 39 so as to communicate with the denatured solution quantitative cavity 39 via the connecting channel 41 for reacting a reagent held inside the immunoassay cavity 43 with the first reaction liquid transferred from the denatured solution quantitative cavity 39 via the connecting channel 41 and holding the reagent and the first reaction liquid to perform a second measurement; an immunoassay quantitative cavity 44 formed inward in the direction of the axial center 102 than a liquid surface height of a second reaction liquid held by the immunoassay cavity 43 that is an operating cavity as viewed from an agglutinative reaction cavity 46 as a measurement spot, and which is formed as a receiving cavity that collects the second reaction liquid inside the immunoassay cavity 43 after a measurement of the second reaction liquid; a capillary cavity 64 formed between the immunoassay cavity 43 and the immunoassay quantitative cavity 44 as a third coupling section for stabilizing the amount of the second reaction liquid that is returned to the immunoassay cavity 43; a connecting channel 45 formed on the underside of the immunoassay quantitative cavity 44 and which suppresses the immunoassay solution 62 as the second reaction liquid collected by the immunoassay quantitative cavity 44 from flowing out to the agglutinative reaction cavity 46; and the agglutinative reaction cavity 46 formed on the underside of the immunoassay quantitative cavity 44 so as to communicate with the immunoassay quantitative cavity 44 via the connecting channel 45 for reacting a reagent held inside the agglutinative reaction cavity 46 with the second reaction liquid transferred from the immunoassay quantitative cavity 44 via the connecting channel 45 and holding the reagent and the second reaction liquid to perform a third measurement.

In this case, while the cross-sectional dimensions of the denatured solution quantitative cavity 39, the capillary cavity 40, the connecting channel 41, the immunoassay quantitative cavity 44, and the connecting channel 45 in the thickness directions thereof are arranged so as to range from 50 to 500 μm, no particular restrictions are to be applied as long as the dimensions enable capillary force to act. In addition, while the cross-sectional dimensions of the denaturing reaction cavity 38, the immunoassay cavity 43, and the agglutinative reaction cavity 46 in the thickness directions thereof are arranged so as to range from 1000 to 3000 μm, the dimensions can be adjusted depending on a necessary amount of sample liquid and on conditions (optical path length, measured wavelength, reactive concentration of a sample solution, reagent types, and the like) in which absorbance is to be measured.

Next, a sample liquid analysis process by the analysis device 1 will be described in detail using concentration measurements of hemoglobin and HbA1c contained in blood cells in blood as examples.

It should be noted that FIGS. 14A and 14B to 22A and 22B illustrate the analysis device 1 set on the rotor 103 in a state as viewed from a surface side of the rotor 103. A rotational direction C1 with respect to the axial center 102 denotes a counter-clockwise rotation as seen in FIG. 1, while a rotational direction C2 with respect to the axial center 102 denotes a clockwise rotation as seen in FIG. 1.

Figure 14A:
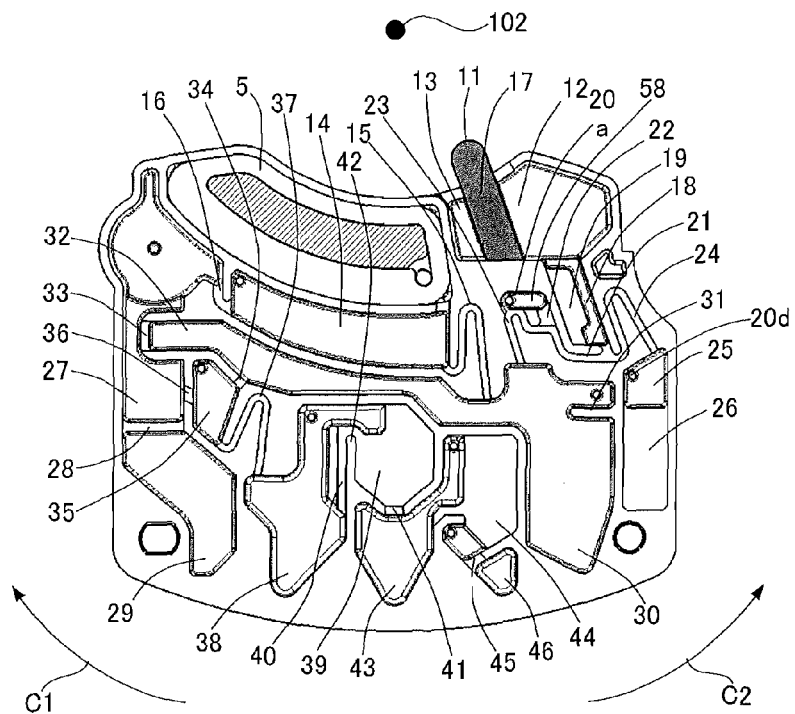
FIG. 14A is an explanatory diagram of an injection process of an analysis device according to an embodiment of the present invention.
Figure 14B:
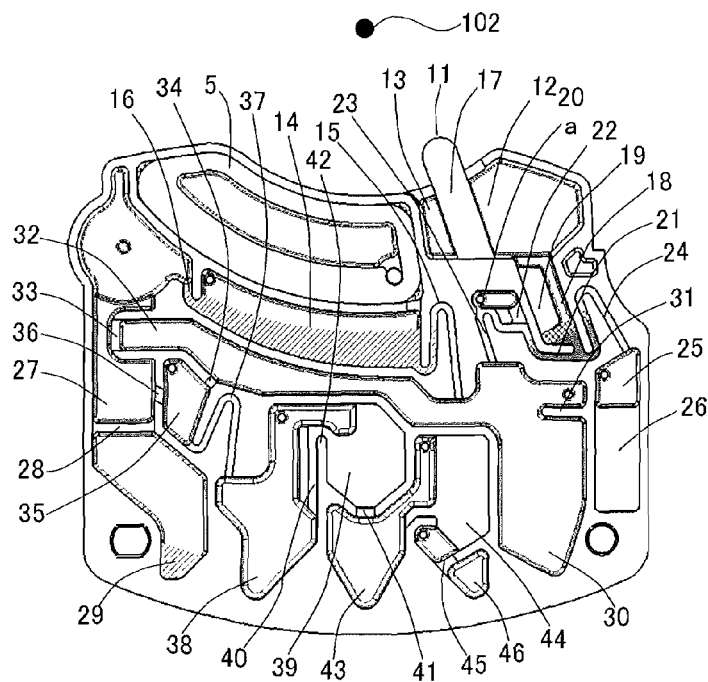
FIG. 14B is an explanatory diagram of a separation/measurement process of an analysis device according to an embodiment of the present invention.

FIGS. 14A and 14B illustrate an injection process and a separation/measurement process by an analysis device according to the first embodiment of the present invention.

Process 1

In FIG. 14A, blood that is a sample liquid is collected from a pierced fingertip or the like by the capillary force of the sample receiving cavity 17 via the inlet 11 of the analysis device 1 until the inside of the sample receiving cavity 17 is filled. In this case, while it is arranged that a sample liquid, e.g., approximately 10 μL of blood, can be measured in accordance with a volume determined by a gap and an opposing area of the sample receiving cavity 17, the shape and dimensions of the sample receiving cavity 17 may be regulated according to an amount necessary for analysis so as to adjust a collectable capacity.

The analysis device 1 having collected a required amount of blood is mounted on the rotor 103 of the analysis apparatus main body 100, whereby an opening operation is to be performed by an opening unit of the diluent receiving cavity 5.

Process 2

After opening of the diluent receiving cavity 5 is completed, by rotating the rotor 103 (in a clockwise rotation denoted by C2 at 3000 rpm), the blood and the diluent inside the sample receiving cavity 17 are transferred to the separation cavity 18 as illustrated in FIG. 14B, and 300 µL of the diluent in the diluent receiving cavity 5 is transferred to the diluent quantitative cavity 14. At this point, when diluting blood and extracting a measured component from the blood cells, in order to reduce variances in dilution attributable to hematocrit levels (the ratio of a blood cell component in blood) which vary from person to person, variances in dilution is reduced by separating blood transferred to the separation cavity 18 by centrifugal force into a blood plasma component and a blood cell component, and collecting and diluting high hematocrit blood in an outer circumferential portion.

In addition, the diluent transferred to the diluent quantitative cavity 14 during the rotation which exceeds a predetermined amount flows into and is held by the diluent overflow cavity 29 via the overflow channel 16, the overflow cavity 27, and the threshold 28.

FIGS. 15A to 15D illustrate the centrifugal separation operation at the separation cavity 18 having the capillary cavity 19 and a transfer flow to the mixing cavity 30 via the high specific gravity component quantitative cavity 23.

While the capillary cavity 19 according to the present embodiment is formed so as to be in contact with a left side face in the separation cavity 18, a similar effect can be achieved by forming the capillary cavity 19 so as to be in contact with a right side face in the separation cavity 18. An end of the capillary cavity 19 is formed up to an outer circumferential position with respect to a liquid surface of blood 57 so as to be immersed in the blood 57 as a sample liquid which is held in the separation cavity 18 as illustrated in FIG. 15A.

In addition, the connecting channel 24 has a siphon structure that is in communication with an outermost circumferential position of the connecting channel 21 and which bends at a position circumferentially inward from the liquid surface of the sample liquid held in the separation cavity 18. The sample solution overflow cavity 26 is positioned circumferentially outward with respect to an outermost circumferential position of the connecting channel 21 and communicates with the separation cavity 18 via the connecting channel 24.

Figure 15A:
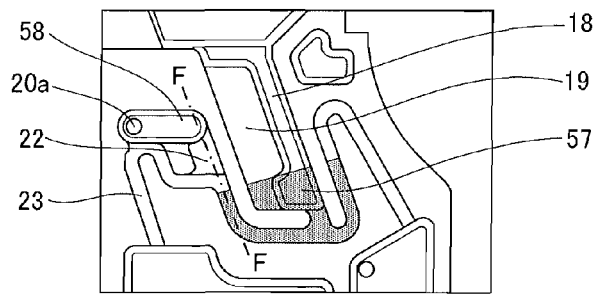
FIG. 15A is an operation explanatory diagram of a bifurcation section of a separation cavity 18 including a capillary cavity 19 from a sample solution overflow cavity 22 and a connecting channel 21 according to an embodiment of the present invention.
Figure 15B:
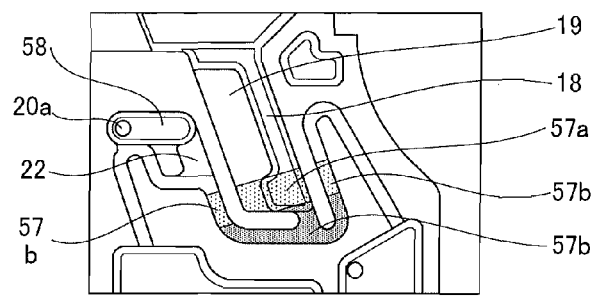
FIG. 15B is an operation explanatory diagram of a bifurcation section of the separation cavity 18 including the capillary cavity 19 from the sample solution overflow cavity 22 and the connecting channel 21 according to an embodiment of the present invention.
Figure 15C:
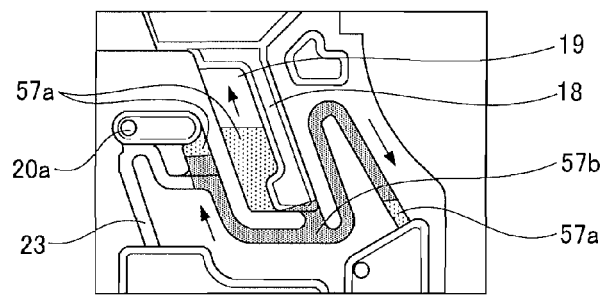
FIG. 15C is an operation explanatory diagram of a bifurcation section of the separation cavity 18 including the capillary cavity 19 from the sample solution overflow cavity 22 and the connecting channel 21 according to an embodiment of the present invention.
Figure 15D:
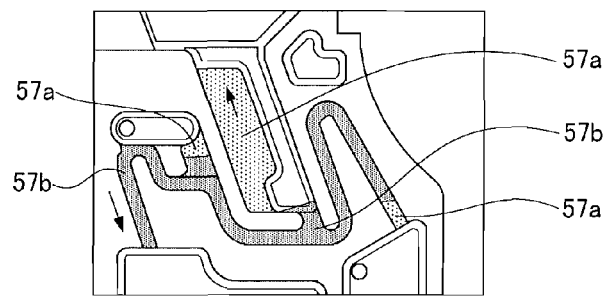
FIG. 15D is an operation explanatory diagram of a bifurcation section of the separation cavity 18 including the capillary cavity 19 from the sample solution overflow cavity 22 and the connecting channel 21 according to an embodiment of the present invention.

Blood 57 collected at a bottom portion of the separation cavity 18 as illustrated in FIG. 15A is separated by centrifugal force into a blood plasma component 57a and a blood cell component 57b as illustrated in FIG. 15B. When rotation stops and centrifugal force ceases, as illustrated in FIG. 15C, the blood plasma component 57a in the separation cavity 18 is capillary transferred to the capillary cavity 19. The blood plasma component 57a and the blood cell component 57b in the connecting channel 21 are capillary transferred towards the sample solution overflow cavity 22 connected, to a cavity 58 having an air duct 20a that communicates with air. The blood plasma component 57a and the blood cell component 57b in the connecting channel 24 are capillary transferred towards the sample solution overflow cavity 26 having an air duct 20d that communicates with air. In this case, an end of the higher specific gravity component quantitative cavity 23 is connected to the connecting channel 21 at a position reached by the blood cell component 57b and, as illustrated in FIG. 15D, only a required amount of the blood cell component 57b is transferred from the connecting channel 21 by the capillary force of the higher specific gravity component quantitative cavity 23.

Figure 16A:
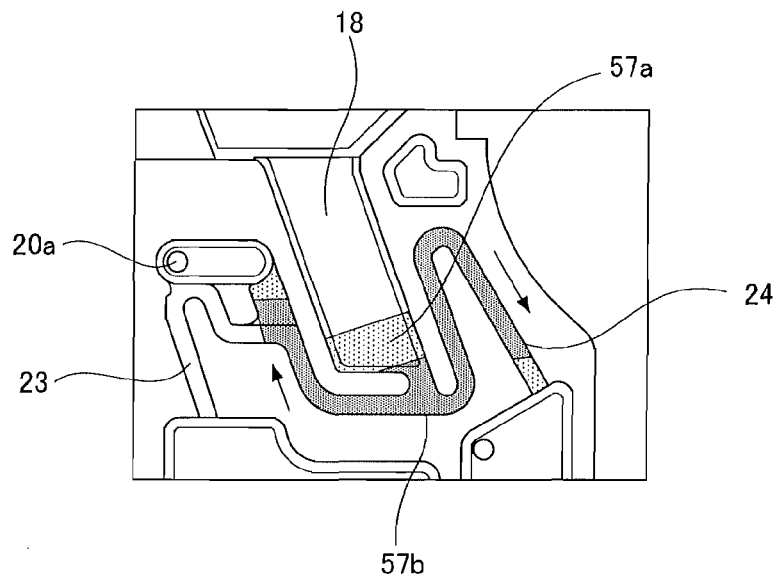
FIG. 16A is an operation explanatory diagram of a separation cavity 18 of a comparative example not including a capillary cavity 19.
Figure 16B:
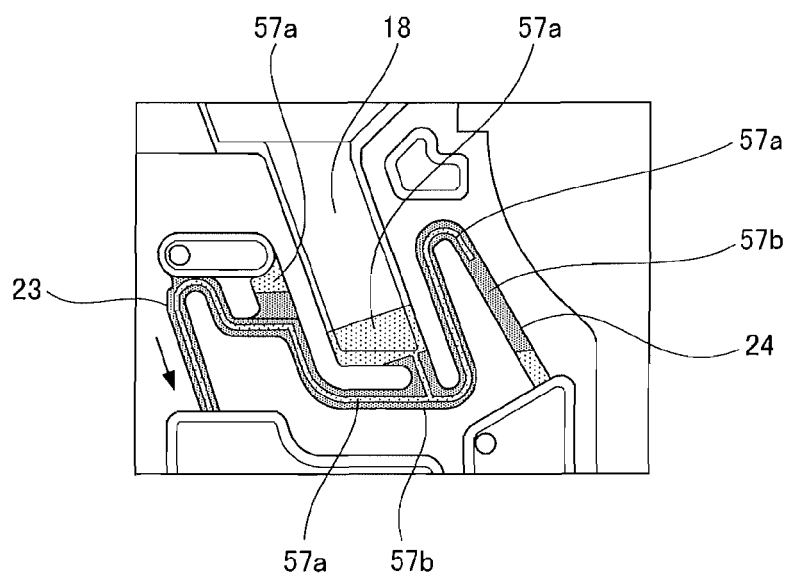
FIG. 16B is an operation explanatory diagram of the separation cavity 18 of a comparative example not including the capillary cavity 19.

In the present invention, since the capillary cavity 19 is formed in the separation cavity 18, almost all of the blood plasma component 57a remaining in the separation cavity 18 can be held by the capillary cavity 19, thereby contributing towards capillary transferring just a required amount of the blood cell component 57b to the higher specific gravity component quantitative cavity 23. Specifically, in a comparative example such as illustrated in FIG. 16A in which the capillary cavity 19 is not formed in the separation cavity 18, the blood plasma component 57a is collected in the bottom portion of the separation cavity 18. When capillary transfer is carried out by the capillary force of the higher specific gravity component quantitative cavity 23, the blood plasma component 57a collected in the bottom portion of the separation cavity 18 is immixed towards the higher specific gravity component quantitative cavity 23 from the connecting channel 21, thereby preventing a necessary amount of the blood cell component 57b from being obtained and consequently demonstrating the effectiveness of the capillary cavity 19.

Furthermore, a bifurcation section of the sample solution overflow cavity 22 and the connecting channel 21 provided between the separation cavity 18 and the higher specific gravity component quantitative cavity 23 will now be described in detail.

Figure 23A:
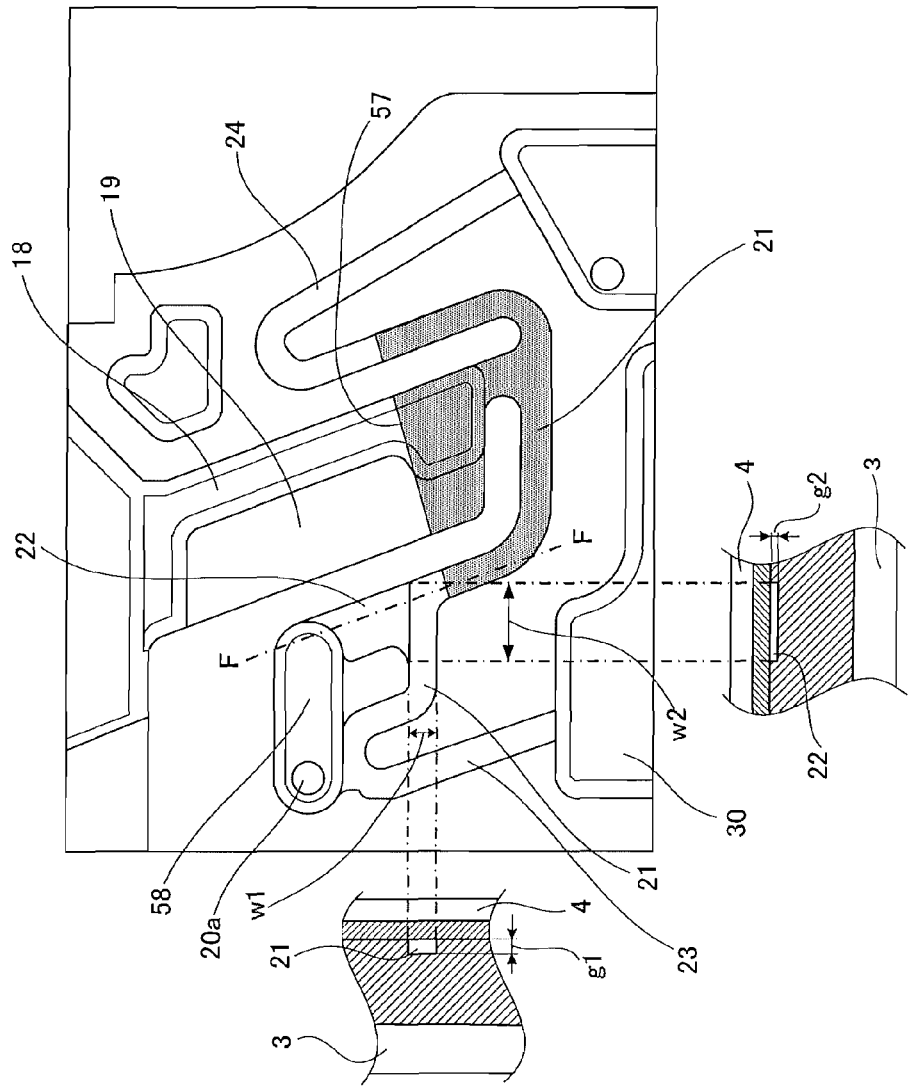
FIG. 23A is an enlarged view of a bifurcation section of the sample solution overflow cavity 22 and the connecting channel 21 of an analysis device according to an embodiment of the present invention.
Figure 23B:
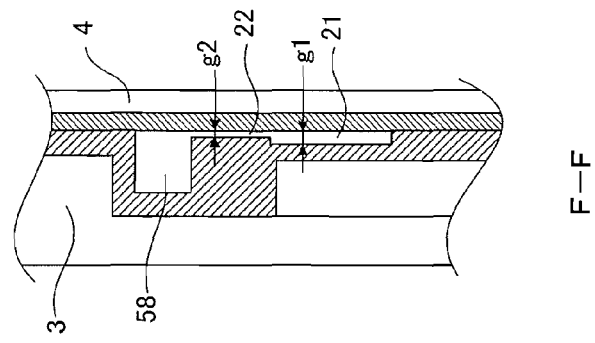
FIG. 23B is a cross-sectional view of a substantial part of a bifurcation section of the sample solution overflow cavity 22 and the connecting channel 21 of an analysis device according to an embodiment of the present invention.

FIGS. 23A and 23B are, respectively, an enlarged view and a cross-sectional view of a substantial part of the bifurcation section of the sample solution overflow cavity 22 and the connecting channel 21. FIG. 23B is a cross-sectional view taken along F-F in FIG. 23A. When the cross-sectional dimension g1 of the connecting channel 21 in the thickness direction thereof is assumed to be 0.2 mm, the cross-sectional dimension g2 of the sample solution overflow cavity 22 in the thickness direction thereof is formed so as to be smaller than g1 to, for example, 0.1 mm that is half of g1 so as to minimize the amount of blood plasma component mixed into the higher specific gravity component quantitative cavity 23. In addition, a width w2 of the sample solution overflow cavity 22 in a direction intersecting a flow direction of the sample solution overflow cavity 22 is formed wider than a width w1 of the connecting channel 21 in a direction intersecting a flow direction of the connecting channel 21.

As shown, by setting the cross-sectional dimension g2 of the sample solution overflow cavity 22 in the thickness direction thereof to half of the cross-sectional dimension g1 of the connecting channel 21 in the thickness direction thereof, the capillary force generated in the sample solution overflow cavity 22 becomes greater than the capillary force generated in the connecting channel 21. As a result, a blood plasma component is preferentially transferred into the sample solution overflow cavity 22 at the bifurcation section of the connecting channel 21 and the sample solution overflow cavity 22. In addition, by arranging the width w2 of the sample solution overflow cavity 22 in the direction intersecting the flow direction of the sample solution overflow cavity 22 to be wider than the width w1 of the connecting channel 21 in the direction intersecting the flow direction of the connecting channel 21, the capillary force generated in the sample solution overflow cavity 22 becomes greater than the capillary force generated in the connecting channel 21. As a result, a blood plasma component in the connecting channel 21 can be reliably transferred into the sample solution overflow cavity 22. When the cross-sectional dimension g2 is equal to or greater than half of the cross-sectional dimension g1, there is a risk that due to differences in channel surface conditions, the capillary forces of the sample solution overflow cavity 22 and the connecting channel 21 become similar to each other and cause a portion of the blood plasma component to flow into the higher specific gravity component quantitative cavity 23. Therefore, the cross-sectional dimension g2 of the sample solution overflow cavity 22 in the thickness direction thereof is desirably set to or less than half of the cross-sectional dimension g1 of the connecting channel 21 in the thickness direction thereof.

In addition, since the connecting channel 24 communicates with an outermost circumferential position of the connecting channel 21, sample liquids unnecessary for the aforementioned measurement and which are held in the sample solution overflow cavity 22, the separation cavity 18, the capillary cavity 19, the connecting channel 21, and the connecting channel 24 can all be discharged into the sample solution overflow cavity 26 when transferring the blood cell component 57b held in the higher specific gravity component quantitative cavity 23 to the mixing cavity 30 by centrifugal force. Consequently, an inflow of the remaining sample liquid into the mixing cavity 30 due to follow-up can be prevented.

As shown, by forming the capillary cavity 19 in the separation cavity 18 and trapping the blood plasma component 57a remaining in the separation cavity 18 by the capillary cavity 19, blood plasma component that becomes mixed into the higher specific gravity component quantitative cavity 23 after centrifugal separation can be eliminated and, at the same time, the blood plasma component 57a mixed into the connecting channel 21 can be siphoned and removed by capillary force by the sample solution overflow cavity 22. Therefore, only a predetermined amount of the blood cell component 57b is accurately held by the sample solution overflow cavity 22 and flows into the mixing cavity 30 in a subsequent process, and a predetermined amount of diluent accurately flows into the mixing cavity 30 from the diluent quantitative cavity 14 via the siphon channel 15. In other words, when the held liquid surface height of the diluent transferred to the diluent quantitative cavity 14 exceeds a coupling position of the overflow channel 16 and the overflow cavity 27, the diluent is discharged to the overflow cavity 27 via the overflow channel 16 and only a predetermined amount is held in the diluent quantitative cavity 14. In this case, since the siphon channel 15 has a siphon shape including a bent tube positioned radially inwards from the coupling position of the overflow channel 16 and the overflow cavity 27, the diluent can be held in the diluent quantitative cavity 14 during the rotation of the analysis device 1.

Furthermore, since the overflow channel 16 coupling the diluent quantitative cavity 14 and the overflow cavity 27 is a capillary, outflow of diluent from the diluent quantitative cavity 14 to the overflow cavity 27 due to inertial force or surface tension during deceleration and stopping of the analysis device 1 can be prevented by capillary force, and diluent measurement can be performed in an accurate manner.

Process 3

Figure 17A:
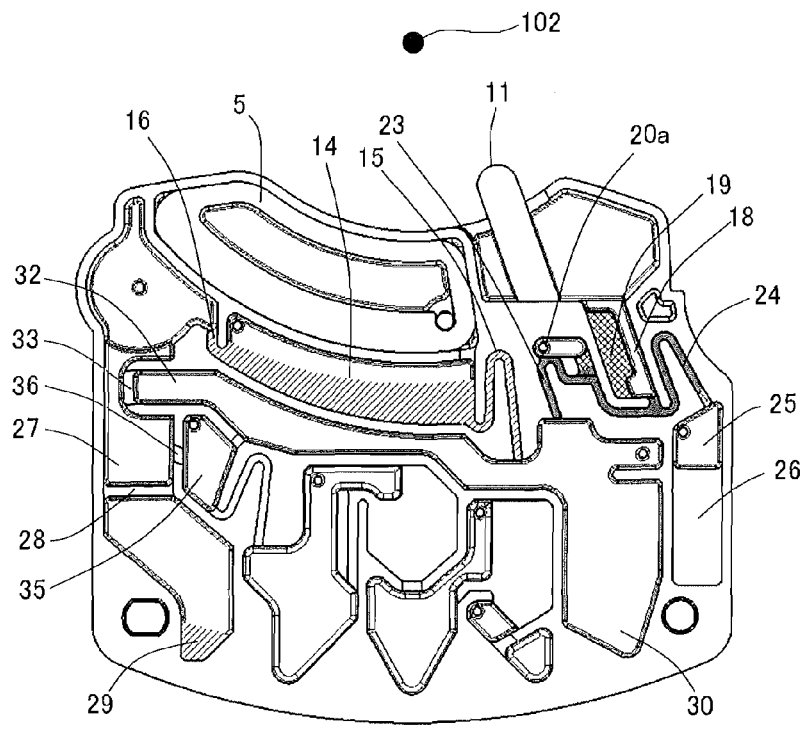
FIG. 17A is an explanatory diagram of a measurement process of an analysis device according to an embodiment of the present invention.
Figure 17B:
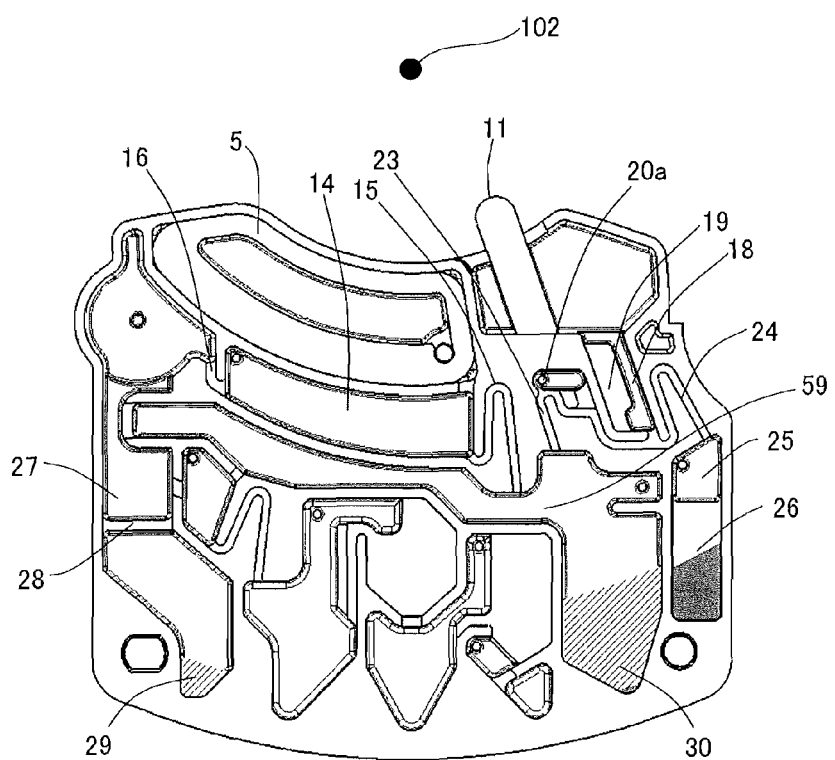
FIG. 17B is an explanatory diagram of a mixing process of an analysis device according to an embodiment of the present invention.

By stopping the rotation (the clockwise rotation denoted by C2 at 3000 rpm) of the rotor 103 and subsequently rotating (the clockwise rotation denoted by C2 at 2000 rpm) the rotor 103 from FIG. 17A, the necessary amount of the blood cell component 57b held in the higher specific gravity component quantitative cavity 23 and the diluent of the diluent quantitative cavity 14 flow into the mixing cavity 30 to be mixed and diluted, while surplus blood cell component 57b is to be held in the sample solution overflow cavity 26 as illustrated in FIG. 17B. In addition, the optical measurement unit 109 performs a reference measurement in which reading is carried out at a timing where the diluent of the diluent overflow cavity 29 of the analysis device 1 exists between the light source 105 and the photodetector 106. At this point, reference measurement is performed by switching the wavelengths of the light source 105 between 535 nm and 625 nm.

Process 4

Figure 18A:
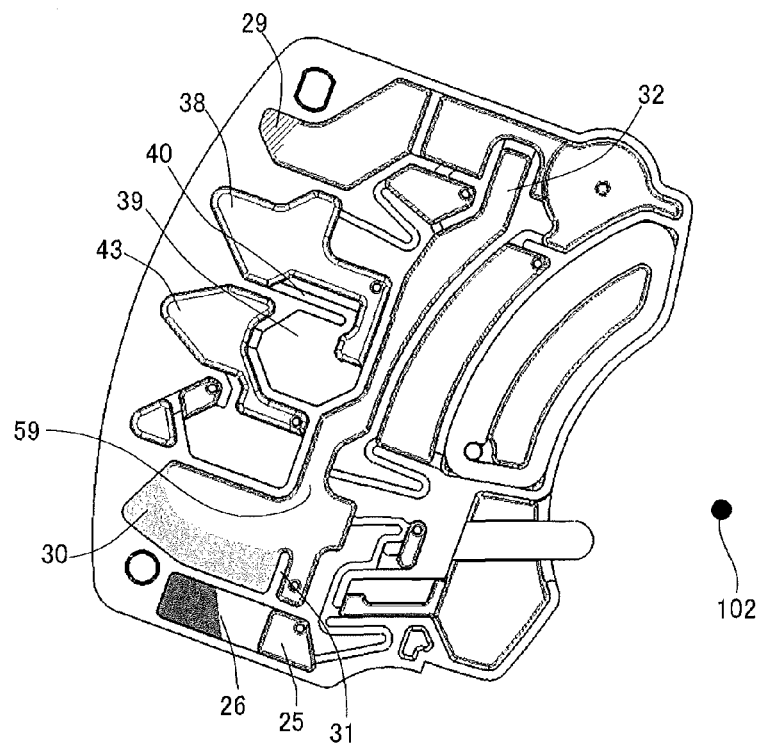
FIG. 18A is an explanatory diagram of a mixing process of an analysis device according to an embodiment of the present invention.

Next, by setting the analysis device 1 to a position near 60 degrees as illustrated in FIG. 18A, the diluent is agitated by controlling the motor 104 at a frequency of 1000 rpm so as to apply a swinging motion of around ±1 mm to the analysis device 1.

Process 5

Figure 18B:
FIG. 18B is an explanatory diagram of a mixing process of an analysis device according to an embodiment of the present invention.
Figure 18B:
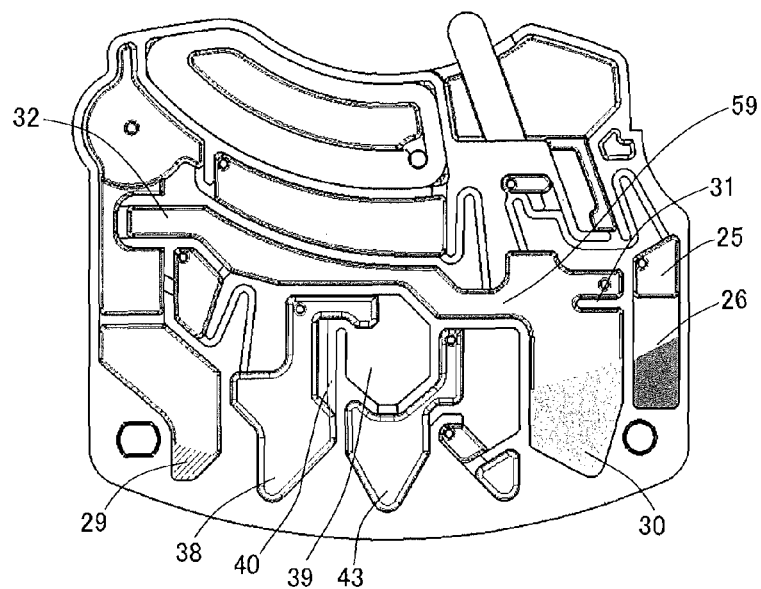

Subsequently, by setting the analysis device 1 to a position near 180 degrees as illustrated in FIG. 18B, the diluent is agitated by controlling the motor 104 at a frequency of 1000 rpm so as to apply a swinging motion of around ±1 mm to the analysis device 1.

At this point, since the mixing cavity 30 and the holding cavity 32 are brought into communication with each other by a coupling section 59 and the coupling section 59 during agitation is positioned circumferentially inwards than a liquid surface of a mixed solution held in the mixing cavity 30 with respect to the axial center 102 of rotation that generates centrifugal force, the diluent during agitation and mixing is prevented from overflowing to the holding cavity 32.

Process 6

Figure 19A:
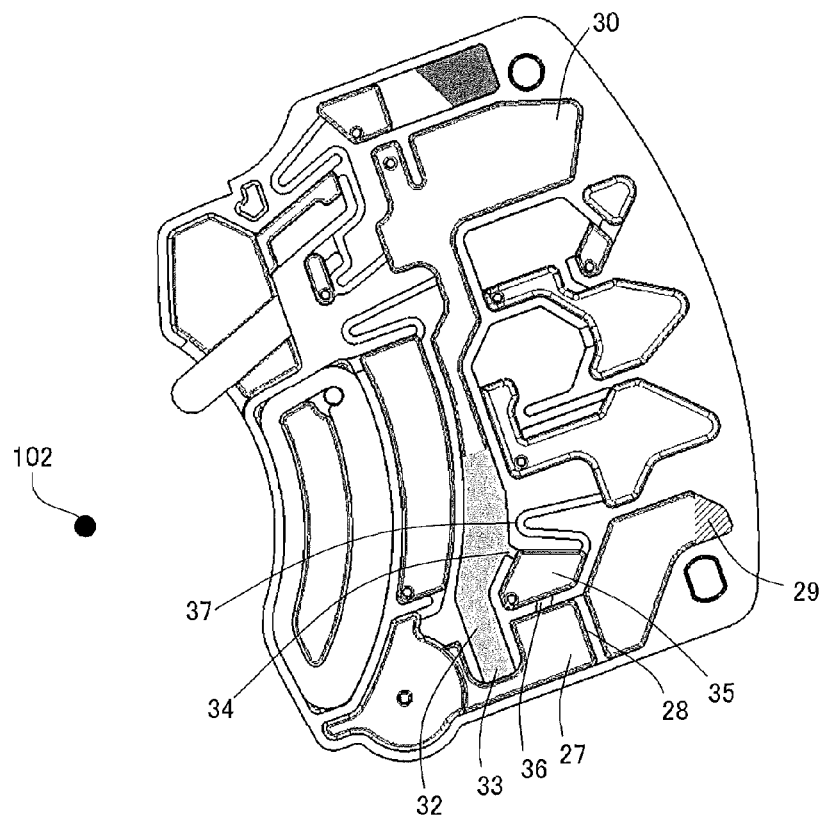
FIG. 19A is an explanatory diagram of a diluted solution transfer process of an analysis device according to an embodiment of the present invention.
Figure 19B:
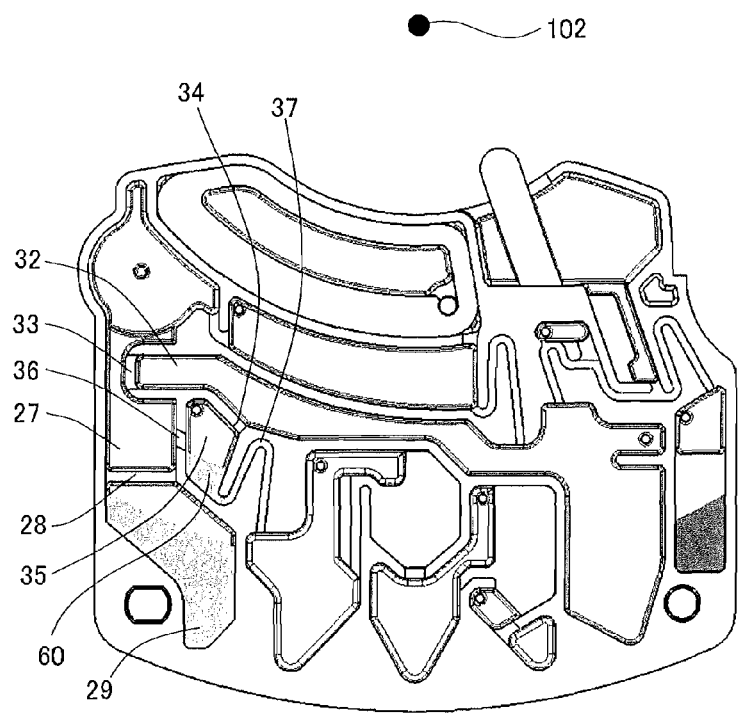
FIG. 19B is an explanatory diagram of a measurement process of an analysis device according to an embodiment of the present invention.

Next, by setting the analysis device 1 to a position near 300 degrees as illustrated in FIG. 19A, the diluent is agitated by controlling the motor 104 at a frequency of 1000 rpm so as to apply a swinging motion of around ±1 mm to the analysis device 1 in order to swingingly transfer the blood cell component 57b (mixed solution) after dilution of the mixing cavity 30 to the holding cavity 32 via the coupling section 59.

At this point, the mixed solution held in the mixing cavity 30 is held by a surface tension acting on a wall surface of the mixing cavity 30 (since the surface tension is greater than the gravity acting on the mixed solution) even when the analysis device 1 is moved to a position near 300 degrees as illustrated in FIG. 19A. By swinging the analysis device 1 and applying inertial force to the mixed solution, the surface tension acting on the wall surface of the mixing cavity 30 can be negated and the mixed solution can be transferred to the holding cavity 32 by the inertial force and gravity acting on the mixed solution.

Process 7

Subsequently, by rotating (clockwise rotation denoted by C2 at 2000 rpm) the rotor 103 and therefore the analysis device 1, a predetermined amount of the mixed solution is transferred to the mixed solution quantitative cavity 35 from the holding cavity 32 via the connecting channel 34. The portion of the mixed solution transferred to the mixed solution quantitative cavity 35 exceeding the predetermined amount overflows to the overflow cavity 27 via the overflow channel 36, and only the predetermined amount of a mixed solution 60 is held in the mixed solution quantitative cavity 35.

Process 8

Figure 20A:
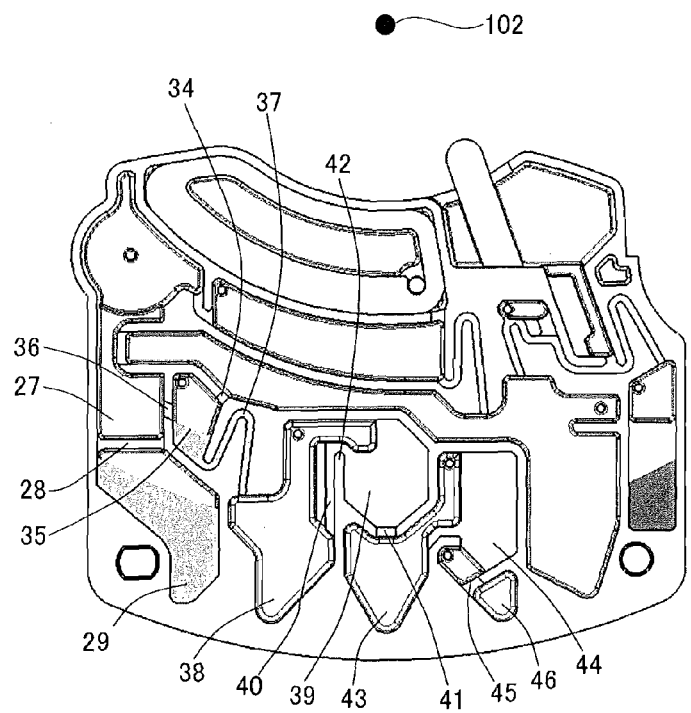
FIG. 20A is an explanatory diagram of a transfer process of an analysis device according to an embodiment of the present invention.

By stopping the rotation (the clockwise rotation denoted by C2 at 2000 rpm) of the rotor 103, the mixed solution of the mixed solution quantitative cavity 35 is primed into the siphon channel 37 as illustrated in FIG. 20A. By further rotating (the counter-clockwise rotation denoted by C1 at 2000 rpm) the rotor 103 from FIG. 20A, the predetermined amount of mixed solution held in the mixed solution quantitative cavity 35 is transferred to the denaturing reaction cavity 38 that is an operation cavity and a measurement spot via the siphon channel 37, and causes a denaturing reagent held in advance in the denaturing reaction cavity 38 to dissolve.

Process 9

Figure 20B:
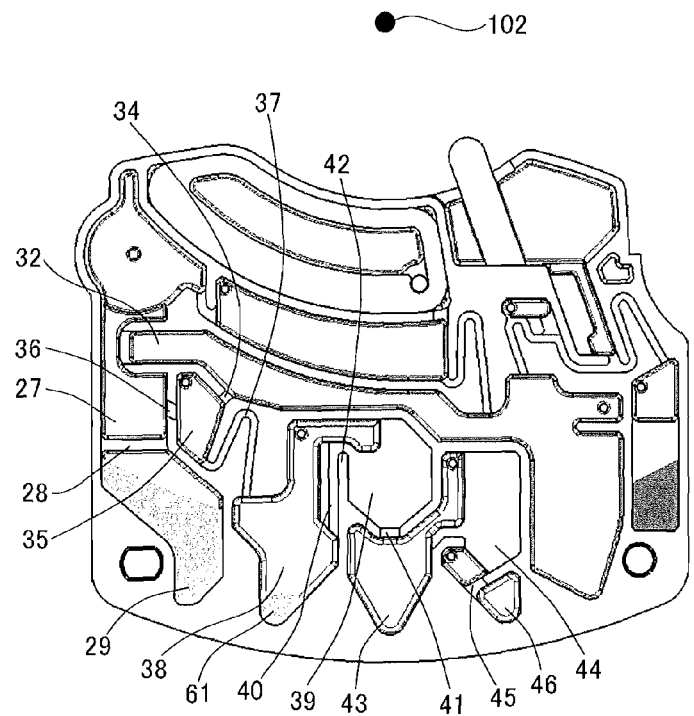
FIG. 20B is an explanatory diagram of a reagent reaction/measurement process of an analysis device according to an embodiment of the present invention.

Subsequently, at a position near 180 degrees as illustrated in FIG. 20B, the motor 104 is controlled at a frequency of 1000 rpm so as to apply a swinging motion of around ±1 mm to the analysis device 1 in order to agitate a denatured solution 61 in the denaturing reaction cavity 38 as a first reaction liquid of the analysis device 1.

The denaturing reaction cavity 38 and the side of the immunoassay cavity 43 are brought into communication with each other by the capillary cavity 40 and the denatured solution quantitative cavity 39. At this point, since the capillary cavity 40 acts as a second coupling section and the capillary cavity 40 during agitation is positioned circumferentially inwards than a liquid surface of a mixed solution held in the denaturing reaction cavity 38 with respect to the axial center 102 of rotation that generates centrifugal force, the mixed solution during agitation and mixing is prevented from overflowing to the denatured solution quantitative cavity 39 on the side of the immunoassay cavity 43.

Process 10

Next, after immobilizing the analysis device 1 and causing a denaturing reaction of the denatured solution 61 of the denaturing reaction cavity 38, the rotor 103 is rotated (counter-clockwise rotation denoted by C1 at 1500 rpm) to perform a first measurement.

The first measurement involves, in a luminescent state where the wavelength of the light source 105 is switched to 535 nm, performing reading at a timing where the denatured solution 61 of the denaturing reaction cavity 38 of the analysis device 1 subjected to denaturing reaction exists between the light source 105 and the photodetector 106. The computing section 110 processes a measurement value obtained by the first measurement based on a reference value obtained by reading, in advance, the diluent overflow cavity 29 while setting the wavelength of the light source 105 to 535 nm, and displays a numerical denatured hemoglobin concentration on the displaying section 111.

Total hemoglobin in the mixed solution or the denatured solution is determined by causing a reaction of the mixed solution and the denaturing reagent held in the denaturing reaction cavity 38 and subsequently measuring a hemoglobin derivative concentration in a measurement region formed in the denaturing reaction cavity.

Alternatively, a hemoglobin measurement can be performed in the mixing cavity 30 prior to denaturing based on colorimetric levels of a light-emitting diode light source with a wavelength of 410 nm utilizing γ peak (Soret band) absorption of hemoglobin.

As used herein, "denaturation" refers to taking out (exposing) a specific part from the inside of a protein structure to the outside of the structure. An antigen-antibody reaction to be described later is performed using a latex reagent that specifically reacts with a "denatured region" that is a region exposed outside of the protein structure.

Process 11

Figure 21A:
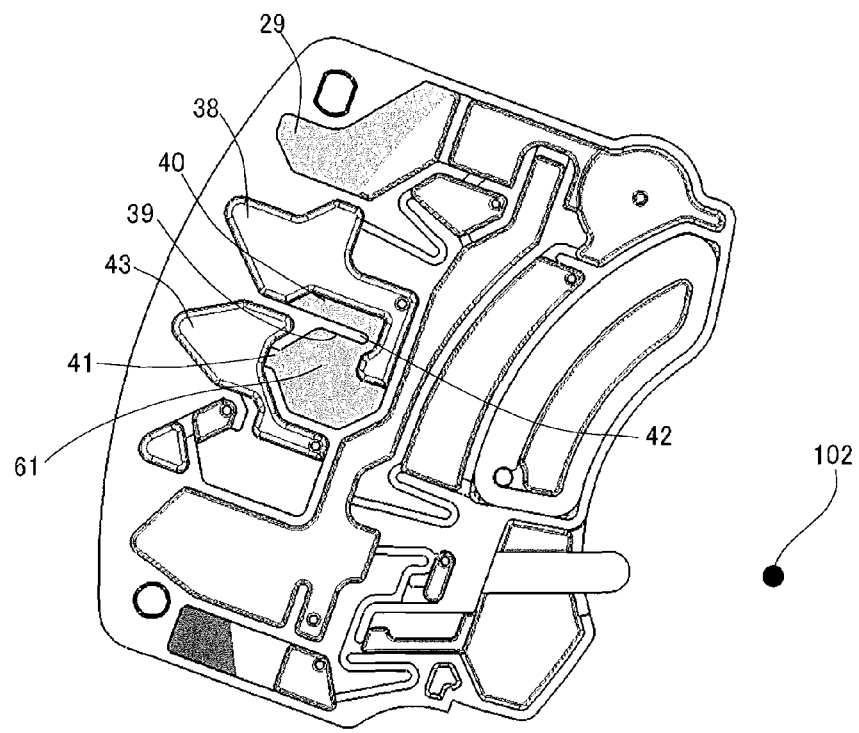
FIG. 21A is an explanatory diagram of a transfer process of an analysis device according to an embodiment of the present invention.

Next, by setting the analysis device 1 to a position near 60 degrees as illustrated in FIG. 21A and controlling the motor 104 at a frequency of 1500 rpm so as to apply a swinging motion of around ±1 mm to the analysis device 1, the denatured solution 61 held in the denaturing reaction cavity 38 is capillary transferred to the denatured solution quantitative cavity 39. A predetermined amount of the denatured solution 61 that is the first reaction liquid is held in the denatured solution quantitative cavity 39.

Process 12

Next, by rotating the rotor 103 (counter-clockwise rotation denoted by C1 at 2000 rpm), the denatured solution 61 flows into the immunoassay cavity 43 from the denatured solution quantitative cavity 39 via the connecting channel 41 to dissolve a latex reagent held in advance in the immunoassay cavity 43.

Process 13

Figure 21B:
FIG. 21B is an explanatory diagram of a reagent reaction/measurement process of an analysis device according to an embodiment of the present invention.
Figure 21B:
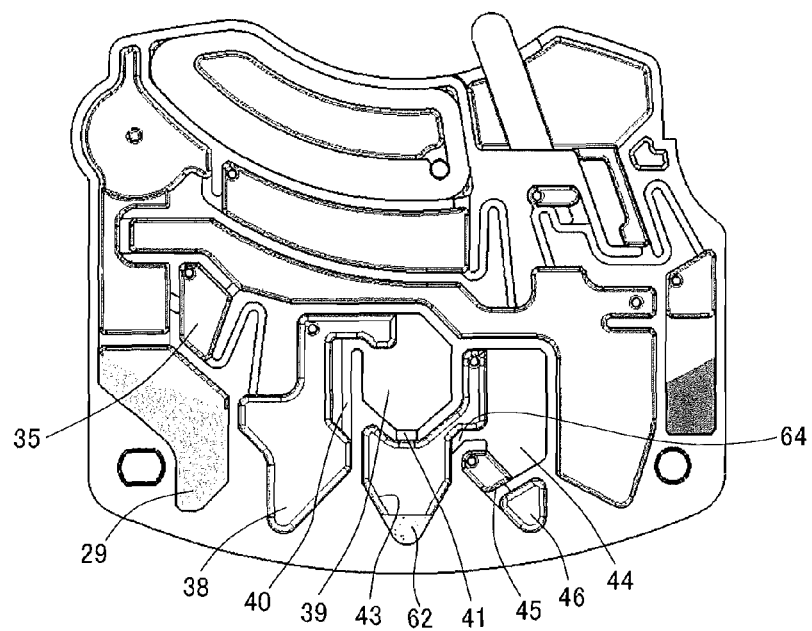

Subsequently, at a position near 180 degrees as illustrated in FIG. 21B, the motor 104 is controlled at a frequency of 1000 rpm so as to apply a swinging motion of around ±1 mm to the analysis device 1 in order to agitate an immunoassay solution 62 in the immunoassay cavity 43 of the analysis device 1. In the immunoassay cavity 43, the immunoassay solution is involved in an antigen-antibody reaction caused by a reagent (e.g., a latex reagent) containing an antibody specific for a denatured region of a hemoglobin derivative.

In this case, the immunoassay cavity 43 and the side of the agglutinative reaction cavity 46 are in communication with each other via the immunoassay quantitative cavity 44. Since the capillary cavity 64 that connects the immunoassay cavity 43 and the immunoassay quantitative cavity 44 is positioned, during agitation, circumferentially inward from the liquid surface of a mixed solution held in the immunoassay cavity 43 with respect to the axial center 102 of the rotation that generates centrifugal force, the mixed solution during agitation and mixing is prevented from flowing out to the immunoassay quantitative cavity 44 on the side of the agglutinative reaction cavity 46.

Process 14

Next, after immobilizing the analysis device 1 and causing an antigen-antibody reaction of the immunoassay solution 62, the rotor 103 is rotated (counter-clockwise rotation denoted by C1 at 1500 rpm) to perform a second measurement.

While the second measurement involves, in a luminescent state where the wavelength of the light source 105 is switched to 625 nm, measuring the concentration of a hemoglobin derivative, a blank measurement is performed at a timing where the immunoassay solution 62 of the immunoassay cavity 43 of the analysis device 1 subjected to antigen-antibody reaction exists between the light source 105 and the photodetector 106.

Process 15

Figure 22A:
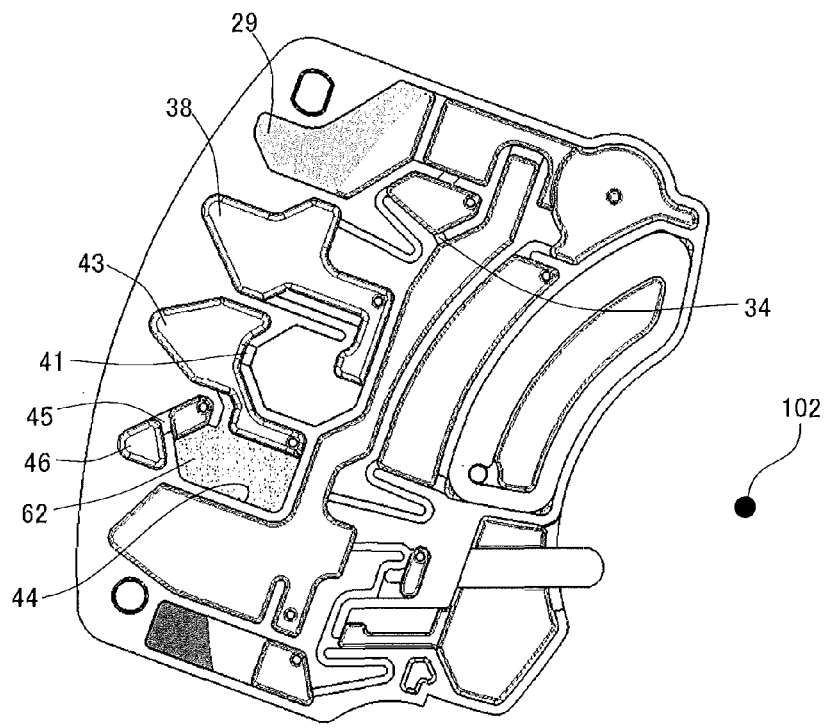
FIG. 22A is an explanatory diagram of a transfer process of an analysis device according to an embodiment of the present invention.

Next, by setting the analysis device 1 to a position near 60 degrees as illustrated in FIG. 22A, the motor 104 is controlled at a frequency of 1500 rpm so as to apply a swinging motion of around ±1 mm to the analysis device 1 in order to transfer the immunoassay solution 62 that is the second reaction liquid to the immunoassay quantitative cavity 44 by capillary force.

Process 16

Subsequently, by rotating (counter-clockwise rotation denoted by C1 at 2000 rpm) the rotor 103, the immunoassay solution 62 of a predetermined amount held by the immunoassay quantitative cavity 44 flows into the agglutinative reaction cavity 46 via the connecting channel 45 and dissolves an agglutination reagent held at the agglutinative reaction cavity 46.

Process 17

Figure 22B:
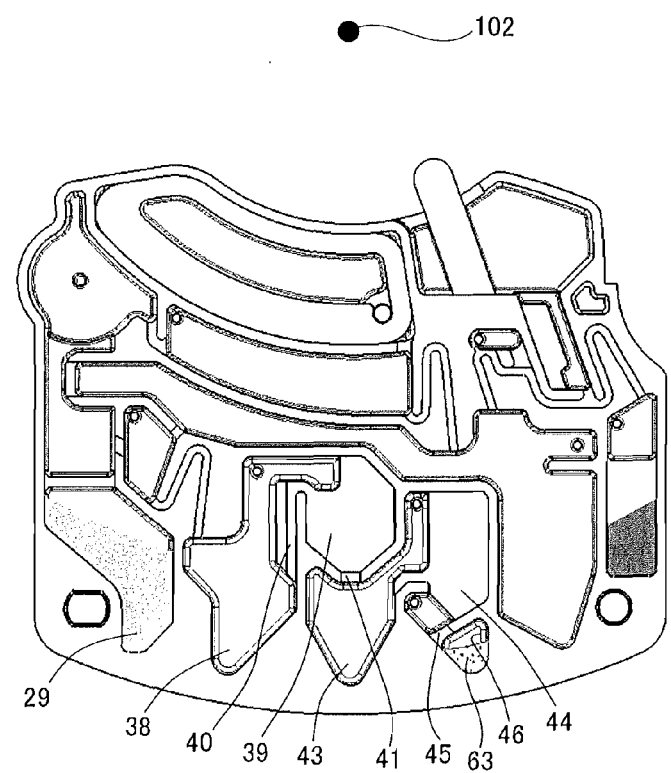
FIG. 22B is an explanatory diagram of a reagent reaction/measurement process of an analysis device according to an embodiment of the present invention.

Subsequently, at a position near 180 degrees as illustrated in FIG. 22B, the motor 104 is controlled at a frequency of 1000 rpm so as to apply a swinging motion of around ±1 mm to the analysis device 1 in order to agitate an agglutinated solution 63 in the agglutinative reaction cavity 46 of the analysis device 1. As a result, agglutination occurs in the agglutinative reaction cavity 46 due to a reaction bonding between an agglutinating agent and an unreacted body in which the antibody has not yet bonded with a hemoglobin derivative.

Process 18

Next, after immobilizing the analysis device 1 and causing an agglutination reaction of the agglutinated solution 63 as a third reaction liquid, the rotor 103 is rotated (counter-clockwise rotation denoted by C1 at 1500 rpm) to perform a third measurement.

The third measurement involves, in a luminescent state where the wavelength of the light source 105 is switched to 625 nm, performing reading at a timing where the agglutinated solution 63 of the agglutinative reaction cavity 46 of the analysis device 1 subjected to agglutinative reaction exists between the light source 105 and the photodetector 106, and measuring the turbidity of the agglutinated solution 63.

The computing section 110 displays the measurement values obtained by the second measurement and the third measurement on the displaying section 111 as a HbA1c concentration processed and numerically converted based on a reference value obtained by reading, in advance, the diluent overflow cavity 29 by setting the wavelength of the light source 105 to 625 nm, and a HbA1c % value calculated based on the denatured hemoglobin concentration.

Moreover, among the portion of the mixing cavity 30 and the holding cavity 32, the holding cavity 32 is the receiving cavity.

In addition, among the portion of the denaturing reaction cavity 38 and the denatured solution quantitative cavity 39, the denaturing reaction cavity 38 is the operating cavity and the denatured solution quantitative cavity 39 is the receiving cavity.

Furthermore, among the portion of the immunoassay cavity 43 and the immunoassay quantitative cavity 44, the immunoassay cavity 43 is the operating cavity and the immunoassay quantitative cavity 44 is the receiving cavity.

In the embodiment described above, access units for reading reactants at the denaturing reaction cavity 38, the immunoassay cavity 43, and the agglutinative reaction cavity 46 of the analysis device 1 have been arranged to optically access reaction liquids as reactants of the denaturing reaction cavity 38, the immunoassay cavity 43, and the agglutinative reaction cavity 46. However, the access units may alternatively perform an electrostatic coupling or an electromagnetic coupling to a reactant at at least any of the measurement spots of the denaturing reaction cavity 38, the immunoassay cavity 43, and the agglutinative reaction cavity 46 to contactlessly electrically access and read the reactant, or an electrode may be provided at at least any of the measurement spots of the denaturing reaction cavity 38, the immunoassay cavity 43, and the agglutinative reaction cavity 46 to electrically access and read a reactant at the measurement spot via the electrode. The same logic shall apply regardless of whether the reactant is a liquid, a solid, or a semisolid substance such as a jelly-like substance or a gel-like substance.

Due to such an arrangement, while surplus blood remains in the area of the sample solution overflow cavities 25 and 26 after measurement completion, by forming the capacity of the capillary area of the sample solution overflow cavity 26 so as to be equal to or greater than the surplus blood, surplus blood is held and trapped by the capillary force of the sample solution overflow cavity 26. Therefore, surplus blood can be suppressed from flowing out from the air duct 20d formed circumferentially inwards with respect to the sample solution overflow cavity 26 to the outside of the analysis device 1, thereby enabling a reduction in the risk of operators being involved in contamination accidents.

In addition, while a sample whose blood cell component has been diluted by a diluent remains in the area of the diluent overflow cavity 29 that is a measurement spot after measurement completion, since the threshold 28 that restricts a channel to a size that enables action of capillary force has been formed, the sample is prevented from flowing out from the diluent overflow cavity 29 to the overflow cavity 27. As a result, the diluted blood cell component can be prevented from flowing out from the air duct 20f positioned circumferentially inwards with respect to the diluent overflow cavity 29 to the outside of the analysis device 1, thereby enabling a reduction in the risk of operators being involved in contamination accidents.

Figure 49:
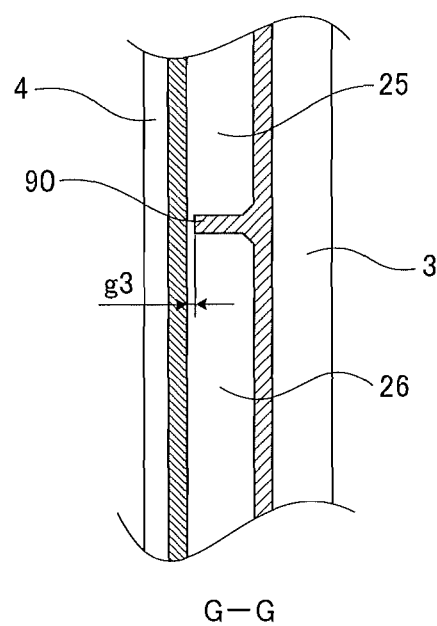
FIG. 49 is a cross-sectional view of another example of overflow cavities 25 and 26.

In the embodiment described above, on the side of the sample solution overflow cavities 25 and 26 which hold surplus blood, the sample solution overflow cavity 26 is formed as a capillary area in which capillary force acts in order to suppress blood outflow. However, an alternative configuration is possible in which: cross-sectional dimensions of the sample solution overflow cavity 25 and the sample solution overflow cavity 26 in the thickness directions are both formed to a size where capillary force does not act; a threshold 90 similar to the threshold 28 formed on the boundary of the diluent overflow cavity 29 and the overflow cavity 27 is provided on the boundary of the sample solution overflow cavity 25 and the sample solution overflow cavity 26 as shown in FIG. 49; and the overflow channel gap is restricted to g3 where capillary force acts.

Figure 50:
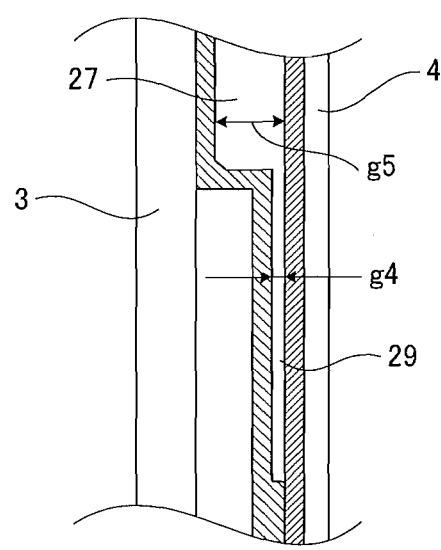
FIG. 50 is a cross-sectional view of another example of a measurement spot 29.
Figure 51A:
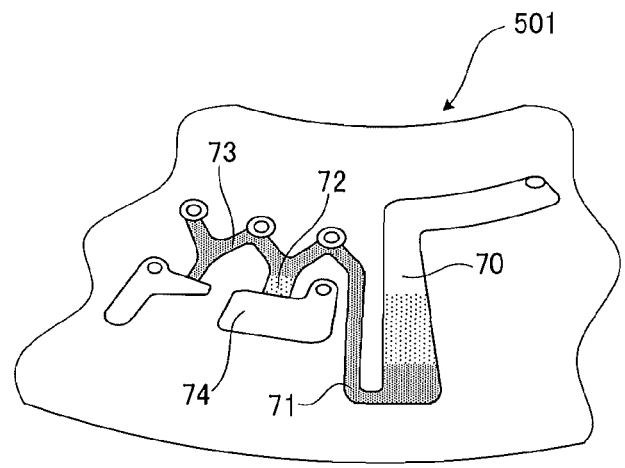
FIG. 51A is a plan view of a substantial part of an analysis device according to Patent Document 1.
Figure 51B:
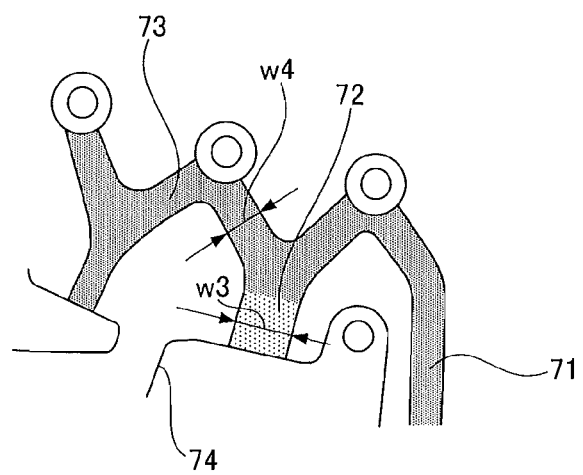
FIG. 51B is an enlarged view of a substantial part of an analysis device according to Patent Document 1.
Figure 52A:
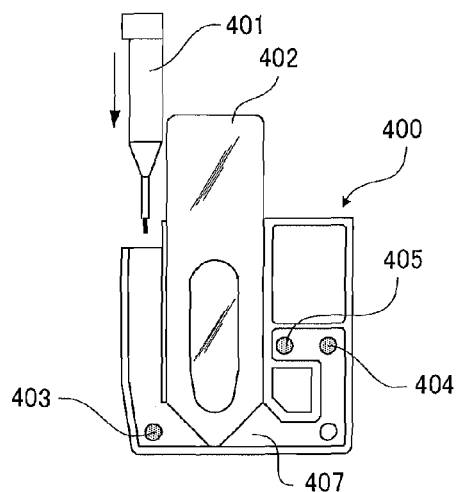
FIG. 52A is an explanatory diagram with respect to Patent Document 2.
Figure 52B:
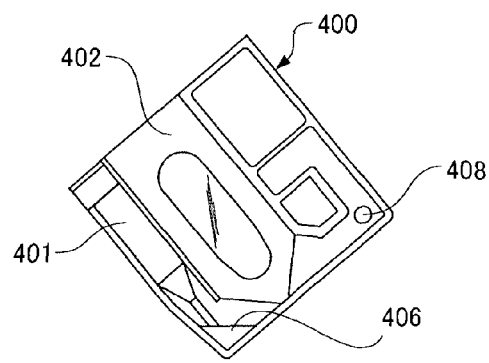
FIG. 52B is an explanatory diagram with respect to Patent Document 2.
Figure 52C:
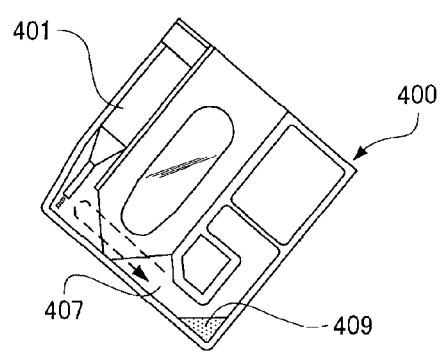
FIG. 52C is an explanatory diagram with respect to Patent Document 2.
Figure 53:
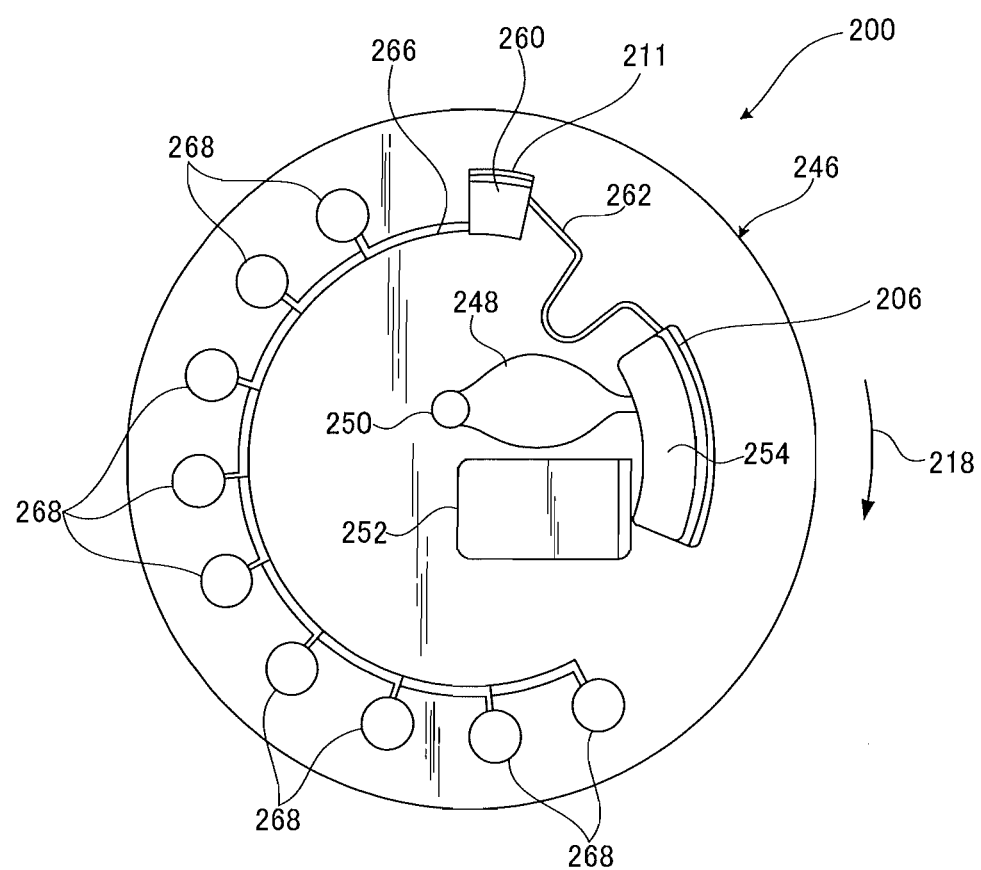
FIG. 53 is a plan view illustrating an analysis device according to Patent Document 3.
Figure 54:
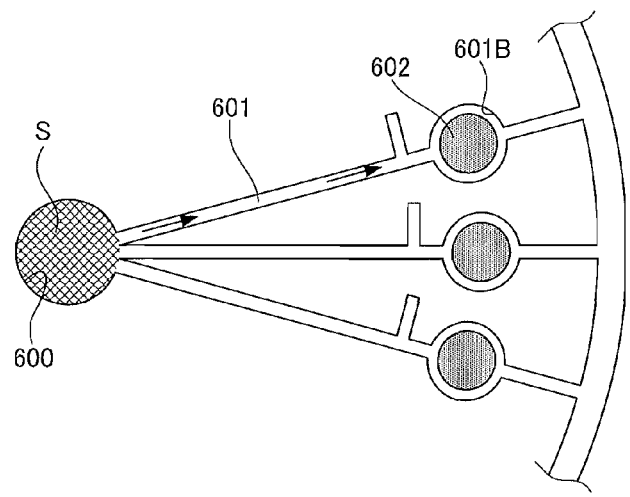
FIG. 54 is a plan view of an analysis device according to Patent Document 4.
Figure 55:
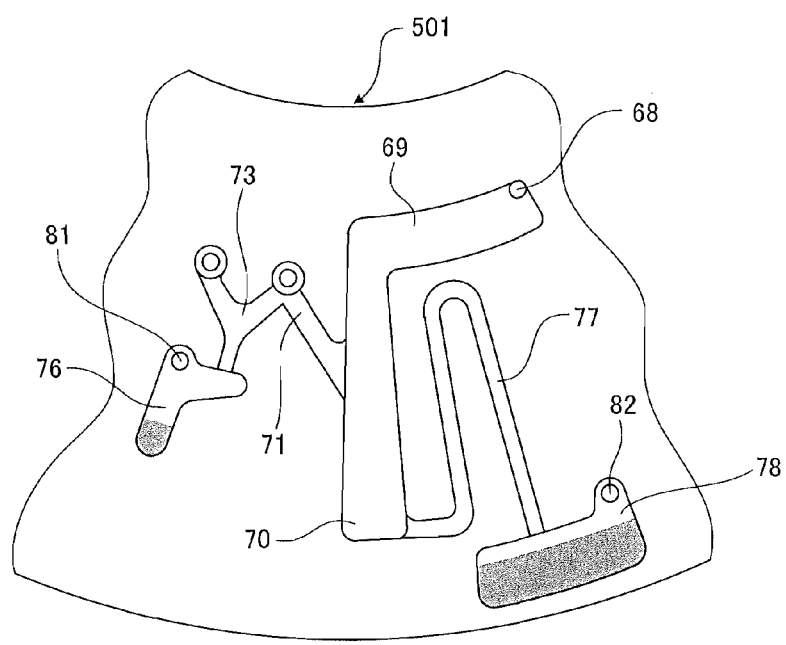
FIG. 55 is a plan view of a substantial part of an analysis device according to Patent Document 1.

In the embodiment described above, while the threshold 28 is formed between the diluent overflow cavity 29 holding a diluted blood cell component and the overflow cavity 27 to suppress sample overflow, as seen in the sample solution overflow cavity 26, an alternative configuration is possible in which the cross-sectional dimension g4 of the diluent overflow cavity 29 in the thickness direction is set smaller than the cross-sectional dimension g5 of the overflow cavity 27 in the thickness direction as shown in FIG. 50 so that the diluent overflow cavity 29 becomes a capillary area in which capillary force acts.

While the case of the diluent overflow cavity 29 has been described above as an example, the same logic applies to the case of the agglutinative reaction cavity 46 as a measurement spot. By arranging the connecting channel 45 provided circumferentially inwards with respect to the diluent overflow cavity 29 as a gap in which capillary force acts so as to prevent sample liquid from flowing out from the diluent overflow cavity 29 into the immunoassay quantitative cavity 44 as a capillary cavity, the sample liquid can be prevented from flowing out from the air duct 20i, thereby enabling protection of operators from risk.

Furthermore, while a light-emitting diode is used as a light source in the present embodiment, the present invention is not limited to this arrangement. Moreover, as for light source wavelength in regards to colorimetry, a wavelength region having an optical absorption property of hemoglobin will suffice and a y peak (Soret absorption band) having an optical absorption property in a range from 400 to 450 nm or an optical absorption property of a visible part of hemoglobin or a hemoglobin derivative which has an absorption property in a range from 500 to 580 nm may be used. With respect to turbidity, while absorption occurs in the visual light range, a range of 500 to 800 nm is suitable.

Figure 24:
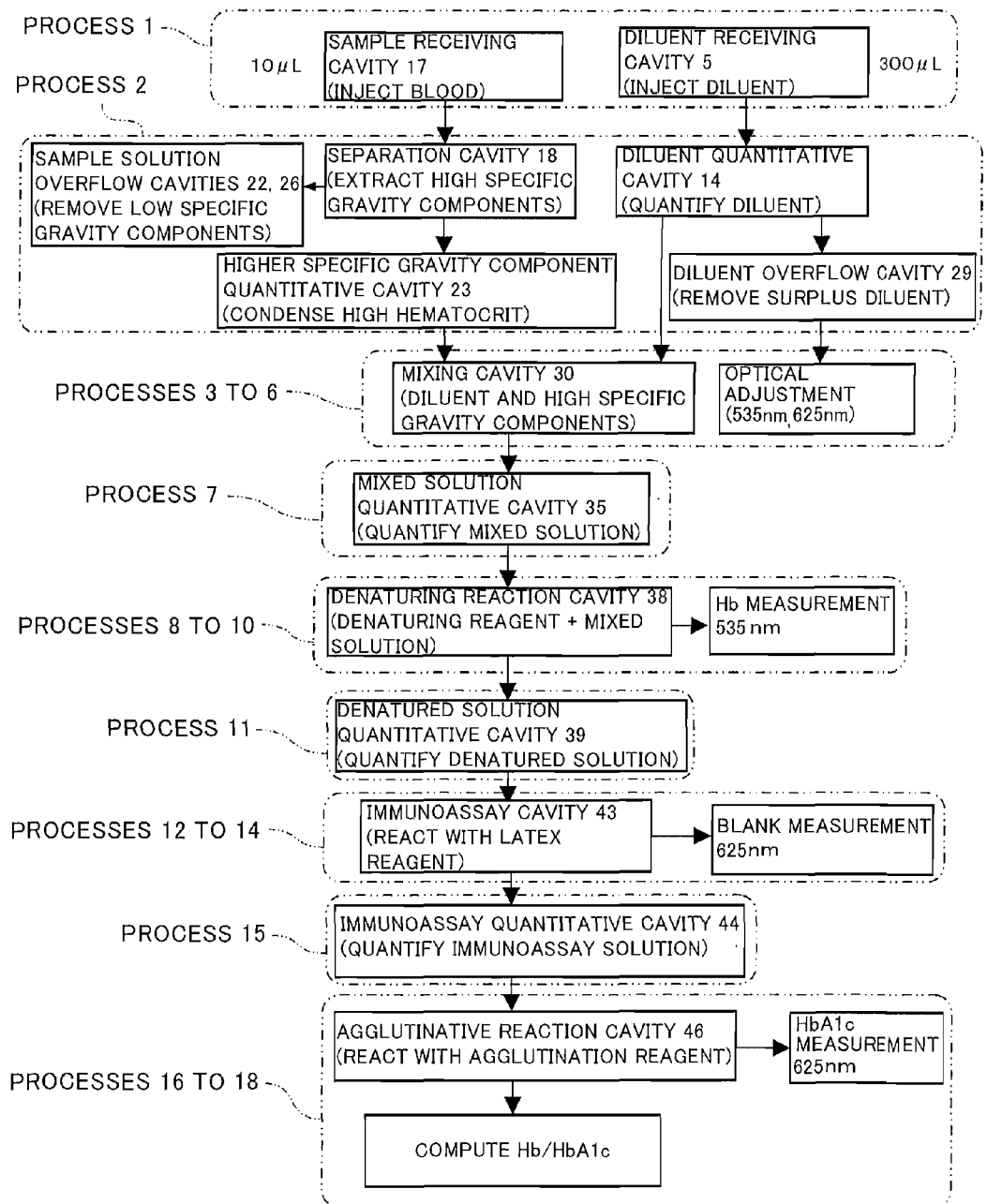
FIG. 24 is a detailed configuration diagram of an analysis device according to an embodiment of the present invention.

FIG. 24 illustrates the processes 1 to 18 described above in greater detail than FIG. 13.

A more detailed description will now be given on a hemoglobin derivative measurement performed with a reagent held in the analysis device 1.

A hemoglobin derivative measurement method that is an embodiment of the present invention includes a process in which a hemoglobin derivative in the sample is denatured by a denaturing reagent (denaturant).

Hemoglobin (hereinafter also referred to as Hb) is basically a tetrameric structure formed when alpha-chain and non-alpha-chain (beta, gamma, and delta chains) globin bind and associate with heme. A wide variety of hemoglobin types exist, notably including HbA1 in which binding occurs with glucose, acetaldehyded Hb due to alcohol consumption, and carbamoylated Hb seen in dialysis patients and the like. As shown, hemoglobin derivatives represent modifications of partial regions of hemoglobin which result in different structures, and include HbA (alpha 2 and beta 2) which accounts for approximately 90% of all hemoglobin derivatives, HbA2 (alpha 2 and delta 2) which accounts for approximately 3%, and HbF (alpha 2 and gamma 2) which accounts for approximately 1%. HbA includes HbA0 in which glucose does not bind to a beta chain amino-acid terminus and HbA1 in which glucose binds to a beta chain amino-acid terminus. Furthermore, HbA1 includes HbA1a, HbA1b, and HbA1c, which are also hemoglobin derivatives. In particular, hemoglobin A1c in which blood glucose binds to a beta chain N-terminal of hemoglobin is well known as an index reflecting blood glucose concentration levels over the previous two to three months.

A hemoglobin derivative is determined by whether an amino-acid sequence exists in a specific region of a peptide structure or whether there is a phosphorylated or glycated region in an amino-acid residue or a peptidic terminus. For example, a beta chain N-terminal is phosphorylated in HbA1a, a beta chain N-terminal is aldehyded in HbA1b, and a beta chain N-terminal is fructosylated in HbA1c. In addition, with HbF, subunits differ between beta and gamma. In units of amino acids, the 9th residue and the 21st residue from the N-terminal of the beta subunit of HbA2 differ. A hemoglobin derivative as used in the present invention refers to a structure in which a partial region differs as described above. There are a wide variety of hemoglobin derivatives in addition to aforementioned acetaldehyde-hemoglobin adducts due to alcohol abuse and urea-hemoglobin adducts existing in the blood of uremic patients, such as aspirin-hemoglobin complexes and carboxymethylated hemoglobin. While glycated hemoglobin that is generated by a nonenzymatic reaction between a reactive amine group on hemoglobin protein and glucose is generally cited as a useful measurement item for hemoglobin derivatives, the present invention is not limited thereto.

When measuring hemoglobin derivatives as shown in the present invention, slightly different regions of the hemoglobin derivatives must be distinguished and recognized to identify and quantify each hemoglobin derivative. In the present invention, extracting such different portions or, in other words, extracting a specific location of a hemoglobin derivative from the inside of a protein structure to the outside of the structure is referred to as denaturation.

Denaturation may occur at a degree where: a subunit structure that makes up a quaternary structure becomes disassociated; a hydrophobic bonding, a hydrogen bonding, van der Waals' force, or ionic bonding that makes up a tertiary structure becomes disassociated; the structure of an alpha helix or a beta sheet that makes up a secondary structure is altered; or a linear structure is formed. Generally, protein exists in vivo as a functional substance because a precise three-dimensional structure formed by the structures described above is retained. Therefore, varying the structure can be described as varying the function and characteristics of a protein to a certain degree. This includes both improvements and degradations of functions. Denaturants to be used for varying structures include, but are not limited to, a method in which hemoglobin is denatured by a lithium salt-form negative ion (Japanese Patent Laid-Open No. 03-051759) and a method including a nonionic surfactant (WO 2006/112339).

A reagent for immunoassay according to the present embodiment is a reagent containing an antibody specific to a denatured portion of a hemoglobin derivative and any measurement principle based on an immunoassay antigen-antibody reaction according to the present invention shall suffice, including any of generally known turbidimetric immunoassay, nephelometric immunoassay, latex immune agglutination, immune agglutination inhibition, latex immune agglutination inhibition, fluorescence immunoassay, chemiluminescent immunoassay, electrochemical immunoassay, fluorescence polarization immunoassay, and immunochromatography.

With a hemoglobin derivative measurement method according to the present invention, an immunoassay utilizing an antibody specific to a glycated portion of a hemoglobin derivative is particularly important. As described earlier, glycated hemoglobin include HbA1a, HbA1b, and HbA1c. In particular, among the three, HbA1c is used as an indicator for managing patients with diabetes which has now become a major issue as one of three major adult diseases and can provide an indication of long-term blood glucose control over one to three months. Specifically, following a denaturation of HbA1c, immunoassay includes a reagent containing an antibody with respect to glycated amino acid at a beta chain N-terminal specific to HbA1c.

An agglutinative agent for agglutination according to the present embodiment is an agglutination multivalent antigen that causes a specific antigen-antibody reaction with an antibody and is not limited to that described above as long as an immunoassay reaction is achieved which is measured using an antibody on a specific location of a hemoglobin derivative.

Methods of holding a reagent according to the present invention are not limited to a liquid state, a dried substance state, a freeze-dried substance state, and the like, and any practically significant method can be adopted.

Next, hemoglobin A1c that is a representative examination item of hemoglobin derivatives will be described more specifically in examples 1 to 8 presented below and with reference to FIGS. 25 to 29 and Tables 1 to 6.

Example 1

As an example of an implementation of the present invention, a reagent composition when an evaluation is performed by HbA1c latex agglutination inhibition will be described. In addition, in the present example, an antibody is to be used labeled to a latex bead.

(a) Preparation of Monoclonal Antibody

Preparation of Immunogen

Preparation of a HbA1c immunogen was carried out as follows. First, when preparing a structure equivalent to a beta chain N-terminal portion of HbA1c, by binding fructose to valine of a polypeptide structured such that amino acids are bound in a sequence of valine-histidine-leucine-threonine-cysteine (hereinafter abbreviated as VHLTC), a fructosyl HVLTC was prepared. Next, in order to enhance immunogenicity, a condensing reagent N-(6-Maleimidocaproyloxy) succinimide was used via a cysteine residue of the fructosyl VHLTC to label an amino group of chicken gamma globulin (hereinafter abbreviated as CGG), whereby an obtained fructosyl VHLTC-labeled CGG was to be used as an immunogen.

1. Immunization of Mice

10 μg of the immunogen (fructosyl VHLTC-labeled CGG) prepared as described above was emulsified and injected into the respective peritoneal cavities of 10 mice (Balb/c) approximately eight-week-old. The immunization procedure was repeated at two-week intervals.

2. Verification of Antibody Production 50 to 100 μL of blood was collected from the ophthalmic veins of mice subjected to five immunization procedures into a centrifuging tube. After centrifugal separation of serum, an antibody titer evaluation by ELISA confirmed that an anti-HbA1c antibody was produced in all mice.

3. Boosting of Mice

Boosting (injection of a weak immunogen) was performed on mice revealed to have a particularly high titer by the aforementioned antibody titer evaluation in order to enlarge the spleens of the mice. A solution obtained by diluting 10 μg of fructosyl VHLTC-labeled CGG with PBS was used as the immunogen.

4. Cell Fusion

Spleen cells of mice three days after boost were removed and fused with mouse myeloma-derived cells by a common procedure using polyethyleneglycol. The fused cells were cultured on a HAT medium containing 15% fetal calf serum (hereinafter FCS) on a 96-well culture plate. A week later, the medium was replaced with an HT medium containing 15% FCS.

5. Cloning

Antibody titer measurement was performed by ELISA to select wells with high titers.

Dilution (limiting dilution) was performed to a concentration where one cell is contained per well, whereby the diluted material was dispensed to a 96-well microplate. Culture was performed using increasingly large plates. Antibody titer measurement by ELISA was repeatedly performed at appropriate timings. A cell group having a high titer with respect to HbA1c and presenting favorable growth was eventually selected.

6. Freeze Preservation of Cells

The ultimately selected cells were frozen at a concentration of $3 \times 10^6$ cells/mL at $-80°$ C. and then transferred into liquid nitrogen for long-term preservation.

7. Evaluation of Antibody

Ascites fluid was prepared by an ordinary method involving intraperitoneally injecting mice with the obtained cells. Antibodies were purified using a column filled with a protein A-Sepharose gel. For the antibodies obtained in the manner described above, the half value of fructosyl VHLTC-labeled CGG that inhibits the bonding of the respective aforementioned antibodies with respect to hemoglobin A1c coating the ELISA plates (half value of inhibition) was $2 \times 10^{-10}$ M of a monoclonal antibody derived from a strain represented by International Patent Organism Depositary accession number PERM BP-10795 (international deposit), National Institute of Advanced Industry Science and Technology.

(b) Latex Reagent

The aforementioned purified antibodies were labeled by physical adsorption using 0.15 μm polystyrene latex manufactured by Sekisui Chemical Co., Ltd. and by performing agitation for two hours at cavity temperature. Subsequently, blocking was performed in a 0.5% BSA (manufactured by Sigma-Aldrich Co.)/PBS suspension liquid, unlabeled antibodies were then separated and cleansed by centrifugal separation and subsequently re-suspended in a 0.5% BSA (manufactured by Sigma-Aldrich Co.)/PBS suspension liquid to obtain antibody latex reagents.

(c) Agglutination Reagent cobas (registered trademark) reagent (synthetic multivalent HbA1c antigen) manufactured by Roche Diagnostics K.K. was used as the agglutination reagent.

(d) Denaturing Reagent

The following composition was determined based on a method including a nonionic surfactant (WO2006/112339).

1. Sucrose monocaprate (Wako Pure Chemical Industries, Ltd.)/concentration during reaction 0.25%

2. Potassium ferricyanide (Wako Pure Chemical Industries, Ltd.)/concentration during reaction 0.25%

(e) Diluent

Pure water prepared by a general ion exchange method was used as the diluent.

Example 2

Hereinafter, an example of an evaluation of hemoglobin concentration measurement will be described in detail.
(a) Preparation Method of Analysis Device An analysis device was prepared by having the immunoassay cavity 43, the agglutinative reaction cavity 46, and the denaturing reaction cavity 38 of the analysis device according to the embodiment described above respectively hold the latex reagent, the agglutination reagent, and the denaturing reagent described in Example 1 by freeze-drying.
(b) Preparation of Mixed Solution A sample solution (blood) was prepared by diluting collected human blood using pure water.

Hb concentration of the mixed solution was determined using "Hemoglobin B-Test Wako" commercially marketed by Wako Pure Chemical Industries, Ltd. This is a hemoglobin detection method that employs an SLS-hemoglobin method.
(c) Hb Measurement by Analysis Device Using the analysis device holding the reagents, an injection hole was drilled at an upper portion of the mixing cavity 30. After directly injecting the mixed solution, the injection hole was sealed. Subsequently, the analysis device 1 was mounted on the analysis apparatus main body 100, whereby transfer was performed from the mixing cavity 30 to the denaturing reaction cavity 38 precisely as described in Example 1 and an absorbance value of 535 nm was detected after a reaction of 1 minute with the denaturing reagent.

Figure 25:
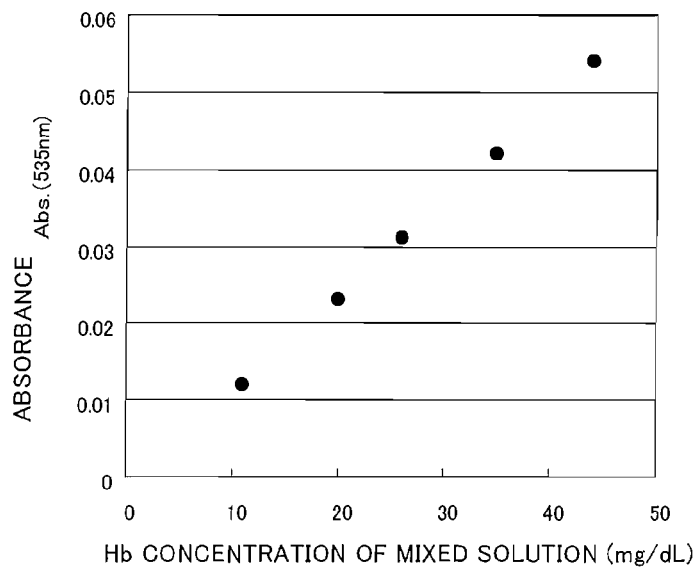
FIG. 25 is a relationship diagram of hemoglobin concentration and absorbance according to Example 2.

In FIG. 25, hemoglobin concentration of the mixed liquid is plotted on the abscissa and absorbance is plotted on the ordinate. As a result, from the present method, it is revealed that the values of Hb concentration and absorbance have a proportional relationship when Hb concentration is within a range of 0 to 50.0 mg/dL. This suggests that Hb measurement in correspondence with Hb concentration is highly feasible.

Example 3

Hereinafter, an example of an evaluation of glycated hemoglobin (HbA1c) measurement will be described in detail.
(a) Preparation Method of Analysis Device: As Described in Example 2
(b) Preparation of Mixed Solution A mixed liquid with a known glycated hemoglobin concentration was prepared by diluting, with pure water, a 24.6 µM glycated hemoglobin standard solution enclosed with cobas reagent glycated hemoglobin commercially marketed by Roche Diagnostics K.K.
(c) Glycated Hemoglobin Measurement by Analysis Device Using the analysis device holding the reagents, an injection hole was drilled at an upper portion of the mixing cavity 30. After directly injecting the mixed solution, the injection hole was sealed. Subsequently, the analysis device 1 was mounted on the analysis apparatus main body 100, whereby transfer was performed from the mixing cavity 30 to the denaturing reaction cavity 38 precisely as described in Example 1. In the respective transfer processes, an 1-minute reaction between the denaturing reagent and the mixed solution was performed in the denaturing reaction cavity 38, a latex blank (turbidity) after a reaction of 2 minutes with the latex reagent was measured at 625 nm in the immunoassay cavity 43, and finally, agglutination turbidity (turbidity) when an agglutination reaction was performed was measured at 625 nm. A variance in agglutination turbidity was calculated from the latex blank.

Figure 26:
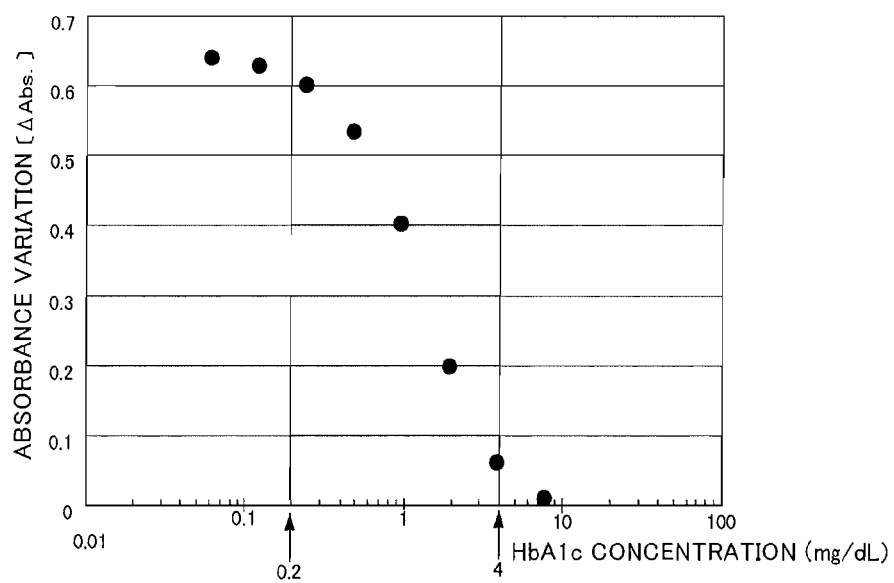
FIG. 26 is a relationship diagram of HbA1c concentration and absorbance variation according to Example 3.

FIG. 26 is a diagram in which glycated hemoglobin concentration is plotted on the abscissa thereof and absorbance variation is plotted on the ordinate thereof. Conversion of glycated hemoglobin concentration from mol to mg/dL was calculated by setting hemoglobin molecular weight to 64500. As a result, from the present method, it is revealed that the values of HbA1c concentration and absorbance have a substantially proportional relationship when HbA1c concentration is within a range of 0.1 to 10.0 mg/dL (more favorably, from 0.2 to 4.0 mg/dL). This suggests that glycated hemoglobin measurement is highly feasible.

Example 4

Hereinafter, an example of a measurement of an abundance ratio of glycated hemoglobin/Hb will be described in detail.
(a) Preparation Method of Analysis Device: As Described in Example 2
(b) Preparation of Sample Solution Three types of whole blood was used as the sample solution. In addition, Table 1 presents results of glycated hemoglobin (%) of the blood samples as measured with an automatic glycated hemoglobin analyzer (HLC-723 GHbV), Tosoh Corporation, which is widely used in glycated hemoglobin measurement and which employs HPLC as a principle.

TABLE 1

|  | Specimen 1 | Specimen 2 | Specimen 3 |
| --- | --- | --- | --- |
| Glycated hemoglobin [%] | 4.8 | 7.6 | 11.2 |

(c) Measurement by Analysis Device

The three types of blood samples and the diluent were respectively injected into the sample receiving cavities of the analysis device 1. The analysis device 1 was mounted on the analysis apparatus main body 100, the liquids were transferred, and by measuring the absorbance of the hemoglobin derivative at 535 nm and the turbidity thereof at 625 nm, the latex blank and the degree of agglutination were measured by absorbance. Hemoglobin concentration was determined by calculating the concentration of hemoglobin contained in the denatured solution from FIG. 25 based on measured absorbance and on the hemoglobin concentration plot according to Example 2. In addition, glycated hemoglobin concentration was determined by calculating the concentration of glycated hemoglobin contained in the agglutinated solution 63 from FIG. 26 based on the variance in turbidity. The results thereof are presented in Table 2.

TABLE 2

|  | Specimen 1 | Specimen 2 | Specimen 3 |
| --- | --- | --- | --- |
| Hb concentration in mixed solution [mg/dL] | 25.6 | 24.6 | 22.2 |
| Concentration of glycated hemoglobin in mixed solution [mg/dL] | 1.21 | 1.86 | 2.46 |
| Glycated hemoglobin [%] | 4.7 | 7.6 | 11.1 |

According to Table 2, the result of measurement of the proportions occupied by glycated hemoglobin with the present analysis device 1 closely resembles the result (refer to Table 1) of measurement of the proportions occupied by glycated hemoglobin with the automatic glycated hemoglobin analyzer (HLC-723 GHbV), Tosoh Corporation, which was performed in advance. Therefore, it was confirmed that the present analysis device 1 is capable of accurately measuring glycated hemoglobin concentration.

Example 5

Hereinafter, an example of an evaluation of diluent quantification will be described in detail.

(a) Preparation Method of Analysis Device

In order to recreate evaporation of the diluent during storage, 300 µL of the diluent was held in the analysis device and stored for two months in environments of 4° C., 15° C., 25° C., and 45° C. Subsequently, the immunoassay cavity 43, the agglutinative reaction cavity 46, and the denaturing reaction cavity 38 of the analysis device were respectively arranged so as to hold the latex reagent, the agglutination reagent, and the denaturing reagent described in Example 1 by freeze-drying. For this example, for comparison, a siphon channel directly connected with the mixing cavity 30 was prepared as a comparative example (not illustrated) in place of the siphon channel connected to the diluent quantitative cavity 14.

Analysis Results

Figure 27:
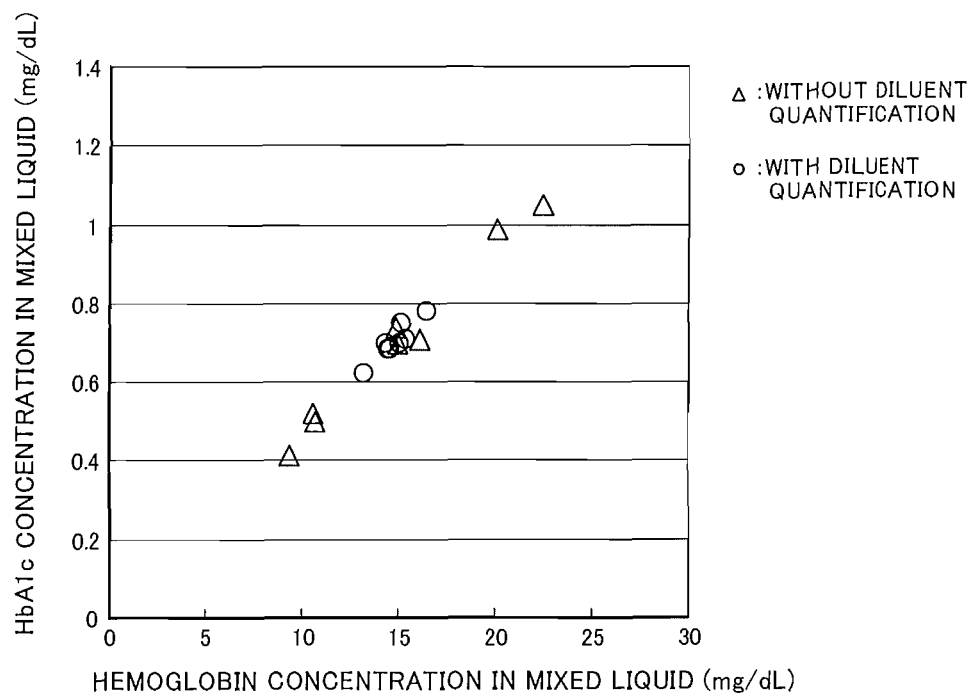
FIG. 27 is a relationship diagram of Hb values and glycated hemoglobin values in a mixed solution depending on whether or not diluent quantification is performed according to Example 5.

A sample was injected into the analysis device 1 prepared by the method of Example 2. Abundance ratio of glycated hemoglobin/Hb was measured based on Example 4. The Hb values and glycated hemoglobin values of the respective measurement results are illustrated in FIG. 27. Table 3 presents the reproducibility of the abundance ratios of glycated hemoglobin/Hb.

TABLE 3

Glycated hemoglobin measurement values

|   | Without diluent quantification | With diluent quantification |
|---|---|---|
| 1 | 4.7% | 4.9% |
| 2 | 4.7% | 4.7% |
| 3 | 5.0% | 4.7% |
| 4 | 4.9% | 4.7% |
| 5 | 4.4% | 4.6% |
| 6 | 4.4% | 4.6% |
| 7 | 4.7% | 4.9% |
| 8 | 4.9% | 4.7% |
| Average | 4.7% | 4.7% |
| C.V. | 4.8% | 2.4% |

When dilution quantification was performed, HbA1c concentration ranges from 0.6 to 0.8 mg/dL when Hb concentration is within 13.0 to 17.0 mg/dL. On the other hand, when dilution quantification was not performed, HbA1c concentration ranges from 0.4 to 1.0 mg/dL when Hb concentration is within 10.0 to 22.0 mg/dL. Therefore, the variance in Hb values is smaller as compared to not performing dilution quantification. Furthermore, while the measured CV value when not performing dilution quantification is 4.8%, the measured CV takes a value of 2.4 when dilution quantification is performed, thereby confirming an improvement in the reproducibility of the abundance ratios of glycated hemoglobin/Hb.

Example 6

Hereinafter, an example of an evaluation of the effectiveness of a sample solution separation process prior to the reactions of the sample solution with the respective reagents will be described in detail.

An analysis device was prepared as described in Example 2.

Four types of sample blood (specimens A, B, C, and D) with different Hb concentrations of 4.0 mg/dL, 7.1 mg/dL, 13.7 mg/dL, and 20.9 mg/dL were prepared by varying the blood plasma quantity of a same specimen (glycated hemoglobin 4.8%) to be used for analysis. The respective Hb concentrations were assayed using Sysmex KX-21. Assay values and Hb concentrations in mixed solutions when performing/not performing a separation process are presented in Table 4, Table 5, and Table 6.

TABLE 4

Hb measurement results

| Specimen | Specimen Hb [g/dL] | Hb concentration in mixed liquid without condensing process [mg/dL] | Hb concentration in mixed liquid after condensing process [mg/dL] |
|---|---|---|---|
| Specimen A | 4 | 7.8 | 12.5 |
| Specimen B | 7.1 | 14.1 | 28.4 |
| Specimen C | 13.7 | 27.4 | 36.1 |
| Specimen D | 20.9 | 41.6 | 45.3 |

TABLE 5

Glycated hemoglobin measurement results

| Specimen | Specimen Hb [g/dL] | Glycated hemoglobin concentration in mixed liquid without condensing process [mg/dL] | Glycated hemoglobin concentration in mixed liquid after condensing process [mg/dL] |
|---|---|---|---|
| Specimen A | 4 | 0.30 | 0.60 |
| Specimen B | 7.1 | 0.72 | 1.39 |
| Specimen C | 13.7 | 1.34 | 1.73 |
| Specimen D | 20.9 | 2.00 | 2.13 |

TABLE 6

Glycated hemoglobin/Hb abundance ratios

| Specimen | Specimen Hb [g/dL] | Glycated hemoglobin concentration in mixed liquid without condensing process [%] | Glycated hemoglobin concentration in mixed liquid after condensing process [%] |
|---|---|---|---|
| Specimen A | 4 | 3.8 | 4.8 |
| Specimen B | 7.1 | 5.1 | 4.9 |
| Specimen C | 13.7 | 4.9 | 4.8 |
| Specimen D | 20.9 | 4.8 | 4.7 |

First, when a separation process was not performed, the Hb concentrations of the mixed solutions of the specimens A, B, C, and D respectively took values of 7.8 mg/dL, 14.1 mg/dL, 27.4 mg/dL, and 41.6 mg/dL as presented in Table 4, while the HbA1c concentrations thereof respectively took values of 0.30 mg/dL, 0.72 mg/dL, 1.34 mg/dL, and 2.00 mg/dL as presented in Table 5. Consequently, as presented in Table 6, HbA1c/Hb abundance ratios of 3.8%, 5.1%, 4.9%, and 4.8% were respectively obtained.

On the other hand, when a separation process according to the present example was included, the Hb concentrations of the mixed solutions of the specimens A, B, C, and D respectively took values of 12.5 mg/dL, 28.4 mg/dL, 36.1 mg/dL, and 45.3 mg/dL as presented in Table 4, while the HbA1c concentrations thereof respectively took values of 0.60 mg/dL, 1.39 mg/dL, 1.73 mg/dL, and 2.13 mg/dL as presented in Table 5. Consequently, as presented in Table 6, HbA1c/Hb abundance ratios of 4.8%, 4.9%, 4.8%, and 4.7% were respectively obtained.

From these observations, it is shown that the inclusion of the separation process results in values closely resembling the glycated hemoglobin concentration of 4.8% of the original mixed solution and those highly accurate results can be obtained.

This implies that even with specimen A and specimen B having extremely low Hb concentrations, performing a separation process such as that described in the present example enables condensation to maintain high concentrations and suppresses the adverse effects of low concentrations on the measurement system. As a result, the Hb/glycated hemoglobin abundance ratios of specimens which were not measurable when a separation process was not performed can now be carried out in an accurate manner.

Example 7

Figure 28:
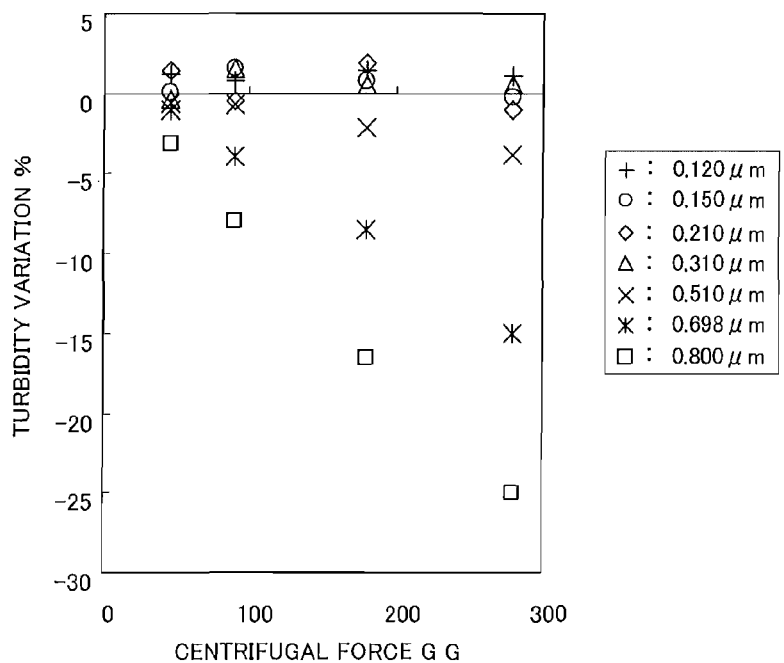
FIG. 28 is a relationship diagram of variations in turbidity before and after centrifuge of latex particles according to Example 7.

FIG. 28 illustrates the results of the degrees of variations in turbidity of 0.12 μm to 0.8 μm latex particles prior to centrifugation and after 5-minute centrifugations respectively at 45 G to 180 G as measured by microspectrophotometer MSV-350, JASCO Corporation. Latex particles whose sizes equal or exceed 0.8 μm are significantly affected by sedimentation due to centrifugal force and have reduced turbidities. It is obvious that the degrees of incidence are heavily reliant on particle size. This also applies to latex average particle sizes after agglutination.

In this case, a variation in turbidity can be calculated as

Turbidity variation(%)=(turbidity after centrifugation/
turbidity before centrifugation)×100.

Example 8

Figure 29:
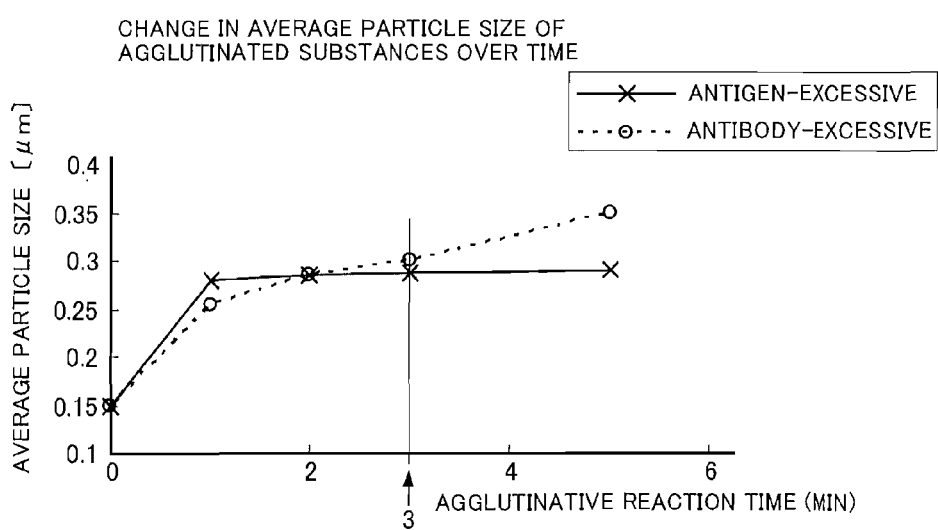
FIG. 29 is a diagram illustrating variations in average particle size over time after subjecting a latex particle sensitized with an antibody to an agglutination reaction according to Example 8.

FIG. 29 illustrates the results of a measurement of average particle sizes performed after an agglutinative reaction of latex particles with particle sizes of 0.15 nm sensitized by an antibody as measured by a granulometer (Zetasizer Nano, SYSMEX CORPORATION). The results show that, three minutes after reaction, the average particle sizes of the agglutinated substances fall within double the latex particle sizes prior to agglutination. In addition, with an agglutinative reaction in which the mixing ratio of latex reagent-sensitized antibodies and the antigen within the agglutination reagent is antigen-excessive, the average particle size preferably does not increase with time, thereby enabling particle size control of the agglutinative reaction to be performed more rigidly. Furthermore, FIG. 28 indicates that as long as the average particle size of the agglutinated substances is equal to or less than 700 nm, the influence to absorbance when setting centrifugal force to or lower than 200 G and measurement time to 1 minute is equal to or less than 2%, thereby enabling high accuracy measurement.

As seen, with an analysis method using the analysis device according to the present invention, a process in which a quantification of a diluent and a quantification of a mixed solution can be accurately performed and the separation process that reliably separates a small amount of the sample solution into a blood plasma component (low specific gravity component) and a blood cell component (high specific gravity component) are provided. In addition, transfer sequences during measurement and channel patterns of the analysis device can be simplified. Consequently, colorimetric measurement or turbidimetric measurement using an agglutination inhibition reaction such as an immunoreaction can be performed with high accuracy. In particular, concentrations of hemoglobin derivatives (e.g., hemoglobin A1c) can be measured with high accuracy.

In addition, by reducing the individual variations in hemoglobin concentration in whole blood using a blood separation mechanism, measurements of various specimens can be performed and measurement accuracy can be increased.

Furthermore, measurements of blood components can be performed within the analysis device in a simple and speedy manner without being affected by procedures performed by operators.

Second Embodiment

Specific examples of the shapes of a denaturing reaction cavity 38, an immunoassay cavity 43, and an agglutinative reaction cavity 46 will now be described with reference to FIGS. 30A, 30B to 32, and 33.

Figure 30A:
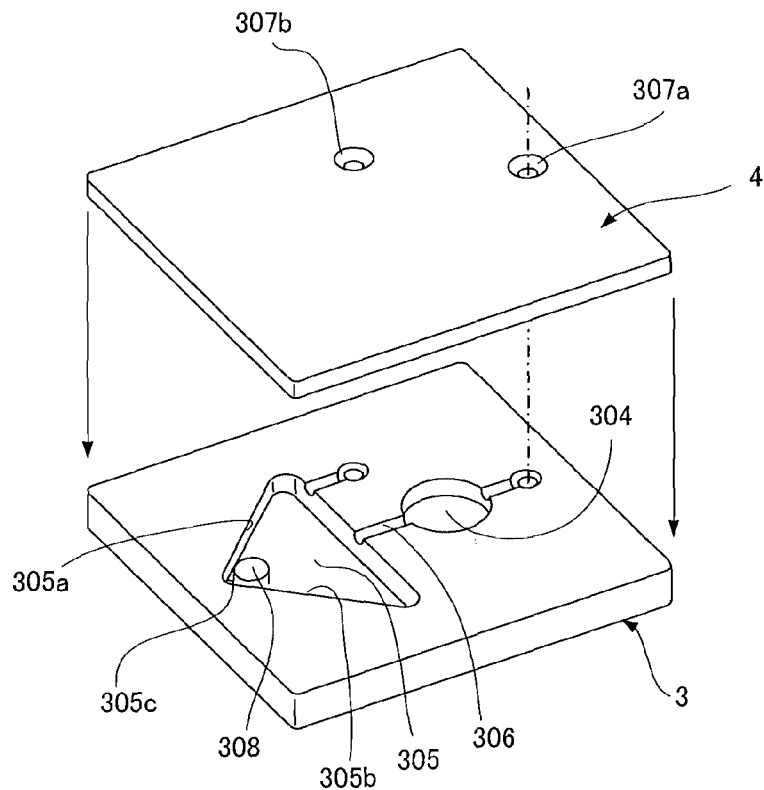
FIG. 30A is an exploded perspective view of an analysis device according to a second embodiment of the present invention.
Figure 30B:
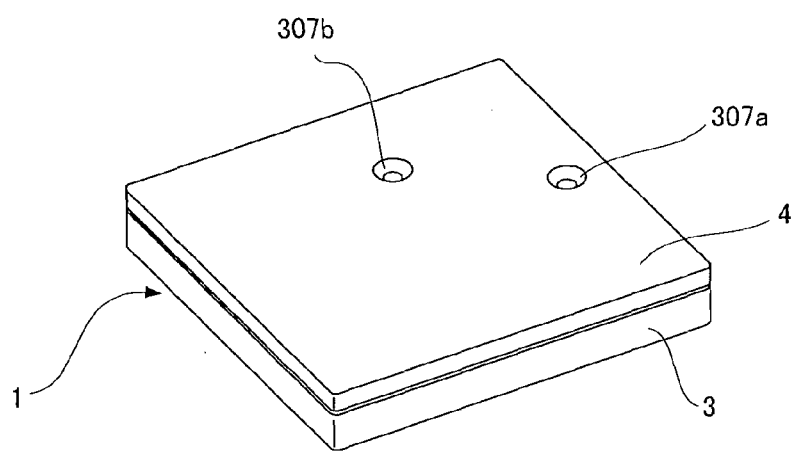
FIG. 30B is an external view of an analysis device according to the second embodiment of the present invention.

FIGS. 30A and 30B illustrate an analysis device.

As illustrated in FIG. 30A, an analysis device 1 is made up of a base substrate 3 and a cover substrate 4 that closes and covers an upper face of the base substrate 3. A holding cavity 304, an operation chamber 305, and a connecting channel 306 that connects the holding cavity 304 and the operation chamber 305 are formed on the base substrate 3. Air ducts 307a and 307b for air intake/exhaust are formed on the cover substrate 4.

Upon bonding the base substrate 3 to the cover substrate 4, a reagent 308 is set in advance in the operation chamber 305. A sample liquid 309 has been injected into the holding cavity 304.

Figure 31:
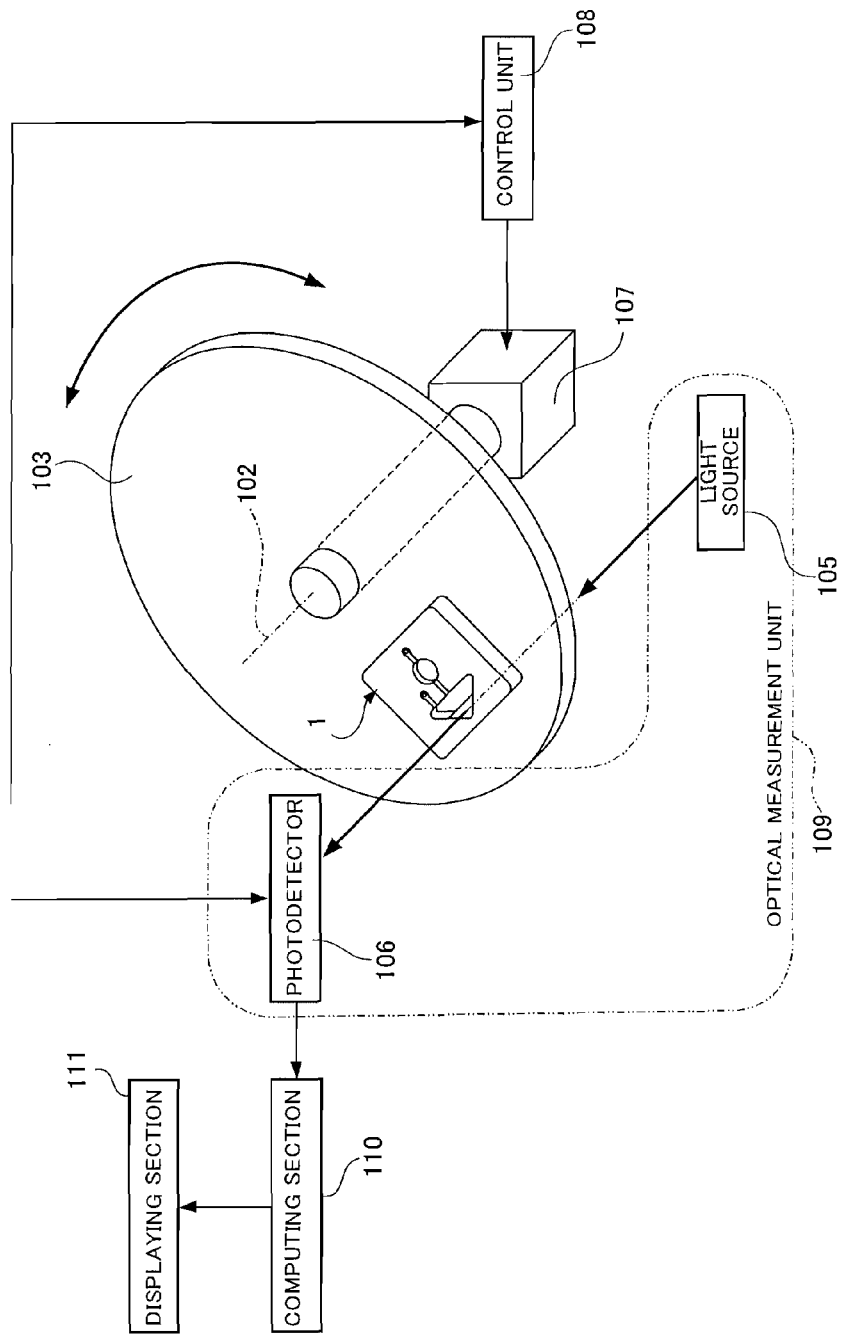
FIG. 31 is a configuration diagram of an agitation apparatus according to the second embodiment of the present invention.

As illustrated in FIG. 31, the analysis device 1 is set on an inclined rotor 103 such that the holding cavity 304 is positioned on the side of an axial center 102 of the rotor 103 and the operation chamber 305 is positioned on the outer circumferential side of the rotor 103. A rotation driving unit 107 rotates the rotor 103 around the axial center 102 so as to cause centrifugal force to act on the analysis device 1. Alternatively, for example, a motor that repetitively rotates the rotor at a predetermined angle to perform a swinging operation may be used. Note that the cover substrate 4 is not depicted in FIG. 31.

The air ducts 307a and 307b perform intake or exhaust of air so as to enable the sample liquid 309 to be transferred from the holding cavity 304 to the operation chamber 305 by centrifugal force. This is because, while transferring the sample liquid 309 requires that air flow from a transfer source into a transfer destination, the connecting channel 306 is filled with the sample liquid 309 and air cannot be moved without the air duct 307a.

In addition, the air ducts 307a and 307b are disposed towards the axial center 102 as compared to the operation chamber 305 so as to prevent the sample liquid 309 from passing through the air duct 307a and scattering to the outside.

The operation chamber 305 is shaped such that the far-side (outer circumference, to be described later) width on the opposite side of the connecting channel 306 gradually tapers. Wall faces 305a and 305b in a direction that intersects with the rotational direction of the rotor 103 intersect at an outer circumferential portion of the analysis device 1 to form a tip portion 305c of the operation chamber 305.

The configuration will now be described based on an analysis process in which the analysis device 1 described above is set on an analysis apparatus.

First, the sample liquid 309 is held by the holding cavity 304. Centrifugal force is generated as the rotation driving unit 107 rotates the rotor 103. The sample liquid 309 is transferred by the connecting channel 306 from the holding cavity 304 to the operation chamber 305. The transferred sample liquid 309 flows into the tip portion 305c of the operation chamber 305 and immerses the reagent 308. The rotation driving unit 107 performs a swinging operation, causing the sample liquid 309 and the reagent 308 to be mixed in the operation chamber 305.

The force that acts on the mixed liquid in the operation chamber 305 during the swinging operation will now be described.

Figure 32:
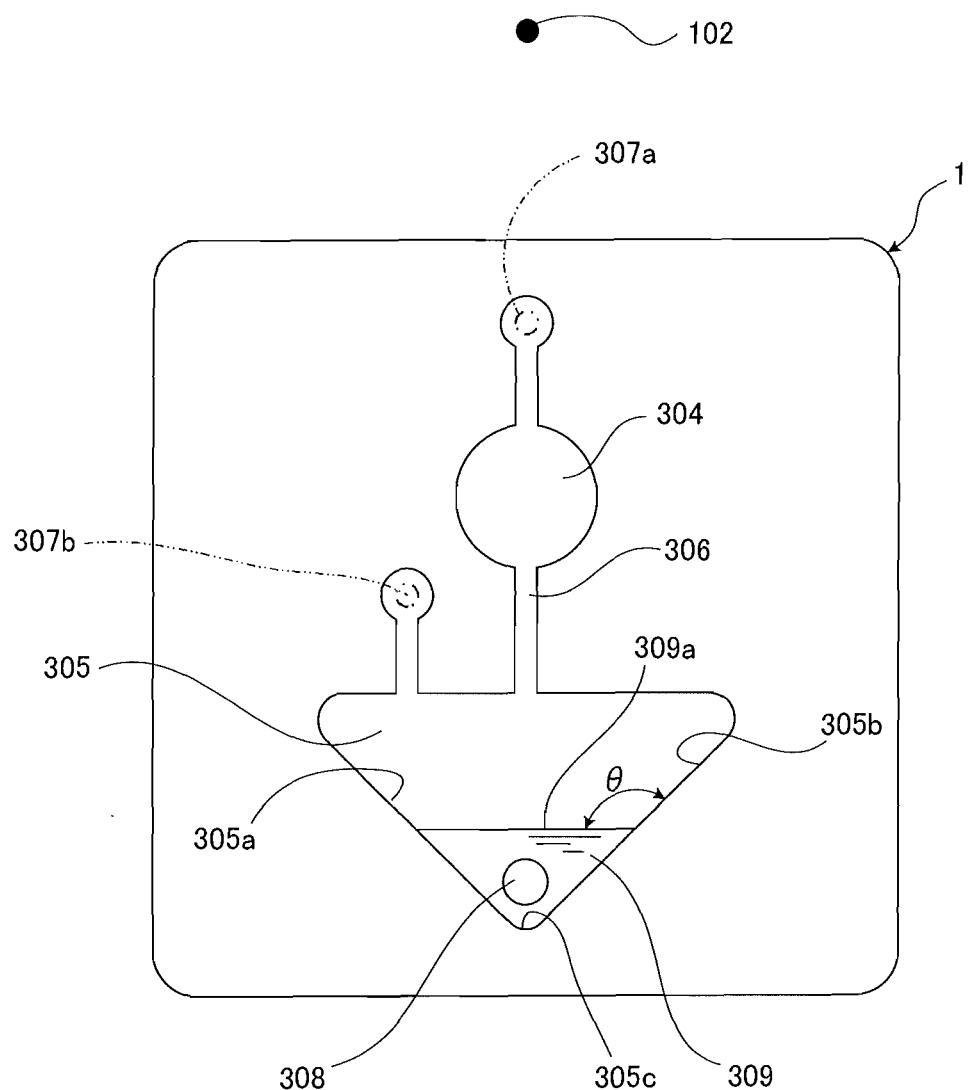
FIG. 32 is a perspective view of an operation chamber according to the second embodiment of the present invention.
Figure 33:
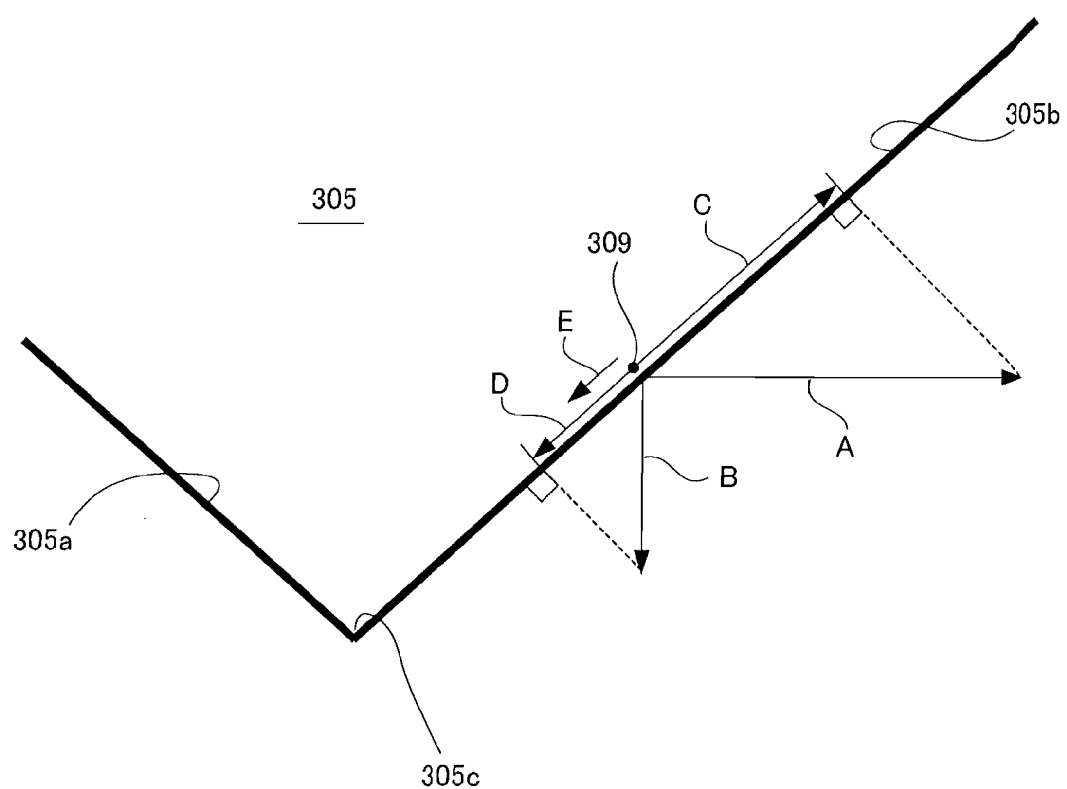
FIG. 33 is a diagram illustrating force acting on a liquid reagent during an swinging operation according to the second embodiment of the present invention.

FIG. 32 is a plan view omitting the cover substrate 3 and which illustrates the analysis device during a swinging operation and a liquid surface 309a of the sample liquid 309 having flowed into the operation chamber 305. FIG. 33 illustrates the wall faces 305a and 305b of the operation chamber 305 illustrated in FIG. 32. A force to be described below acts on the sample liquid 309 in the operation chamber 305 from the wall face 305b. The same logic applies to the wall face 305a.

Acceleration A that is generated during acceleration/deceleration of rotation and centrifugal force B act on the sample liquid 309 which comes into contact with the wall face 305b during a swinging operation. These two forces can be replaced with forces on an inclined surface, namely, an acceleration component force C and a component force D of the centrifugal force. In addition, a surface tension E acts on the sample liquid 309. Consequently, the force acting on the sample liquid 309 at this point is a sum of the acceleration component force C, the surface tension E, and the component force D of the centrifugal force.

In FIG. 33, since the acceleration component force C is greater than the sum of the surface tension E and the component force D of centrifugal force, the sample liquid 309 moves in the direction of the acceleration component force C.

Therefore, conditions of the inclined wall faces 305a and 305b are preferably set such that a liquid surface-wall face angle θ formed by the liquid surface 309a of the sample liquid 309 trapped between the inclined wall faces 305a and 305b (the tip portion 305c) and the inclined wall faces 305a and 305b enables the acceleration component force C to become greater than the sum of the component force D of the centrifugal force and the surface tension E and oriented in an inner circumferential direction.

Specifically, when the liquid surface-wall face angle θ is 90 degrees, the acceleration component force C becomes 0 and the component force D of centrifugal force becomes equal to the centrifugal force B. While the sample liquid 309 attempts to move in an outer circumferential direction, the sample liquid 309 is unable to do so because the sample liquid 309 is trapped in the tip portion 305c. In addition, when the liquid surface-wall face angle θ is smaller than 90 degrees, the acceleration component force C and the component force D of centrifugal force become oriented in an outer circumferential direction. While the sample liquid 309 attempts to move in an outer circumferential direction, the sample liquid 309 is unable to do so because the sample liquid 309 is trapped in the tip portion 305c.

In comparison, in the present second embodiment, since the liquid surface-wall face angle θ is formed so as to be greater than 90 degrees, when the acceleration component force C is greater than the sum of the surface tension E and the component force D of centrifugal force, the sample liquid 309 can now move in the direction of the acceleration component force C. The greater the liquid surface-wall face angle θ over 90 degrees, the smaller the acceleration required by agitation.

Furthermore, the lengths of the inclined wall faces 305a and 305b must extend more circumferentially inwards compared to the liquid surface 309a so as to enable sufficient movement by the sample liquid 309 during a swinging operation.

As shown, according to the present second embodiment, by forming inclined wall faces 305a and 305b which spread at a predetermined angle so as to form the tip portion 305c in an outer circumferential direction of the operation chamber 305, the sample liquid 309 can sufficiently move inside the operation chamber 305 in the direction of rotation during a swinging operation and a configuration can be achieved in which the reagent 308 can be sufficiently immersed in the sample liquid 309 even with a small amount of liquid. Therefore, the reagent 308 can be sufficiently dissolved and mixed even when the amount of the sample liquid 309 is small.

In addition, since a sharp tip portion 305c results in a certain amount of the sample liquid 309 adhering to the tip and staying immobilized even when performing a swinging operation, it is further preferable to remove sharp tips and form the tip portion 305c using curved faces. Specifically, the R radius of the tip portion 305c of the operation chamber 305 was preferably 1 to 3 mm with respect to a depth of 3 mm. The R radius can be optionally varied depending on the amount of liquid and on the depth, shape, and surface state of the chamber.

Agitation can be performed with greater efficiency by performing water-repelling treatment on the wall faces 305a and 305b of the operation chamber 305. Methods of water-repelling treatment include coating and deposition with a water repellent on the inside of the operation chamber 305. In addition, the use of water-repelling material such as polypropylene, polyethylene, fluorine contained resin and the like as the material of the base substrate 3 is an effective way to obtain a water-repelling effect.

In particular, by subjecting the inclined wall faces 305a and 305b and the vicinity thereof to water-repelling treatment, the surface tension E of the wall faces of the operation chamber 305 and the sample liquid 309 can be reduced, thereby enabling agitation to be performed with a smaller acceleration A.

Furthermore, since a surfactant is included in the reagent 308, the surface tension E of the wall faces of the operation chamber 305 and the sample liquid 309 can be reduced and agitation can be performed with a smaller force.

Moreover, since a surfactant is included in the sample liquid 309, the surface tension E of the wall faces of the operation chamber 305 and the sample liquid 309 can be reduced and agitation can be performed with a smaller acceleration A.

In FIG. 31, the analysis apparatus main body 100 is configured as described below.

The analysis apparatus main body 100 is made up of: a rotation driving unit 107 that drives the rotor 103; an optical measurement unit 109 that optically measures a solution in the analysis device 1; a control unit 108 that controls the rotational speed and rotational direction of the rotor 103, the measurement timing of the optical measurement unit 109, and the like; a computing section 110 for processing a signal obtained by the optical measurement unit 109 and computing a measurement result; and a displaying section 111 for displaying the result obtained by the computing section 110. The optical measurement unit 109 includes: a light source 105 that irradiates light to the tip portion 305c of the operation chamber 305; and a photodetector 106 that detects a light intensity of transmitted light having passed through the analysis device 1 among the light irradiated from the light source 105.

Specific examples of arranging the denaturing reaction cavity 38, the immunoassay cavity 43, and the agglutinative reaction cavity 46 so as to hold reagents will now be described with reference to FIGS. 34A, 34B to 47A, and 47B to 47E. By arranging reagents to be held as shown by the specific examples, an optical path length can be measured accurately even if a reagent is being held at a measurement spot in a manufacturing stage. As a result, improvements in measurement accuracy can be expected.

Third Embodiment

FIGS. 34A, 34B to 38A, and 38B illustrate a third embodiment of the present invention.

Figure 34A:
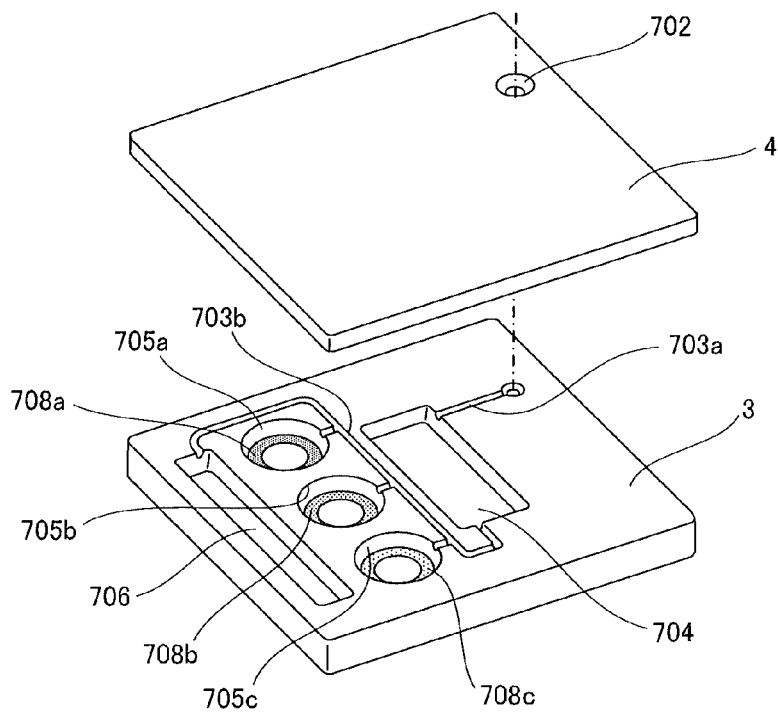
FIG. 34A is an exploded perspective view of an analysis device according to a third embodiment of the present invention.
Figure 34B:
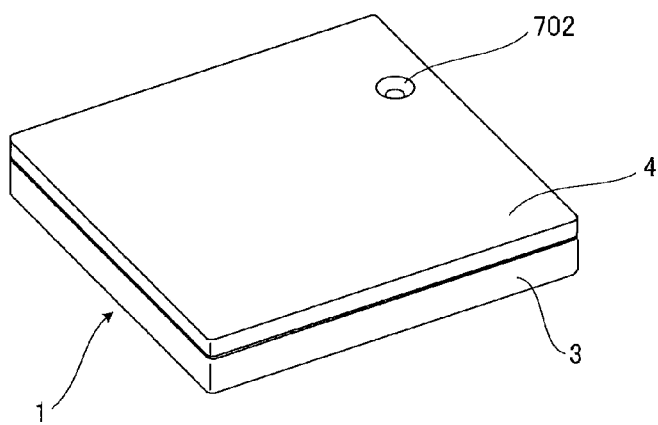
FIG. 34B is an assembly perspective view of an analysis device according to the third embodiment of the present invention.

As illustrated in FIGS. 34A and 34B, an analysis device according to the present third embodiment is configured such that a base substrate 3 and a cover substrate 4 are bonded to each other. A holding cavity 704 for temporarily storing a sample liquid, a plurality of measurement spots 705a, 705b, and 705c for optically detecting color reactions between the sample liquid and reagents, and an overflow cavity 706 for trapping surplus sample liquid are formed on the bonding surface of the base substrate 3 and the cover substrate 4. The respective chambers are formed by closing off openings of depressions formed on the base substrate 3 with the cover substrate 4. Reference character 703a denotes a first channel that transfers a sample liquid received from a sample liquid inlet 702 of the cover substrate 4 to the holding cavity 704; and reference character 703b denotes a second channel that transfers the sample liquid from the holding cavity 704 to the measurement spots 705a, 705b, and 705c and to the overflow cavity 706 and which is formed by closing off an opening of a depression formed on the base substrate 3 with the cover substrate 4.

The base substrate 3 and the cover substrate 4 are bonded together after having depressions of the base substrate 3 to become the measurement spots 705a, 705b, and 705c hold reagents 708a, 708b, and 708c using an adhesive material such as an UV adhesive, a hot-melt, a double-stick tape, or the like. Alternatively, portions of the base substrate 3 and the cover substrate 4 may be melted and joined using a laser or ultrasound.

Figure 35:
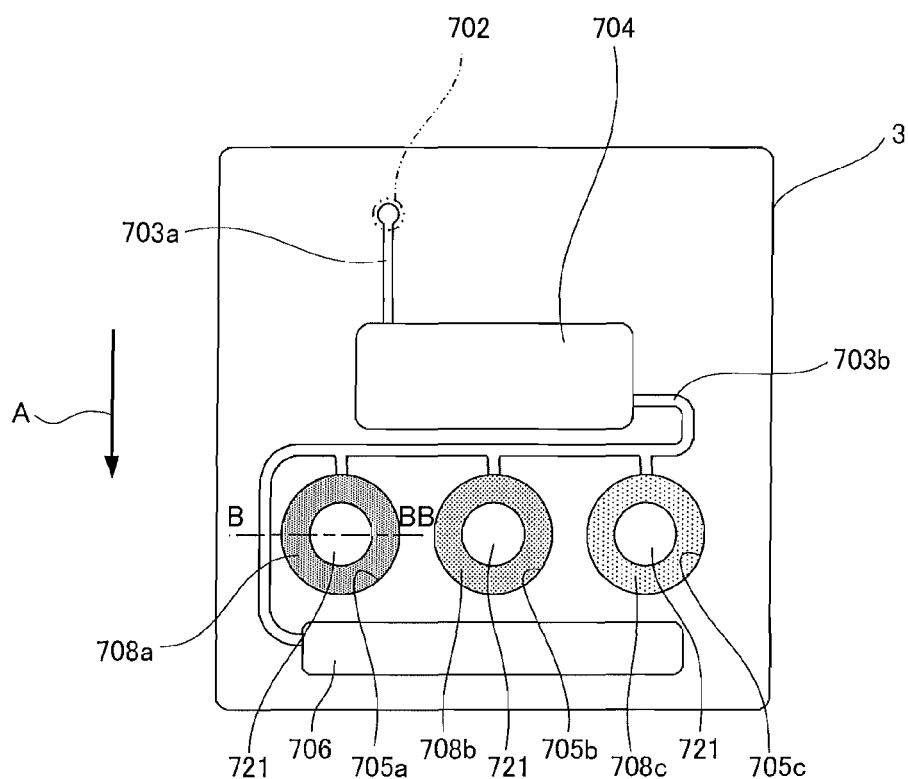
FIG. 35 is a plan view of a base substrate according to the third embodiment of the present invention.
Figure 36:
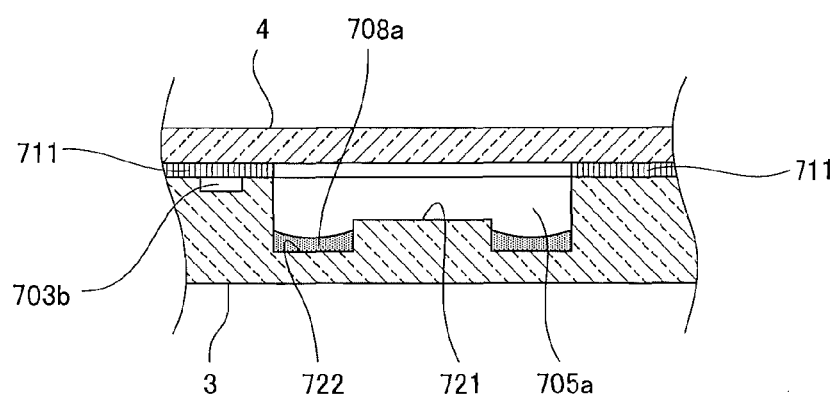
FIG. 36 is an enlarged cross-sectional view of a substantial part taken along line B-BB of FIG. 35.

FIG. 35 illustrates details of the base substrate 3, while FIG. 36 illustrates a cross section denoted by B-BB in FIG. 35 of the vicinity of the measurement spot 705a after the base substrate 3 and the cover substrate 4 are bonded together with an adhesive layer 711.

An analysis region 721 that is set higher than the periphery thereof is formed at the center of the bottom face of the depression that is the measurement spot 705a. The reagent 708a is held in a groove surrounding the analysis region 721. The grooved portion thus becomes a reagent holding region 722 adjacent to the analysis region 721.

The depressions that are the measurement spots 705b and 705c are formed in the same manner. The reagent 708b held in a groove surrounding the analysis region 721 of the measurement spot 705b differs in type from the reagent 708a. The reagent 708c held in a groove surrounding the analysis region 721 of the measurement spot 705c differs in type from the reagents 708a and 708b.

Figure 37A:
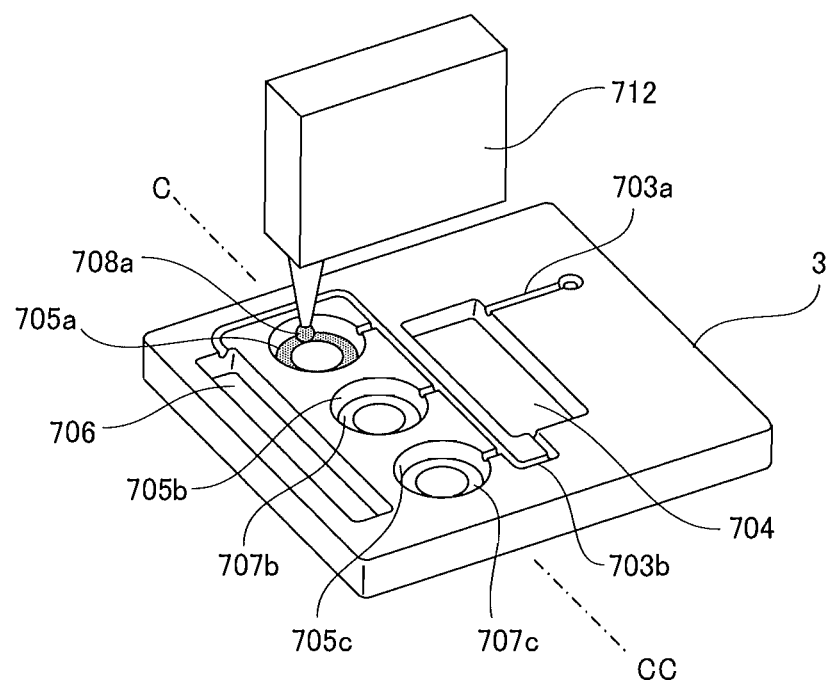
FIG. 37A is a perspective view of a reagent applying process according to the third embodiment of the present invention.

FIG. 37A illustrates a process for having the groove surrounding the analysis region 721 hold the reagent 708. A reagent dispenser 712 drops a necessary amount of the liquid reagent 708a onto the reagent holding region 722. Subsequently, cold curing or freeze-drying is performed to solidify and fix the dropped liquid reagent 708a.

Figure 37B:
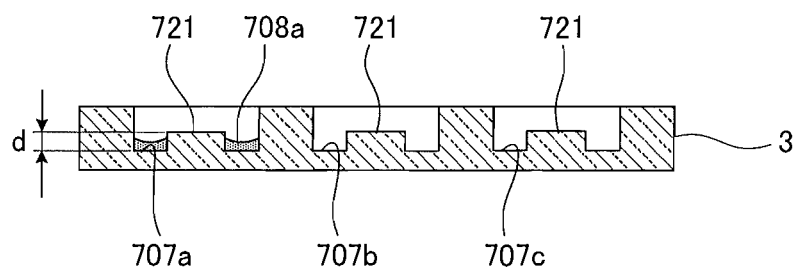
FIG. 37B is a C-CC cross-sectional view of a reagent applying process according to the third embodiment of the present invention.

FIG. 37B illustrates a C-CC cross section of FIG. 37A. Reagents can be favorably held if the depth d of grooves 707a, 707b, and 707c to become reagent holding regions of the respective measurement spots 705a, 705b, and 705c is equal to or greater than 50 μm. The reagents 708b and 708c are respectively held by the groove 707b of the measurement spot 705b and the groove 707c of the measurement spot 705c in a similar manner.

The respective analysis regions 721 of the measurement spots 705a, 705b, and 705c are favorably subjected to hydrophobic treatment in advance so as to ensure that reagents do not adhere to the analysis regions 721 when the reagents 708a, 708b, and 708c are being held by the reagent holding regions 722.

An optical path length of each analysis region 721 of the measurement spots 705a, 705b, and 705c of the analysis device 1 in which reagents are held as described above is measured using laser light. An obtained measured value of the optical path length is converted into a barcode as analysis device information and is printed by the analysis device.

Figure 38A:
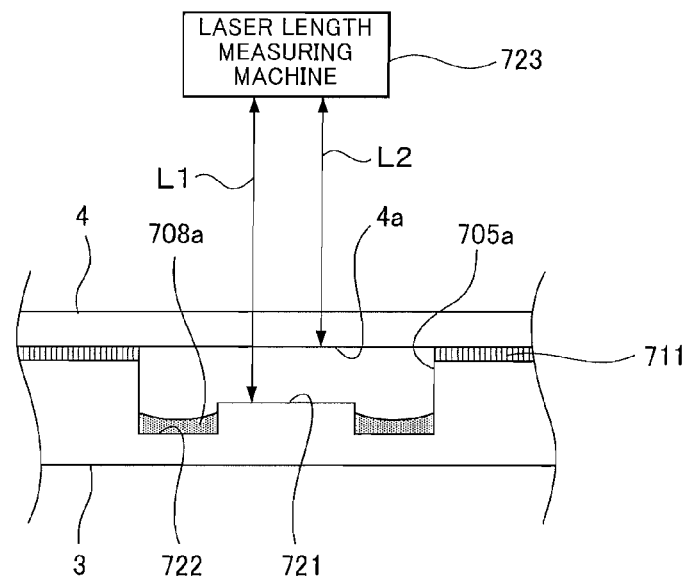
FIG. 38A is a cross-sectional view describing a relationship between a mixed liquid of a reagent and a sample liquid and optical path lengths according to the third embodiment of the present invention.

When performing optical path length measurement from the side of the cover substrate 4 as illustrated in FIG. 38A, the cover substrate 4 is to be formed by a material which transmits the wavelength of the laser light outputted from a laser length measuring machine 723 as well as a light of a wavelength of a light source such as a light-emitting diode that is used during analysis by an analysis apparatus to be described later. Although the base substrate 3 need not transmit light of the aforementioned wavelength, a constant intensity of light incident to a light receiving section must be secured in order to detect color reactions during analysis by the analysis apparatus.

At this point, if L1 denotes the measured distance of the analysis region 721 detected by the laser length measuring machine 723 and L2 denotes the measured distance of an inward face 4a of the cover substrate 4 detected by the laser length measuring machine 723, then an optical path length (L1-L2) is converted into a barcode and printed by the analysis device.

When color reactions are reflectively measured during analysis by the analysis apparatus using a material that does not transmit light as the base substrate 3, it is required that aluminum or the like is deposited on the faces of the respective analysis regions 721 so as to have light transmitted through the measurement spots reflected to the side of the cover substrate 4 and detected by a light receiving section positioned on the side of the cover substrate 4. Alternatively, both the base substrate 3 and the cover substrate 4 can be made of light-transmitting material.

Figure 38B:
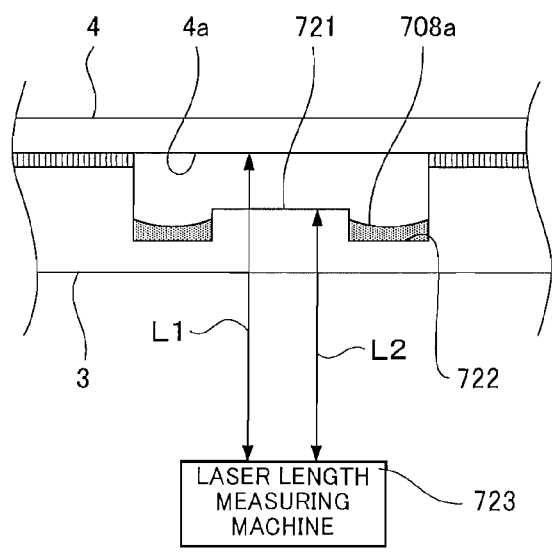
FIG. 38B is a cross-sectional view describing a relationship between a mixed liquid of a reagent and a sample liquid and optical path lengths according to the third embodiment of the present invention.

When performing optical path length measurement from the side of the base substrate 3 as illustrated in FIG. 38B, the base substrate 3 must be made of a material which transmits the wavelength of the laser light used for measurement as well as a light of a wavelength of a light source that is used during analysis by the analysis apparatus. While the cover substrate 4 need not transmit light, when using a material that does not transmit light for the cover substrate 4, it is required that aluminum or the like is deposited on the cover substrate 4 to enable light transmitted through the measurement spots to be reflected to the side of the base substrate 3 so as to be detected by a light receiving section positioned on the side of the base substrate 3. Alternatively, both the base substrate 3 and the cover substrate 4 can be made of light-transmitting material.

At this point, if L2 denotes the measured distance of the analysis region 721 detected by the laser length measuring machine 723 and L1 denotes the measured distance of the inward face 4a of the cover substrate 4 detected by the laser length measuring machine 723, then an optical path length (L1-L2) is converted into a barcode and printed by the analysis device.

Methods of recording analysis device information are not limited to barcodes. The analysis device can alternatively be configured so that a data carrier such as an IC tag on which is recorded optical path length information is attached to the analysis device.

An analysis process is executed as follows using the analysis device 1 arranged so as to hold reagents as described above.

A blood plasma component of blood or the like is used as the sample liquid. A constant amount of a blood plasma component of blood separated by a centrifugal separation machine is extracted by a micropipette and injected through the sample liquid inlet 702. The sample liquid injected through the sample liquid inlet 702 is transferred by a capillary action to the holding cavity 704. Subsequent transfer operations and analysis of sample liquids are performed inside the analysis apparatus after inserting the analysis device into the analysis apparatus.

As illustrated in FIG. 5, the analysis device 1 is set on a rotor 103 of an analysis apparatus main body 100 at a positioned separated from an axial center 102 of the rotor 103. Reference numeral 104 denotes a motor that drives the rotor 103 around the axial center 102 and is mounted inclined by an angle of θ with respect to a vertical direction. Holes 51 and 52 are provided and positioned on the rotor 103 so that light outputted from a light source 105 is transmitted through the positions of the respective analysis regions 721 of the measurement spots 705a, 705b, and 705c of the analysis device 1 set on the rotor 103 to be detected by a photodetector 106.

The rotation of the rotor 103 generates a centrifugal force in the direction of the arrow A as illustrated in FIG. 35, causing the sample liquid inside the holding cavity 704 to be transferred and carried to the measurement spots 705a, 705b, and 705c.

Figure 39:
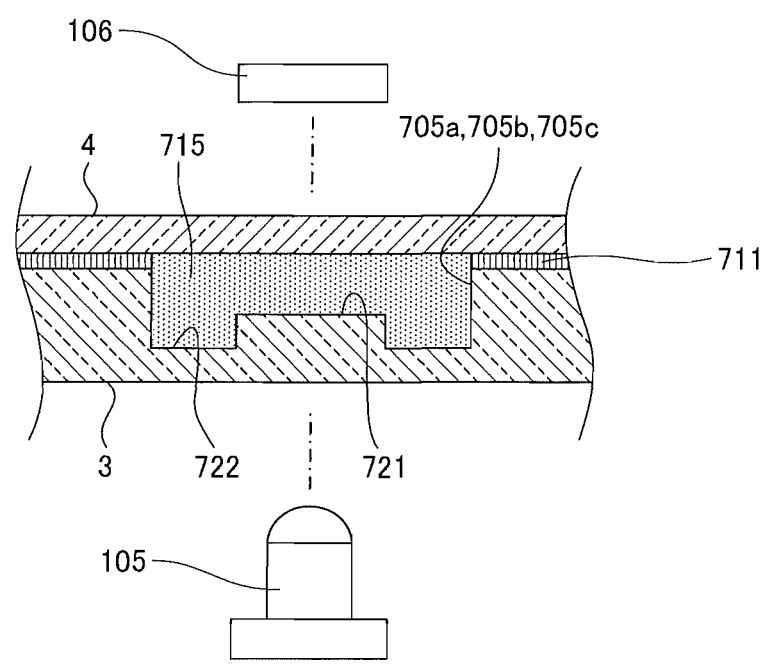
FIG. 39 is a cross-sectional view illustrating an analysis being performed by an analysis apparatus in which is set an analysis device according to the third embodiment of the present invention.

As the sample liquid flows into the measurement spots 705a, 705b, and 705c, the reagents 708a, 708b, and 708c are dissolved by the sample liquid and color reactions occur according to the components thereof. At this point, as illustrated in FIG. 39, the analysis region 721 must be filled in the direction of an optical path length by a mixed liquid 715 of a reagent and the sample liquid such that no gaps are created by air bubbles. When an air bubble is present in a measurement spot, it is necessary to ensure that the analysis region 721 is filled by the mixed liquid 715 and that no gaps occur in the direction of an optical path length by gathering the mixed liquid 715 in one direction using centrifugal force generated by rotation. The analysis apparatus main body 100 executes reading when passing between the light source 105 and the photodetector 106 in a state where the analysis regions 721 of the respective measurement spots 705a, 705b, and 705c are filled with the mixed liquid 715. The concentration of a specific component in the sample liquid is computed from an absorbance at the time of reading and from optical path length information and the like of the respective measurement spots 705a, 705b, and 705c read from the analysis device 1.

As seen, since an optical path length can be measured without being inhibited by a reagent even if the reagent is being held at a measurement spot, analysis results can be derived with higher accuracy even if there is a variance in the thickness of the adhesive layer 711 caused by operational variations during the bonding process.

Fourth Embodiment

The third embodiment illustrated in FIG. 36 is arranged such that the height of an analysis region 721 is greater than that of a reagent holding region 722. A fourth embodiment according to the present invention illustrated in FIGS. 40A to 40C differs from the third embodiment in this aspect.

Figure 40A:
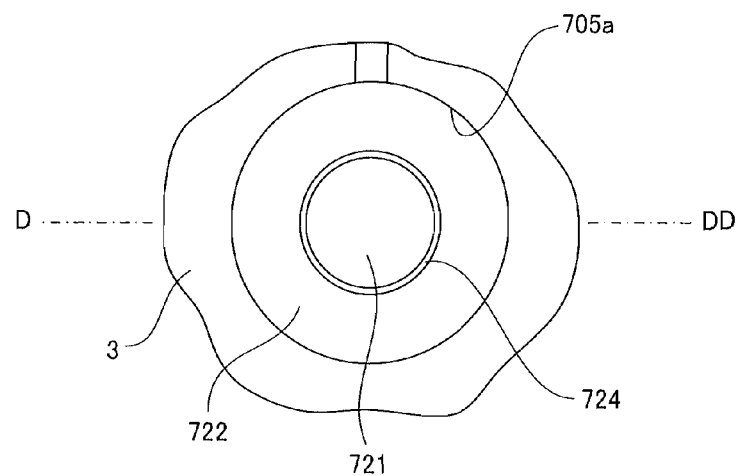
FIG. 40A is a plan view before bonding a cover substrate of a measurement spot of an analysis device according to a fourth embodiment of the present invention.
Figure 40B:
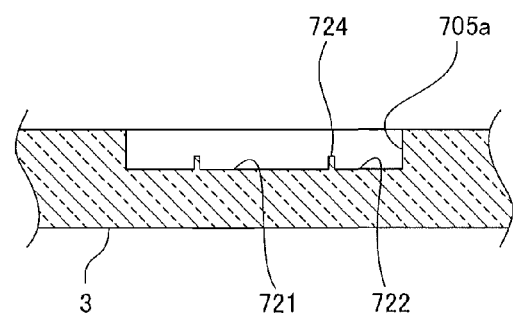
FIG. 40B is a cross-sectional view before reagent application taken along D-DD before bonding a cover substrate of a measurement spot of an analysis device according to the fourth embodiment of the present invention.
Figure 40C:
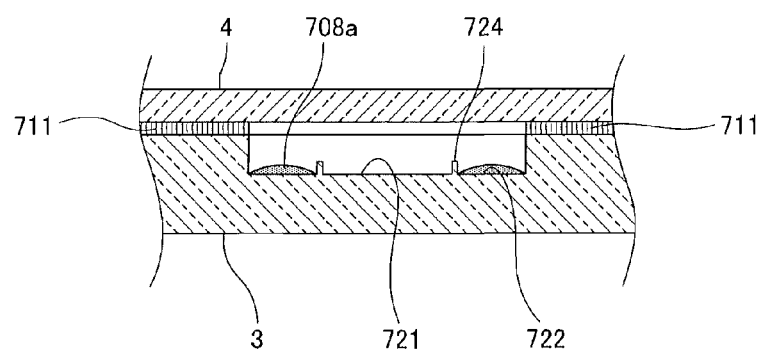
FIG. 40C is a cross-sectional view after bonding a cover substrate of a measurement spot of an analysis device according to the fourth embodiment of the present invention.

FIG. 40A is a plan view illustrating a base substrate 3 of an analysis device 1 configured by bonding together the base substrate 3 and a cover substrate 4. FIG. 40B is a cross-sectional view prior to applying a reagent of a measurement spot 705 taken along D-DD in FIG. 40A. FIG. 40C is a cross-sectional view after bonding the cover substrate.

In the present fourth embodiment, even by forming the analysis region 721 and the reagent holding region 722 to the same height as illustrated in FIGS. 40A and 40B, forming a protrusion 724 on a boundary between the analysis region 721 and the reagent holding region 722, dropping a necessary amount of a liquid reagent 708a onto the reagent holding region 722 with the aforementioned reagent dispenser 712 so that the reagent 708a is held as illustrated in FIG. 40C, penetration of the reagent 708a into the analysis region 721 can be prevented. The same logic applies to the measurement spots 705b and 705c.

Fifth Embodiment

The third embodiment illustrated in FIG. 36 is arranged such that the height of an analysis region 721 is greater than that of a reagent holding region 722. A fifth embodiment according to the present invention illustrated in FIGS. 41A to 41C differs from the third embodiment in this aspect.

Figure 41A:
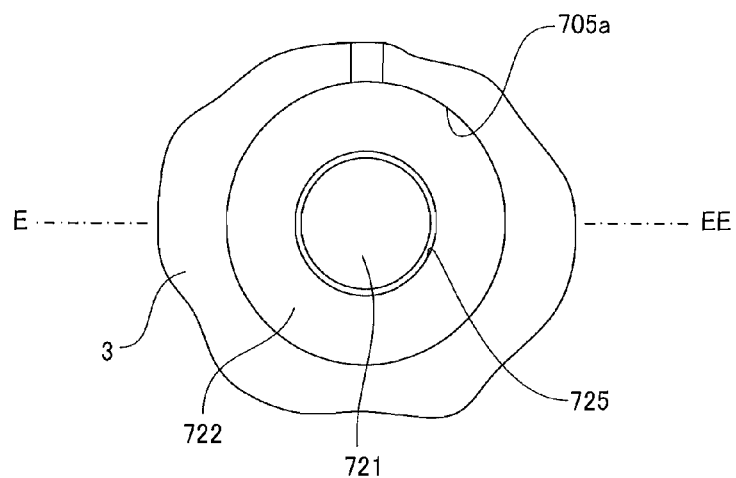
FIG. 41A is a plan view before bonding a cover substrate of a measurement spot of an analysis device according to a fifth embodiment of the present invention.
Figure 41B:
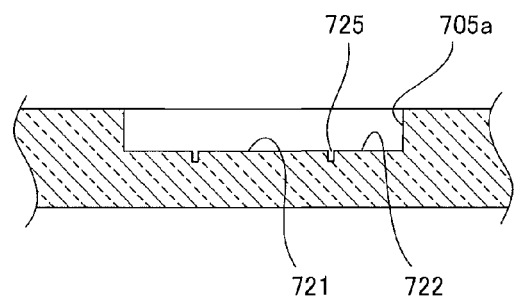
FIG. 41B is a cross-sectional view before reagent application taken along E-EE before bonding a cover substrate of a measurement spot of an analysis device according to the fifth embodiment of the present invention.
Figure 41C:
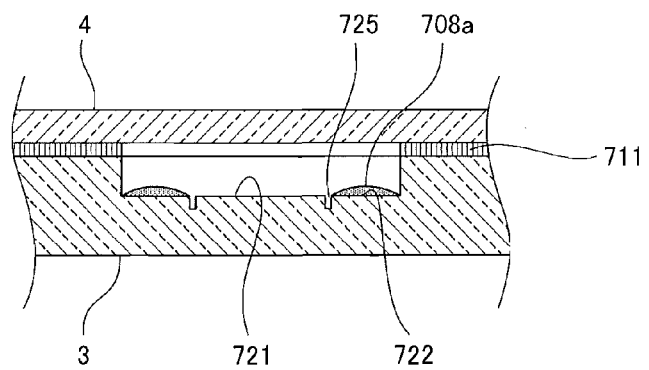
FIG. 41C is a cross-sectional view after bonding a cover substrate of a measurement spot of an analysis device according to the fifth embodiment of the present invention.

FIG. 41A is a plan view illustrating a base substrate 3 of an analysis device 1 configured by bonding together the base substrate 3 and a cover substrate 4. FIG. 41B is a cross-sectional view prior to applying a reagent of a measurement spot 705 taken along E-EE in FIG. 41A. FIG. 41C is a cross-sectional view after bonding the cover substrate.

In the present fifth embodiment, even by forming the analysis region 721 and the reagent holding region 722 to the same height as illustrated in FIGS. 41A and 41B, forming a depression 725 on a boundary between the analysis region 721 and the reagent holding region 722, dropping a necessary amount of a liquid reagent onto the reagent holding region 722 with the aforementioned reagent dispenser 712 so that the reagent is being held as illustrated in FIG. 41C, penetration of the reagent into the analysis region 721 can be prevented. The same logic applies to the measurement spots 705b and 705c.

Sixth Embodiment

Figure 42A:
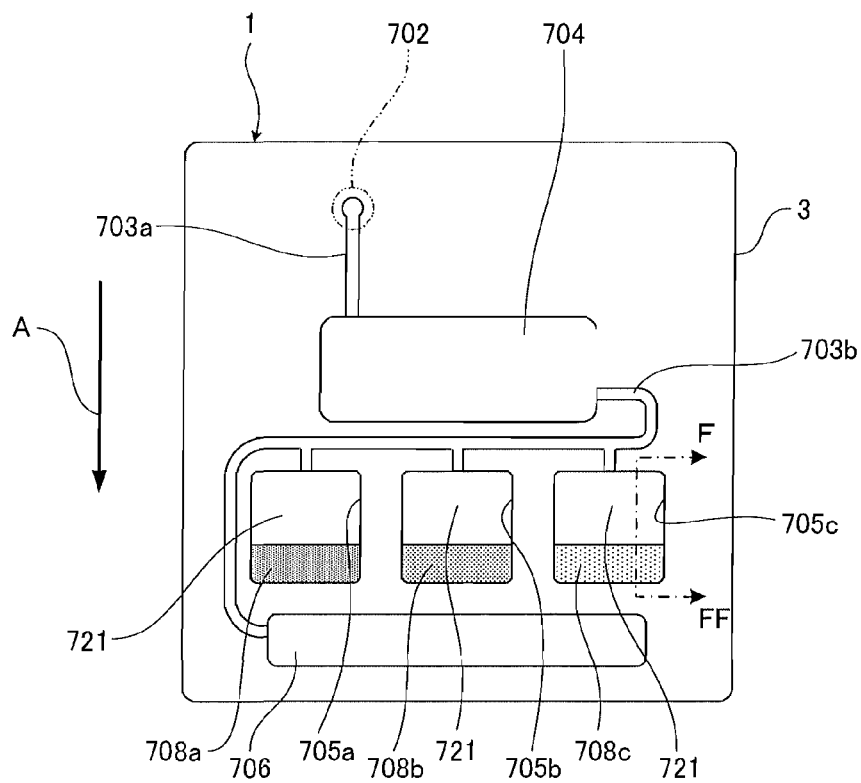
FIG. 42A is a plan view of a base substrate according to a sixth embodiment of the present invention.
Figure 42B:
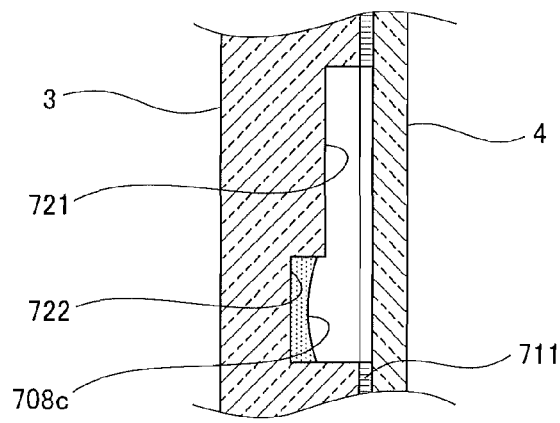
FIG. 42B is a cross-sectional view taken along F-FF of a base substrate according to the sixth embodiment of the present invention.

Although the respective embodiments described above are arranged such that a reagent holding region 722 surrounds the outside of an analysis region 721, a sixth embodiment of the present invention illustrated in FIGS. 42A and 42B differs from the respective embodiments described above in this aspect.

FIG. 42A is a plan view illustrating a base substrate 3 of an analysis device 1 configured by bonding together the base substrate 3 and a cover substrate 4. FIG. 42B is a cross-sectional view of a measurement spot 705c taken along F-FF in FIG. 42A.

In the present sixth embodiment, a reagent holding region 722 that is deeper than an analysis region 721 is formed in the measurement spot 705c at an outermost end in a direction A of a centrifugal force that is generated when an analysis device 1 is set on a rotor 103 and rotated. A reagent 708c is held by the reagent holding region 722. The same logic applies to the measurement spots 705a and 705b.

While a case where the analysis region 721 and the reagent holding region 722 have different heights has been described as an example in the present sixth embodiment, the present sixth embodiment can also be realized by forming the analysis region 721 and the reagent holding region 722 so as to have equal heights and providing a protrusion 724 illustrated in FIGS. 40A to 40C in a direction intersecting the direction A of the centrifugal force so as to separate the analysis region 721 from the reagent holding region 722.

Moreover, while a case where the analysis region 721 and the reagent holding region 722 have different heights has been described as an example in the present sixth embodiment, the present sixth embodiment can also be realized by forming the analysis region 721 and the reagent holding region 722 so as to have equal heights and providing a depression 725 illustrated in FIGS. 41A to 41C in a direction intersecting the direction A of the centrifugal force so as to separate the analysis region 721 from the reagent holding region 722.

Seventh Embodiment

Figure 43A:
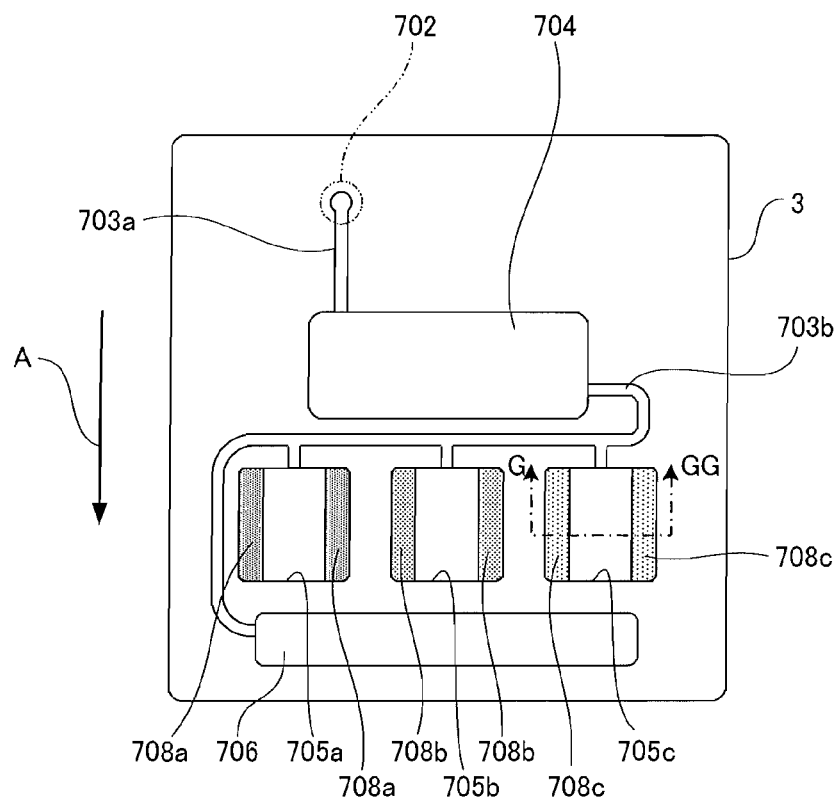
FIG. 43A is a plan view of a base substrate according to a seventh embodiment of the present invention.
Figure 43B:
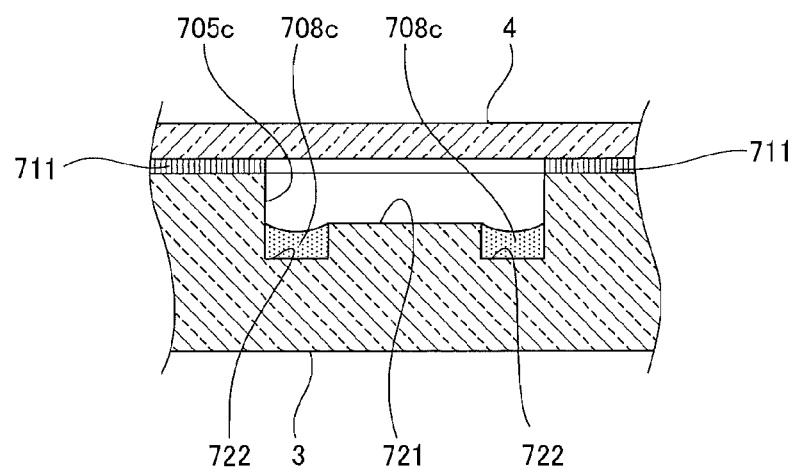
FIG. 43B is a cross-sectional view taken along G-GG of a base substrate according to the seventh embodiment of the present invention.

Although the respective embodiments described above are arranged such that a reagent holding region 722 surrounds the outside of an analysis region 721, a seventh embodiment of the present invention illustrated in FIGS. 43A and 43B differs from the respective embodiments described above in this aspect.

FIG. 43A is a plan view illustrating a base substrate 3 of an analysis device 1 configured by bonding together the base substrate 3 and a cover substrate 4. FIG. 43B is a cross-sectional view of a measurement spot 705c taken along G-GG in FIG. 43A.

In the present seventh embodiment, an analysis region 721 is formed as illustrated in FIG. 43A in the measurement spot 705c along a direction A of a centrifugal force that is generated when an analysis device 1 is set at the center of the measurement spot 705c on a rotor 103 and the analysis device 1 is rotated. Reagent holding regions 722 that are deeper than the analysis region 721 are formed as illustrated in FIG. 43B on both sides of the analysis region 721 along the direction A of the centrifugal force. A reagent 708c is held by the reagent holding regions 722. The reagent holding region 722 may be formed only on one side of the analysis region 721 instead on both sides thereof.

When forming the reagent holding regions on both sides of the analysis region 721 in the present seventh embodiment, the types of reagents to be held by the two reagent holding regions 722 are the same. However, the types of reagents to be held by the two reagent holding regions 722 formed on both sides of the analysis region 721 may differ from each other.

While a case where the analysis region 721 and the reagent holding region 722 have different heights has been described as an example in the present seventh embodiment, the present seventh embodiment can also be realized by forming the analysis region 721 and the reagent holding region 722 so as to have equal heights and providing a protrusion 724 illustrated in FIGS. 40A to 40C along a direction A of the centrifugal force so as to separate the analysis region 721 from the reagent holding region 722.

Moreover, while a case where the analysis region 721 and the reagent holding region 722 have different heights has been described as an example in the present seventh embodiment, the present seventh embodiment can also be realized by forming the analysis region 721 and the reagent holding region 722 so as to have equal heights and providing a depression 725 illustrated in FIGS. 41A to 41C along a direction A of the centrifugal force so as to separate the analysis region 721 from the reagent holding region 722.

Eighth Embodiment

Figure 44:
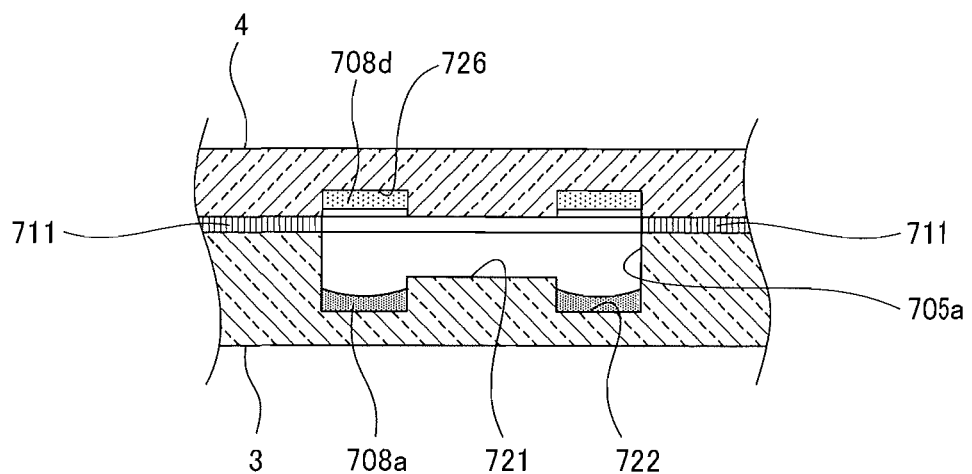
FIG. 44 is a cross-sectional view of an analysis device according to an eighth embodiment of the present invention.

While the respective embodiments described above are arranged so that a reagent holding region 722 is only formed on the side of a base substrate 3 of an analysis device 1 configured by bonding together the base substrate 3 and a cover substrate 4, an eighth embodiment of the present invention illustrated in FIG. 44 differs from the respective embodiments described above in this aspect.

FIG. 44A is a cross-sectional view illustrating the same position of the analysis device 1 configured by bonding together the base substrate 3 and the cover substrate 4 as illustrated in FIG. 36. A groove 726 is formed not only on the side of the base substrate 3 but also on the side of the cover substrate 4 at a position not opposing an analysis region 721 of the base substrate 3. The eighth embodiment may be configured such that a reagent 708d is held in the groove 726. The same logic applies to the measurement spots 705a and 705b.

In the present eighth embodiment, the type of the reagent 708a on the side of the base substrate 3 and the type of the reagent 708d on the side of the cover substrate 4 may either be the same or different from each other.

While a modification of the third embodiment has been described in the description of the present eighth embodiment provided above, each of the fourth to seventh embodiments can also be configured such that a groove is formed on the side of the cover substrate 4 at a position not opposing an analysis region 721 and that a reagent is held in the groove.

Moreover, while a modification of the third embodiment has been described in the description of the present eighth embodiment provided above, each of the fourth to seventh embodiments can also be configured such that a protrusion or a depression that separates the analysis region from the reagent holding region is also formed on the side of the cover substrate 4 and that a reagent is also held on the side of the cover substrate 4.

Ninth Embodiment

The analysis device according to the third embodiment described above is arranged such that the height of an analysis region 721 is greater than that of a reagent holding region 722. A ninth embodiment according to the present invention illustrated in FIG. 45 differs from the third embodiment in this aspect.

Figure 45:
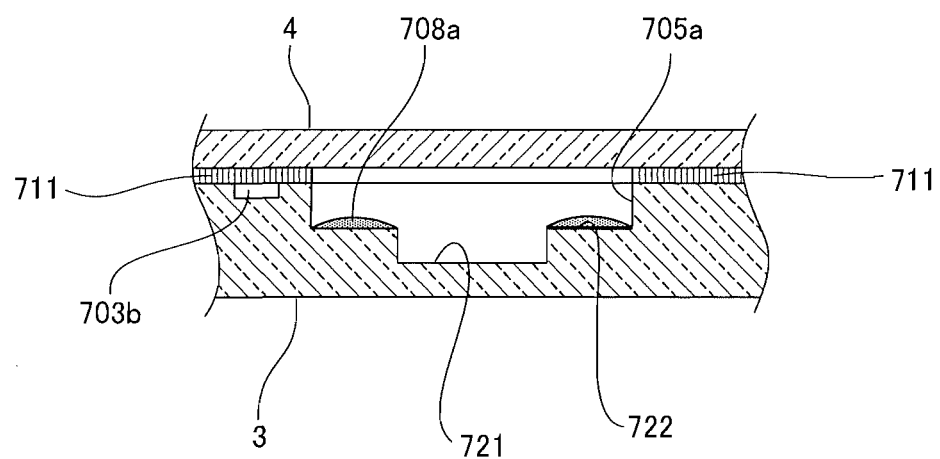
FIG. 45 is a cross-sectional view of a measurement spot of an analysis device according to a ninth embodiment of the present invention.

A plan view of a base substrate 3 according to the ninth embodiment is the same as FIG. 35A. As illustrated in FIG. 45 which is a B-BB cross section of a measurement spot 705, the height of the analysis region 721 is formed so as to be lower than that of the reagent holding region 722. Otherwise, the ninth embodiment is the same as the third embodiment. The same logic applies to the measurement spots 705a and 705b.

Tenth Embodiment

With the analysis devices of the respective embodiments described above, a reagent held at a single measurement spot is arranged so as to be dissolved at once in a sample liquid filling the measurement spot to cause a reaction, and is subsequently used to analyze the concentration of a single specific component from the amount of transmitted light in an analysis region with an analysis apparatus. However, a tenth embodiment according to the present invention illustrated in FIGS. 46A, 46B, and 47A to 47E represents a case where the analysis of a specific component requires two reaction steps with a reagent and a sample liquid.

Processes will now be described in sequence.

Figure 46A:
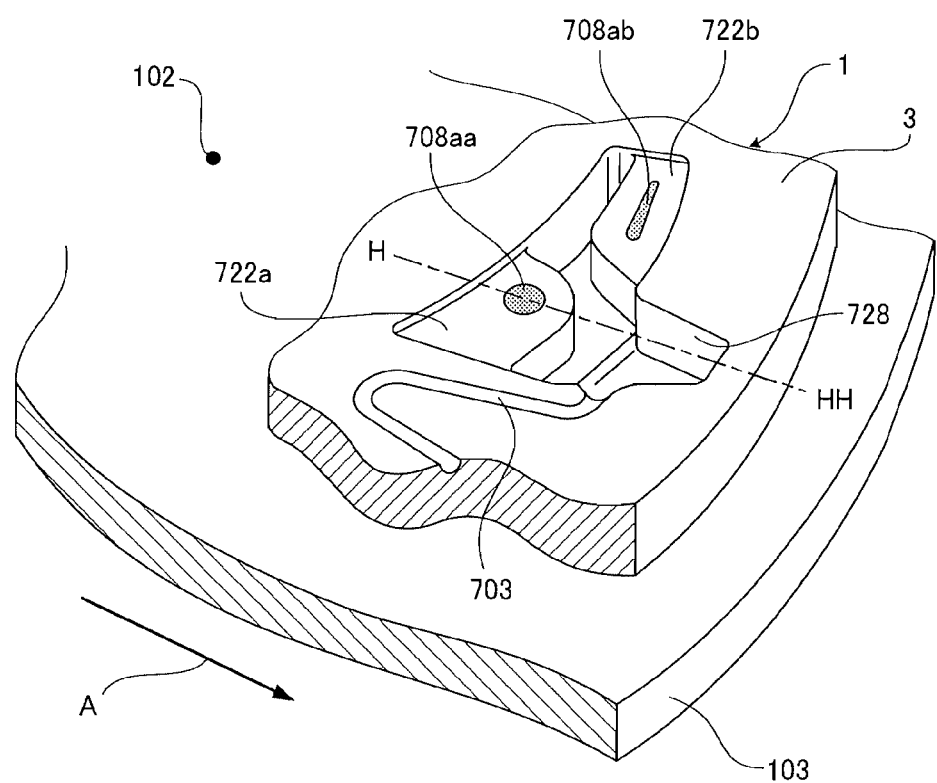
FIG. 46A is a perspective view of a base substrate-side of a measurement spot of an analysis device according to a tenth embodiment of the present invention.
Figure 46B:
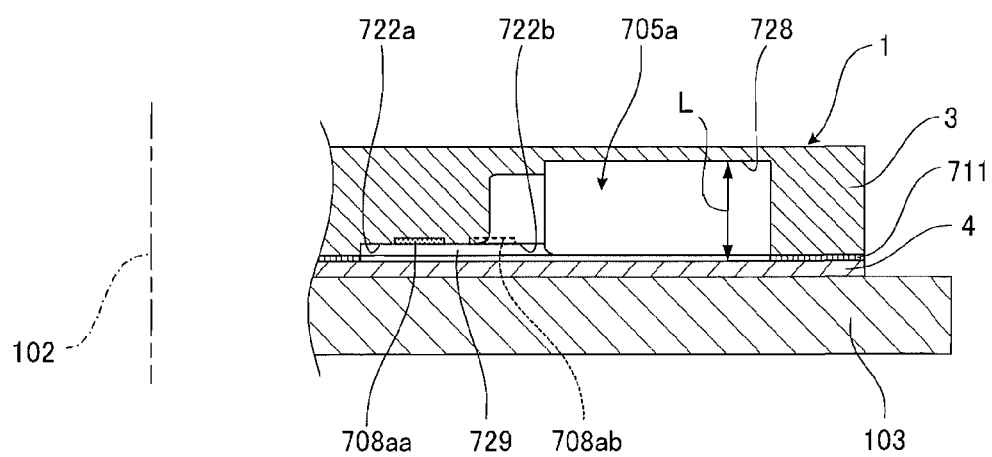
FIG. 46B is a cross-sectional view of a measurement spot of an analysis device set to an analysis apparatus according to the tenth embodiment of the present invention.

FIG. 46A is a perspective view illustrating a substantial portion of a base substrate 3 of an analysis device 1 that is configured by bonding together the base substrate 3 and a cover substrate 4. FIG. 46B is a cross-sectional view of a state where the analysis device 1 is set on the aforementioned rotor 103 of an analysis apparatus main body 100. The base substrate 3 illustrated in FIG. 46B represents a cross section taken along H-HH in FIG. 46A.

As illustrated in FIG. 46A, formed in a depression of the base substrate 3 to become a measurement spot 705a are: a liquid receiving section 728 formed as an analysis region 721 at an circumferentially outermost section with respect to an axial center 102 of the rotor 103; and a first reagent holding region 722a and a second reagent holding region 722b formed as reagent holding regions 722 adjacent to the liquid receiving section 728 on the circumferentially inward side of the liquid receiving section 728 with respect to the axial center 102 of the rotor 103.

The liquid receiving section 728 and the first and second reagent holding regions 722a and 722b are closed and covered by the cover substrate 4 as illustrated in FIG. 41B so as to form the measurement spot 705a. A gap 729 in which capillary force acts on a sample liquid is formed between the first and second reagent holding regions 722a and 722b and the inside of the cover substrate 4. Before bonding the cover substrate 4 to the base substrate 3, the first reagent holding region 722a is arranged so as to hold a first reagent 708aa. Before bonding the cover substrate 4 to the base substrate 3, the second reagent holding region 722b is arranged so as to hold a second reagent 708ab that is of a different type from the first reagent 708aa.

In a state where a sample liquid has not yet been received in the liquid receiving section 728, an optical path length L is measured using a laser length measuring machine 723 in the same manner as illustrated in FIGS. 38A and 38B. The optical path length L is converted into a barcode and printed by the analysis device 1 or recorded on a data carrier attached to the analysis device.

An analysis process is executed as follows using the analysis device 1 arranged so as to hold the first and second reagents 708aa and 708ab as described above.

Figure 47A:
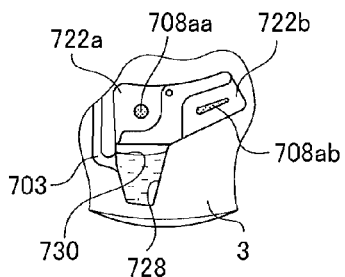
FIG. 47A is an explanatory diagram of an attitude control process of an analysis device by an analysis apparatus according to the tenth embodiment of the present invention.
Figure 47B:
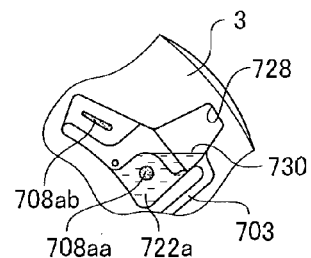
FIG. 47B is an explanatory diagram of an attitude control process of an analysis device by an analysis apparatus according to the tenth embodiment of the present invention.

A blood plasma component of blood or the like is used as the sample liquid. A constant amount of a blood plasma component of blood separated by a centrifugal separation machine is extracted by a micropipette and injected into the analysis device 1. The injected sample liquid is transferred as illustrated in FIG. 47A to the liquid receiving section 728 via a channel 703 by capillary action and a centrifugal force generated by the rotation of the rotor 103. Next, the rotor 103 is stopped when the first reagent holding region 722a of the analysis device 1 is positioned downward as illustrated in FIG. 47B. As a result, a sample liquid 730 in the liquid receiving section 728 is held by the gap 729 of the first reagent holding region 722a. By suspending the rotor 103 for a prescribed period of time in this state, the first reagent 708aa is dissolved into and reacts with the sample liquid 730 (first reaction).

Figure 47C:
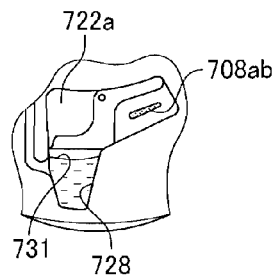
FIG. 47C is an explanatory diagram of an attitude control process of an analysis device by an analysis apparatus according to the tenth embodiment of the present invention.

Next, by rotating the rotor 103, a mixed liquid 731 held in the gap 729 of the first reagent holding region 722a is transferred as illustrated in FIG. 47C to the liquid receiving section 728 by the centrifugal force.

Figure 47D:
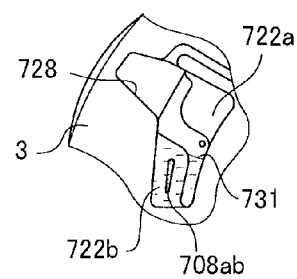
FIG. 47D is an explanatory diagram of an attitude control process of an analysis device by an analysis apparatus according to the tenth embodiment of the present invention.

Subsequently, the rotor 103 is stopped when the second reagent holding region 722b of the analysis device 1 is positioned downward as illustrated in FIG. 47D. As a result, the mixed liquid 731 in the liquid receiving section 728 is held by the gap 729 of the second reagent holding region 722b. By suspending the rotor 103 for a prescribed period of time in this state, the second reagent 708ab is further dissolved into and reacts with the mixed liquid 731 (second reaction) to become a mixed liquid 732.

Figure 47E:
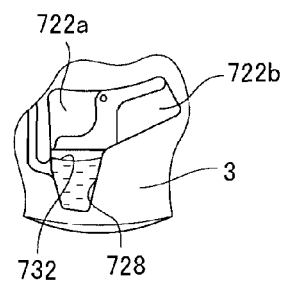
FIG. 47E is an explanatory diagram of an attitude control process of an analysis device by an analysis apparatus according to the tenth embodiment of the present invention.

Next, by rotating the rotor 103, the mixed liquid 732 held in the gap 729 of the second reagent holding region 722b is transferred as illustrated in FIG. 47E to the liquid receiving section 728 by the centrifugal force. Reading is executed at a timing where the measurement spot 705a whose liquid receiving section 728 is filled with the mixed liquid 732 into which the second reagent 708ab is dissolved passes between the aforementioned light source 105 and photodetector 106 of the analysis apparatus main body 100. The concentration of a specific component in the sample liquid is computed from an absorbance at the time of reading and from optical path length information and the like of the measurement spot 705a read from the analysis device 1 and retained in advance.

As seen, since an optical path length can be measured without being inhibited by a reagent even if the first and second reagents 708aa and 708ab are held at the measurement spot 705a, analysis results can be derived with higher accuracy even if there is a variance in the thickness of the adhesive layer 711 caused by operational variations during the bonding process. In addition, since a plurality of reagent holding regions 708aa and 708ab holding reagents of different types is provided in a single measurement spot 705a, an analysis of specific components that requires two reaction steps between the reagents and a sample liquid can be performed by attitude control of the analysis device 1 by the analysis apparatus main body 100 and by using only the single measurement spot 705a. The same logic applies to the measurement spots 705b and 705c.

Moreover, in the respective embodiments described above, while a blood cell separation process as preprocessing of analysis is arranged so as to be performed outside of the analysis device 1, the respective embodiments described above can also be arranged such that, after setting the analysis device 1 onto the analysis apparatus main body 100, blood cells are separated by rotational control of the rotor 103 and subsequently transferred to the measurement spots 705a, 705b, and 705c.

In addition, in the respective embodiments described above, while centrifugal force that accompanies the rotation of the rotor 103 is used to transfer a sample liquid to the measurement spots 705a, 705b, and 705c, the respective embodiments described above can also be arranged such that the sample liquid is transferred to the measurement spots using a pump instead of having to rely on centrifugal force.

Furthermore, the third to seventh embodiments and the ninth embodiment are arranged such that a depression is formed on the bottom faces (on the side of the base substrate 3) and a protrusion is formed on the upper faces (on the side of the cover substrate 4) of the single measurement spots 705a, 705b, and 705c, whereby one of the depression and the protrusion is used as a reagent holding region and the other of the depression and the protrusion is used as an analysis region. Alternatively, the third to seventh embodiments and the ninth embodiment can be arranged such that a protrusion is formed on the bottom faces (on the side of the base substrate 3) and a depression is formed on the upper faces (on the side of the cover substrate 4) of the single measurement spots 705a, 705b, and 705c, whereby one of the depression and the protrusion is used as a reagent holding region and the other of the depression and the protrusion is used as an analysis region.

INDUSTRIAL APPLICABILITY

Since the present invention is capable of accurately transferring a predetermined amount of a solid component from a separation cavity to a measurement channel, analysis accuracy can be improved. Therefore, the present invention is useful as a transfer control unit of an analysis device to be used for analyzing a liquid component collected from a living organism or the like.

The present invention is particularly useful in fields where the present invention is used for automatic measurement when analyzing of hemoglobin and hemoglobin A1c components in a simple and speedy manner.

The invention claimed is:

1. An analysis method using an analysis device having a microchannel structure that transfers a sample liquid towards a measurement spot by centrifugal force generated by rotating the analysis device about a rotation center and which is used to read a reactant at the measurement spot, the analysis method comprising:
    injecting the sample liquid into the analysis device;
    transferring the sample liquid into an immunoassay cavity that holds a latex reagent sensitized by an antibody that specifically reacts with a particular component in the sample liquid, so as to create an immunoassay solution by an immunoreaction between the sample liquid and the latex reagent;
    transferring the immunoassay solution into an agglutinative reaction cavity that holds an agglutination reagent, so as to create an agglutinated solution by agglutination reaction between the immunoassay solution and the agglutination reagent; and
    measuring the agglutinated solution by irradiating a light to the agglutinated solution;
    wherein an average particle size of the latex reagent is in a range from 0.12 µm to 0.31 µm, and a mixing ratio of the antibody-sensitized latex reagent and an antigen inside the agglutination reagent is antigen-excessive.

2. The analysis method according to claim 1, wherein a mean value of particle sizes of agglutinated substances within three minutes of the agglutination reaction between the immunoassay solution and the agglutination reagent is equal to or less than 700 nm.

3. The analysis method according to claim 2, wherein a centrifugal force applied to the agglutinated substances during a measurement is equal to or less than 200 G.

4. The analysis method according to claim 1, wherein the immunoreaction involves having a latex reagent react to a mixed solution that combines the sample liquid with a diluent measured inside the analysis device.

5. The analysis method according to claim 4, wherein the sample liquid is blood, the analysis method further comprising:
    condensing a blood cell component in the blood by centrifugal force after injecting the blood into the analysis device;
    collecting a constant amount of blood containing the blood cell component; and
    mixing the constant amount of blood and the diluent so as to create the mixed solution.

6. The analysis method using the analysis device according to claim 4, further comprising:
    measuring the mixed solution before the immunoreaction between the mixed solution and the latex reagent.

7. The analysis method according to claim 1, wherein the sample liquid is denaturized by a denaturing regent so as to ensure that an immunoreaction occurs between a specific component in the sample liquid and the latex reagent.

* * * * *